(12) United States Patent
Breitling et al.

(10) Patent No.: US 8,771,960 B2
(45) Date of Patent: Jul. 8, 2014

(54) METHOD FOR PRODUCING PROTEIN LIBRARIES AND FOR SELECTING PROTEINS FROM SAID LIBRARIES

(75) Inventors: Frank Breitling, Heidelberg (DE); Gerhard Moldenhauer, Heidelberg (DE); Annemarie Poustka, Heidelberg (DE); Thorsten Kühlwein, Viernheim (DE); Sandra Lüttgau, Dossenheim (DE)

(73) Assignee: Deutsches Krebsforschungszentrum, Heidelburg (DE)

( * ) Notice: Subject to any disclaimer, the term of this patent is extended or adjusted under 35 U.S.C. 154(b) by 910 days.

(21) Appl. No.: 10/491,653

(22) PCT Filed: Sep. 27, 2002

(86) PCT No.: PCT/EP02/10852
§ 371 (c)(1),
(2), (4) Date: Jun. 25, 2004

(87) PCT Pub. No.: WO03/029458
PCT Pub. Date: Apr. 10, 2003

(65) Prior Publication Data
US 2005/0059082 A1    Mar. 17, 2005

(30) Foreign Application Priority Data
Oct. 1, 2001   (EP) .................................. 01123596

(51) Int. Cl.
*G01N 33/53* (2006.01)
*C12N 15/13* (2006.01)

(52) U.S. Cl.
USPC .......................................... 435/7.1; 435/455

(58) Field of Classification Search
None
See application file for complete search history.

(56) References Cited

U.S. PATENT DOCUMENTS

| | | | |
|---|---|---|---|
| 5,202,238 A | 4/1993 | Fell, Jr. et al. | |
| 5,871,907 A | 2/1999 | Winter et al. | |
| 6,010,884 A | 1/2000 | Griffiths et al. | |
| 6,091,001 A | 7/2000 | Jakobovits et al. | |
| 6,214,613 B1 * | 4/2001 | Higuchi et al. | 435/320.1 |
| 6,284,536 B1 | 9/2001 | Morrison et al. | |
| 6,406,863 B1 * | 6/2002 | Zhu et al. | 435/7.1 |
| 7,884,054 B2 | 2/2011 | Zhou | |

FOREIGN PATENT DOCUMENTS

| | | |
|---|---|---|
| WO | WO 93/19172 A1 | 9/1993 |
| WO | WO 99/20780 A1 | 4/1999 |
| WO | WO 00/05355 | 2/2000 |
| WO | WO 00/31236 | 6/2000 |
| WO | WO 00/76310 A1 | 12/2000 |

OTHER PUBLICATIONS

Waterhouse, P. et al., "Combinatorial infection and in vivo recombination: a strategy for making large phage antibody repertoires", 1993, Nucleic Acids Research, vol. 21, No. 9, pp. 2265-2266.

Higuchi, K. et al., "Cell display library for gene cloning of variable regions of human antibodies to hepatitis B surface antigen", 1997, Journal of Immunological Methods, 202:193-204.

O'Gorman, S. et al., "Recombinase-Mediated Gene Activation and Site-Specific Integration in Mammalian Cells", 1991, Science, 251:1351-1354.

Watson, J. et al., "Recombinant DNA", 1992, Scientific American Books, 2nd edition, chapter 12, pp. 228-232.

Jiang, R. et al., "Gene targeting: Things go better with Cre", 1997, Current Biology, vol. 7, No. 5, pp. R321-R323.

Nagy, A., "Cre Recombinase: The Universal Reagent for Genome Tailoring", 2000, Genesis, No. 26, pp. 99-109.

Peterson, M. et al., "Regulated production of $\mu m$ and $\mu s$ mRNA requires linkage of the poly(A) addition sites and is dependent on the length of the $\mu s$-$\mu m$ intron", 1986, Proc. Natl. Acad. Sci. USA; vol. 83, pp. 8883-8887.

* cited by examiner

*Primary Examiner* — Michael Burkhart
(74) *Attorney, Agent, or Firm* — Chao Hadidi Stark & Barker LLP

(57) ABSTRACT

The invention relates to a method for the production of a protein library, in particular an antibody library, which is highly diverse and for the selection of proteins, in particular antibodies, therefrom.

20 Claims, 22 Drawing Sheets

Fig 12A (pBS MhKappaM)

Fig 12B (pBS MhIgG1M; pBS MhIgG1Mdelta350)

Fig. 13A (pBS MKappaG418M)

Fig. 13B (pBS MvHG418M; pBS MvHG418MdeltaPGK)

| Primer and gene-name | sequence | EMBL Data bank accession number | primer and gene-name | sequence | EMBL data bank accession number |
|---|---|---|---|---|---|
| v1-2L | ccacagggacctctgggctga | D87021 | v3-4L | actctatccctgggggaccaca | D87022 |
| v1-4L | ggcttcagggacctctgggct | D87015 | | | |
| v1-5L | ggcttcggggacctctgggct | D87007 | v4-1L | cctcagagatcaggggccagcc | D87009 |
| v1-9L | ggaaatggccttggggacctct | D87014 | v4-3L | gggtcagccacacagcctgatt | D87016 |
| v1-11L | agagaggccctgggaagccca | D87009 | v4-4L | gagtctcagtgtccaacctacac | D87018 |
| v1-13L | ggccctgggaagcctatggatt | D87010 | v5-1L | cccagggaattcagggaaatgttt | D87024 |
| v1-17L | ccctgggaagcccatggggc | D87016 | v5-2L | ccccaaagggacccccacctc | D87016 |
| v1-18L | gatcgaggggagggtccctg | D87018 | v5-4L | gaccctcagcatcccatgccc | D87000 |
| v1-19L | gaggggtccaggaagcccatg | D87018 | | | |
| | | | U266L | ccacagggacctctgggctga | X51754 |
| v2-1L | tggatgggctcggcggggct | D87023 | | | |
| v2-6L | gcaggggggaggggctgctg | D87021 | J1L | cagaggggaggatgccccaga | D87023 |
| v2-7L | tgccccaggctcagtgcccat | D87021 | J2L | gctgaccacaagttgagacaagat | D87023 |
| v2-11L | ccaggctcagtccccacagatt | D87015 | J3L | gctgaccacaagttgagacaagat | D87023 |
| v2-13L | ctcaaccccatattatcatgctag | D87007 | J7L | gcttagaccttagccttcgaca | D87017 |
| v2-14L | gctggggctgattgcagggggata | D87007 | | | |
| v2-15L | ccagaccctgcccaggctc | D87007 | | | |

Figur 14A

| primer IGKV and gene-name | sequence | EMBL data bank accession number | primer IGKV and gene-name | sequence | EMBL data bank accession number |
|---|---|---|---|---|---|
| 1-5 | cactaggaatttactcagcccagt | Z00001 | 2D-24 | gagggaatggtagaggaaacttct | X63401 |
| 1-6 | gcagtttactcagcccagggtg | M64858 | 2D-28 | aaaatataaaggtcttatactttacaa | X12691 |
| 1-9 | ggaatttactcagcccagtg | Z00013 | 2D-29 | gcagtgctctgaataatatcttgag | M31952 |
| 1-12 | ctaggattatactcggtcagtgtg | V01577 | 2D-30 | tggtgtggggtcttctggagac | X63402 |
| 1-16 | gcagtttactcagcccagggtg | J00248 | 2D-40 | atgaccagtgctctgattaagaac | X59311 |
| 1-17 | ctcagcccagagtgctcagtac | X72808 | | | |
| 1-27 | attcagccagtgtagccactaatg | X63398 | 3-11 | ctcttgccacctctgctcagca | X01668 |
| 1-33 | cactaggaattttctcagccagtg | M64856 | 3-15 | ctcctgccacctctgctcagc | M23090 |
| | | | 3-20 | agtcctgttacctgctcaactctg | X12686 |
| 1D-8 | ctcagccaatgtgctcagtacag | Z00008 | | | |
| 1D-12 | tactcggtcagtgtgctgagtact | X17263 | 3D-7 | actccatcaggagttttctctgct | X72820 |
| 1D-16 | actcagcccaggggtgctcagta | K01323 | 3D-11 | ctcctgccacctctgctcagc | X17264 |
| 1D-17 | cactaacagtttactcagcccaga | X63392 | 3D-15 | ctcctgccacctctgctcagc | X72815 |
| 1D-33 | ctcagccagtgggctcagtaca | M64855 | 3D-20 | caagtcctgttacctggcaactc | X12687 |
| 1D-39 | ggaatttactcagccagtgtgct | X59312 | | | |
| 1D-43 | agcagtttactcagcccagtgtg | X72817 | 4-1 | cagagtaatatctgtgtagaaataaaa | Z00023 |
| 2-24 | gaaagagggaatggtagaggaaac | X12684 | 5-2 | tctcctctgtgccaccaagtcc | X02485 |
| 2-28 | gaaatatgacgtctggtgtctga | X63397 | | | |
| 2-29 | aaaactcctaaaagcagtgctctga | X63396 | JK1 | gattgcagagtcaccttatagatc | J00242 |
| 2-30 | ctggggaagactgacacagaaag | X63403 | JK2 | ccctggcatccgattaatgaaaat | J00242 |
| 2-40 | ggaacgatgaccagtgctctgat | X59314 | JK3 | gggtgaccaggttattcaaccaa | J00242 |
| | | | JK4 | ggtactctttggaattgacctgag | J00242 |
| | | | JK5 | ccaatctttaccaaactcctatttga | J00242 |

Figur 14B

| primer and gene-name | sequence | EMBL data bank accession number | primer and gene-name | sequence | EMBL data bank accession number |
|---|---|---|---|---|---|
| vH1-2 | aattatgtgtgttctctttctcatctt | AB019441 | vH3-49 | gtcctctcctcaggtgtccca | AB019438 |
| vH1-3 | catcctcctgttgggtaatccat | AB019441 | vH3-53 | cccggcctctcctcagatgtc | AB019438 |
| vH1-8 | gtggcatctgtgttttctttctcat | AB019440 | vH3-64 | tgccctctcctcaggcatctca | AB019437 |
| vH1-18 | tgtgtcgtccatgtgtcatgtattt | AB019440 | vH3-66 | cggcctctcctcagatgtccc | AB019437 |
| vH1-24 | ggtccacatgtcacctatcttct | AB019439 | vH3-72 | gcctctcctcaggcgtccca | AB019437 |
| vH1-45 | gtgtcgtttgtcttcccttcttat | AB019438 | vH3-73 | ccttctcgtcaggcgtccag | AB019437 |
| vH1-46 | atgggacatctatcttctttctcaa | AB019438 | vH3-74 | ccctgggtcctgctcttticttc | AB019437 |
| vH1-58 | tgtcatttaccttcccttcttatc | AB019438 | | | |
| vH1-69 | gtggcatctgtgttttctttctcat | AB019437 | vH4-4 | ccagggtgagcctaaaagactgg | AB019441 |
| | | | vH4-28 | tccagggagagcctaaaagactg | AB019439 |
| vH2-5 | actgatcatgttactatcactggtc | AB019440 | vH4-31 | cccagggagagtctaaaagactg | AB019439 |
| vH2-26 | acgcccacacctgagggctca | AB019439 | vH4-34 | ccaggtgagcccaaaagactg | AB019439 |
| vH2-70 | accccacacctgagggctca | AB019437 | vH4-39 | tcccaggtgagctcaaaagact | AB019439 |
| vH3-7 | tacagcctattcctccagcatcc | AB019440 | vH4-49 | ccaggcgagcccaaaagact | AB019438 |
| vH3-9 | cagcccactcagaggcatccc | AB019440 | vH4-61 | ccagggcgagcccaaaagact | AB019437 |
| vH3-11 | ctgccctctcctccagcgtcc | AB019440 | | | |
| vH3-13 | gccttcacctcagatgtcccac | AB019440 | vH5-51 | gccttttctgcatttgaggttc | AB019438 |
| vH3-15 | tgccctctgttcaggcatccca | AB019440 | | | |
| vH3-16 | gggctcagtcctctcctcagg | AB019440 | vH6-1 | ttgtagacctgagggcccgg | AB019441 |
| vH3-20 | cacagcctactctgaggcatcc | AB019440 | | | |
| vH3-21 | agcctattcctccagcgtccca | AB019439 | vH7-81 | aattgtgtcgtccgtgtgtcatg | AB019437 |
| vH3-23 | cactatctccaaaggcctctcac | AB019439 | | | |
| vH3-30 | ccagcctctcctcagatgtccc | AB019439 | JH1 | gagcacctgtcccaagtctga | X97051 |
| vH3-33 | ccagcctctcctcagatgtccc | AB019439 | JH2 | ccagacccaggccggctgca | X97051 |
| vH3-35 | ggctcagtcctctcctcaggt | AB019439 | JH3b | caaggagcccccggacattatc | X97051 |
| vH3-38 | gcactataacatcagaaagctggaa | AB019439 | JH4b | caggagacccagcacccttattt | X97051 |
| vH3-43 | cagcccactctgaggcatctgt | AB019438 | JH5b | aatgcctccaagactctgaccct | X97051 |
| vH3-48 | agcctactcctcaagggtccca | AB019438 | JH6b | aacatgccccgaggatccaacct | X97051 |

Figur 14C

Fig. 15A (pBS FRTvKappa)

Fig. 15B (pBS loxPvHmyc; pBS loxPvH)

Fig. 15C (pBS FRTKlon)

Fig. 15D (pBS loxPklon)

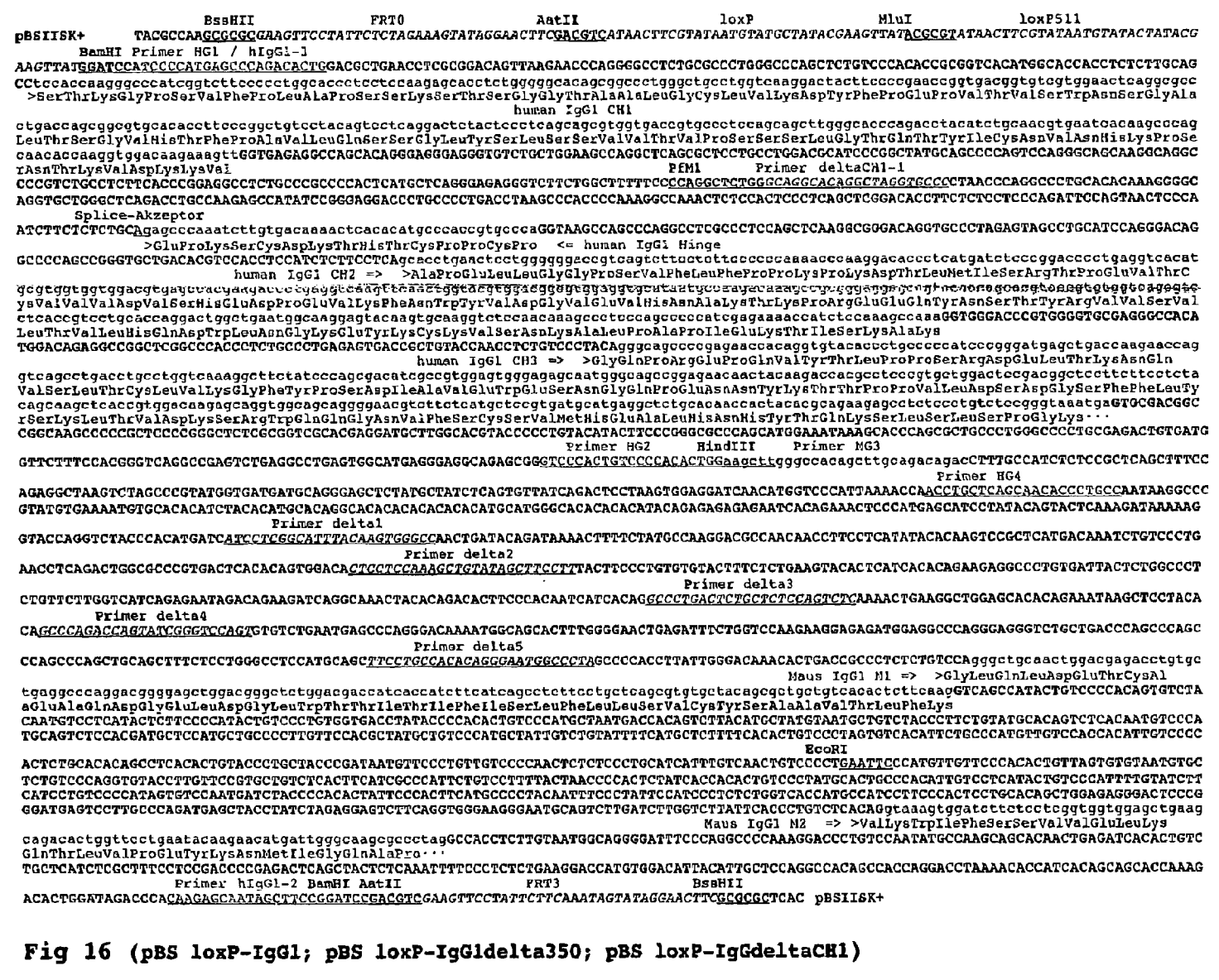

Fig. 17A (pBS FRT KappaHEAscFv215)

Fig. 17B (pBS FRT KappaHEAbla)

Fig. 18A (pBS FRT vKappa215)

Fig. 18B (pBS loxP-FdHEA)

SEQUENCE LISTING

```
<160> NUMBER OF SEQ ID NOS: 161

<210> SEQ ID NO 1
<211> LENGTH: 5454
<212> TYPE: DNA
<213> ORGANISM: Artificial Sequence
<220> FEATURE:
<223> OTHER INFORMATION: chimeric mouse-human DNA for humanization of
      HEA125
<220> FEATURE:
<221> NAME/KEY: misc_feature
<222> LOCATION: (4415)..(4415)
<223> OTHER INFORMATION: n is a, c, g, or t

<400> SEQUENCE: 1
tacgccaagc gcgcaattaa ccctcactaa agggaacaaa agctggagct ccaccgcggt      60
cggccgacaa aatggctttt cattagttat ccaaaatggt ttttaagtta tgttcctaac     120
aaatatggcc tcacctttga tgtaaacatc attttctttg tccaaatagt tatttagtgc     180
ataattatac tatagagcca aaattaagca tttgacattg gtacaatata tgaatatagt     240
tcaacaacat tttatcacat atttaaatgt atgtaaccac cactgaaatc aagacagtga     300
ttctgtgacc ttgaagatcc tccttgtgac agctcttttgt cacatttgtt ttcttatctg     360
taacatccct agatcctagg atcagtgatc tgtcctcttt ctctctaatg gtataatttc     420
```

```
accagtgtta aataaaaaga atacagcatg tgacattaga ttatattttt ttcacaaagc    480
acaaggttgc tcagaattat ataaatgctt atatgtattc tttcttcttt tttattgtgg    540
gttctgtttt agataagact cgaacatata tattttgagg aggcattttt gtattaatag    600
ccagattaga ggcactgttg attgataaat ttggttccca gaaatggatg aacaaggtta    660
tgctatttga aaagacaaat taaaaaaaag caattaaaag aagtttcaaa aagtggataa    720
taatgtacat tctcaagagg taggaaggca aagggttgcc ctctcctatt tggtgactgt    780
cctttcccat catccttatg tggactgaga aagggaagga gcagggaaac tggactgcat    840
attaactggg ggaagggaca ctaacattat tctgcactgc cttcagagtg tacgctgaga    900
agatgcttag taaatgtgtg ctgagtggat daccccacga gggactaaat gcagggggcct    960 ccacgaagag gggagaatg aaagtcattg ttagtgtcct cttccttccc taatgtaacc   1020
tttgatacgt gggctctcca tacccagaca aaattaccta tattctttga cctgttgatg   1080
aaggtctctt ctatctcatc ttatacatgg ctatttctaa ttcgatgcat gaaggaagag   1140
accccaagga gggatcatgt gtttgaatta tgtgttttgt actttgagct ctggaaggca   1200
gaatagtaga aggctcaagg ttgtgggaga tttgatcctg gatcccctac tttattgtct   1260
ttctggcctt gacgtatgat tcattccttg tatcctcttt tatgtatgca ctgggtatta   1320
gatatttctt taggtgaagt tattatgaag tatacaatat atacaggaag aacatagatc   1380
ccaattccac aatagtaact ttcacatccc atacagagag acagaacatt ccccaagccc   1440
cagagtttcc atcttgctac ctcaaaactt atgtctctct taattttaaa ttttacctgc   1500
ttttaaactt acatggatga aaaatgtttt tgttttgctt attatcttgt ttatgagatt   1560
aaactatgct cttaagtttt atttttattaa ttctccttat taagtaatag ctcaattgtg   1620
aacatgtcat aatttaactg ttggtggaca ttttggttgt atccagtttt agactttcat   1680
aaatgagtct ctcaatactg gttgcttctt aaggtttctg gtgtacagag ataagcacct   1740
aagagtgggg tgatcagctc tcagcttggt agaacttttc ccaaattttg atgtatgtgt   1800
gtaatctcac ggtatagagg tccttgaagt aggttgtggg tagtgcccag ccttgccaat   1860
ggcagatagg agccagctca tgtttaaaaa cttagtgaag gcacaaaagc agatgaagtc   1920
caagtactat gatgggcttc cacatttttcc tattgcatgc acatttaggt tgcctttgct   1980
tcctgtgata atgattctac tttgcttcgc caagtttact gggtaggttg aatcagatta   2040
cagaacatgt gcttgtaaag actgtccccc ttcaggactt tgacgactta ggggaagaaa   2100
actaggaagt atgcctcctc aaacctacca tggcccagag aaataagcca tgaatagtac   2160
tcgtgaacct tagaaaggac tgccatgtag tggacagcca accagggcaa gtggagggtt   2220
ttatttatcc tttaagtgtg gtggatttca ggcaactaa acatttaact tctttagaag   2280
agaaacccag gtaactggaa aaacaactga ttactaccat ttagtaagaa agacagagat   2340
ctcaagtgca aagactcact ttattgaata ttttctgcaa atattagcat gataaaagcc   2400
aaggaaaggg aggaggagga gaaggaggtg gggaggaggt ttggagcacc gcaacagtgg   2460
taggtcgctt gtggggaagc ctccaagacc ttagaaggga agataggatg gagctgggga   2520
gctggtggtg cggccgcttc tccctctaac actctcccct gttgaagctc tttgtgacgg   2580
gcgagctcag gccctgatgg gtgacttcgc aggcgtagac tttgtgtttc tcgtagtctg   2640
ctttgctcag cgtcagggtg ctgctgaggc tgtaggtgct gtccttgctg tcctgctctg   2700
tgacactctc ctgggagtta cccgattgga gggcgttatc caccttccac tgtactttgg   2760
cctctctggg atagaagtta ttcagcaggc acacaacaga ggcagttcca gatttcaact   2820
```

```
gctcatcaga tggcgggaag atgaagacag atggtgcagc cacagttcct gaggaaagaa    2880
gcaaacagga tggtgtttaa gtaacaaagt tctgcccttg ggtgtgttgt ttgcggataa    2940
tcacagggca tgttagggac agacagaaaa cagcatgctt atcccagata attataacaa    3000
ggagaccaag aagcgtattt aaaatcttga tgttttgagt ttcttcctag cttccccta    3060 ttccttaata aagttcgaag atattctcag gcttccttct attgcctttc ttccctgaaa    3120
ctacattctt ttcagttcca tgcttcagac agagattcag accagtttat ctgacactcc    3180
tgatgtttgg gagtctgaac acaagcacat aaggtaagag cagaaactgg cttcattttt    3240
ctcctgtctc ttccaagaat actctgatat tagcctctgt atggcttcct ttggtgtagc    3300
caagctaaac ctactgtatg acagggcct taagccaggg tctgtatttg ggtgtccaga    3360
aatattctga gcaattcatc agaccctggt ctaatggttt gtaaccacat gggacaattt    3420
ttagccacac cagaacaggt caactgtaat ctgggccacc tgcctgggag gaactggcag    3480
acttcacttc tgatcttaag caactgccag atggcctctc ggaaagtccc ctctgttgag    3540
atgccaactc ttgggtgaca gaggtagtaa aaacgaaaac tgagagttct ttaccaagaa    3600
aaacaataga attatgagca gccttcccc ccttaaaata aattaatagt taaaagggaa    3660
ttgacatcat tttaaagtaa ttaaaagtgg ttaaataact taatgactct aaagtagttt    3720
caagagtttt aaagggtcct taaatagttg cctttggcta gggaagggtc aaacacaaaa    3780
gctaataaat agttttcaaa attatgggat tatagtagct gagttaaaca ttttttctatc    3840 acagaattaa agtattggga aatattttg tgctaaatta ttattagtca tatttttgca    3900
tgaagaaaaa tatcctacct aaccagttaa ggtcatgtca caaatttata ttaatttaac    3960
cagttaatat gacatataat ttagaggagt ttagtgagag ttcagtcaaa gaatatttac    4020
catgactttt gctggctgta gattttacct ctaaaagatt atatacatta agcttttaat    4080
ataacactgg ataaagcagt ttatgcccct tctaattccc taatagaaaa ttaaaataag    4140
ggaatataat aataaatgca ttttatttct gaaatctcca ataagtcacc ctttccttgt    4200
ttttctcaca ttagtgtagt ctgtcacatc tctgttctct tcagattagt ggctctgttc    4260
ctatcactgt gcctcaggaa agtggtccac gcggagcaag ggatgctacc gcggggttc    4320 acatggccct tagcggcagg gtgaacgcca aatggctggc acagccgcga ggtcacccag    4380
ttgtaaagaa gaggttgcgg accgtttcag tccantgctg gcgatataaa attacaatcg    4440
agtaataact gggaaaacaa aggaccaaat gtcttacaaa accgtggcca ttaaaacata    4500
cagttcaaac ccaactgtat ttctactctt ataataaaaa agatcatttc aaatttactt    4560
tcatgtagaa atgagacaaa ggaaaaaaac cccttgagct gtctgtcaag gactcgttcc    4620
tacagagtct ctcattttga cattttgtga caaattttag aataagagtc acctcttc    4680 tgattattca gcaagccatg gtatctacat ggcaagcagt catactttca aacagcttaa    4740
tgattatttc aggacatact actgattttt gtagtcataa aaacttagga gacaaaagag    4800
agaactcagc ctacggctca ctcaactctg ctatcccact tttattgcaa aactcaagac    4860
agtacttgtg gaaactcaac acggatgagt ctccttctct tctcagagct ccaggccct    4920 ctttgatctg cgctgtttca tcctctgggt cattcagttt atcttcaaag tttgctccca    4980
catccatttt aggagctgaa cttgacttca gccctttct atcctgaagt tccttcattc    5040
ctcatcccct ccaaatctcc cacttaaacg tctagaagac cacgctacct gcagtcagac    5100
ccagatctca ataactactc atgcttattc tccgatccaa tctcttggat ggtgaccata    5160
```

| gtattaatta ctttcctctc aactaaagcc tcttttttgcc cctaatctca ctagcttgat | 5220 |
| aaacagaaaa tctgacactg tatgccacgt caactgataa tgagacctct ccattttctc | 5280 |
| aagattttct gaactgactt taaccccta catgaaaacc tgtgtcttac acataaaaaa | 5340 |
| agatgagaaa agtgtactta cgtttcagct ccagcttggt cccagcaccg aacgtcgacc | 5400 |
| tcgagggggg gcccggtacc caattcgccc tatagtgagt cgtattacgc gcgc | 5454 |

```
<210> SEQ ID NO 2
<211> LENGTH: 11
<212> TYPE: PRT
<213> ORGANISM: Artificial Sequence
<220> FEATURE:
<223> OTHER INFORMATION: J5 domain of HEA125

<400> SEQUENCE: 2

Arg Lys Leu Glu Leu Lys Thr Gly Ala Gly Phe
1               5                   10

<210> SEQ ID NO 3
<211> LENGTH: 8791
<212> TYPE: DNA
<213> ORGANISM: Artificial Sequence
<220> FEATURE:
<223> OTHER INFORMATION: humanization of constant IgG1-CH1, CH2 and CH3
      domains

<400> SEQUENCE: 3
```

| gacggccagt gagcgcgcgt aatacgactc actatagggc gaattgggta ccgggccccc | 60 |
| cctcgaggtc gacaaccaca gaagagcagg agctaattgg cacggggtgg ggtgcatgct | 120 |
| gggtactcat agggaagctg ggataagtag tagttgggga ttctaagcag tcacagagaa | 180 |
| actgatccag gtgagagtac ggggtacaca gctgagcaaa tactcatag ctggagctga | 240 |
| tgggtgtata aggtaccagg ctgagcagct gaaggtaacc tggagctagt gggggtgtgg | 300 |
| gagaccaggc tgagcagcta ccaaggatca gggatagaca tgtaagcagt caagctcagc | 360 |
| tactacatga gagctggagc tagtatgaag gtggaggtcc agttgagtgt ctttagagaa | 420 |
| actgaggcaa gtgggagtgc agagatccaa gctgagcagc tccagcttag ctggtatagg | 480 |
| tgacaggacg ggggataaca aggctaagaa cacacagaga gcagggtctc ctgggtaggt | 540 |
| tacaggtcaa gctgagtag aagcaggga gctgaggttg ggagtaatgc agaattccag | 600 |
| acttagcagt ccaggcaaac taaaccagtg ggagtgtggg agtcctaact gaacaaatac | 660 |
| caggcatatg aagctgataa gtgtgtatag agtaccaagc tgagcagcta caggagagct | 720 |
| gggatagcta tgtggggaga ccaggttaag caaacagtgg agagcaagat aaagtcttaa | 780 |
| tgtaggcatc caggctgaat agacacaggg gagctgagga aggtagtact agaggattct | 840 |
| aggcttagaa gtcacaggga aactgaggcc tgggtgaggg tggacatcct agctggaaaa | 900 |
| atcaccaggg agctggagct gatgggtata aaaggtacc aggttgagca gctacaggag | 960 |
| agctaggaca tgtggggatg tttttgttcca ggctgaacaa ctgtagagca tcaggggag | 1020 |
| gtggaacttt aagaagtcag gctgagcagc tacaggagag ctgcagctat cggtatgtg | 1080 |
| gaggtccagc cagagcagct acagggtagc tgggataaat gggctggag aaccaggcta | 1140 |
| agaagacaca ggggagcagg ttctagtctg cataggagtg gggatccagg tcgaatacac | 1200 |
| acagaagaga aaagggtagg tagaaatgga ggattctaga ctcagctata actgagtggt | 1260 |
| agtgtgagtg ttctagctga aaaaaaaaaa aataccatga agctgagct gatgggtata | 1320 |
| aaaggaacca gcctgagcaa ctgtagggta tctggggtgg atggggatgt ggggagtcat | 1380 |

```
gctgagctgc tacaagggca gtgtggcctc taggagtgta ggggaccaag ctgagcatct   1440
acagggaaac tggagtgtag ggctccagaa tgagcaactg caggtcagct gaggccggta   1500
agagtgtggg gaaccagact ggacagttag ttgcaagtta gccagagtag gtgagagttc   1560
tattagagaa gcctcagcag aatgggaagt gggaactagg aaaccaggat gagcacctac   1620
aacagaagtg aggcaggtta gggtgtaggg gatgagctgt gcagctactg tggagcacgc   1680
agactggagt agaagaggtt ctggctgaac acttgaaggg aaccaggtag gcaggaggca   1740
gtgtgtacag acagctgaat gagacatcat gcaaggccag ttccctgccc tgagctacat   1800
tagctgggac cagggccagc ggttgaggaa ccaggcagag gtgaaatggt ggtgtgatag   1860
gaaggcaatg gcagagggga aggagaagtt atgcttatgt catgctggaa tgtaggaagg   1920
ggaaagagcc aggatgtcta ggctggagct gatccggctg tctgctctga tggcagcaac   1980
aggcctgagc ttctctggac tcaagaagcc agggcaacaa aataaagggg gcctagcaga   2040
gcaaagacac tgctagcact gggatcagga aaacaggaca agactcccga tccaggaggt   2100
catgggaggg aaggagaaga ctacagggga ctgtccttgg gaaagagtaa gggcccactg   2160
gagggagtgc tcaggaagca agcccattga caggggagaa caaggctggg ggacgtctgg   2220
atgggcagta ggcagcccca gtcccagga gggagagaaa aggcagatag gaaaacaggt   2280
caggtttagc agaggcctac tgaagtactc tcctcaggac agaaccctga atactggaaa   2340
atgcggaact gctgcaggca caaagaatag ctgaggtcta agagtaaaac agactagggg   2400
atgagaggac ctcaggaaga gcctttggct gagcaggaac aagaacaggg gaaatcctag   2460
ggctgacatt gccagtggaa acatacaggc tggagctctt tagtcaggag ctccagctgt   2520
gatctagaca ccaggcagga agatcaaatc tgtcccaaca atacagggga cagaggctca   2580
acctagagtg tgagcatcac gggctgtgca ggagatttca gagctcaggt gcagcagaga   2640
ctagcatggc cctggggata aagggaagga tccaagggac aaggggataa tcctggggag   2700
gtaagggcca gcttcgtgac agaaggtggt agtgtccaac ttcaagagcc ctgtgctact   2760
taaaaaaaaa aaaaaaaaaa aaggaaaggg acttctctgt gtttggcaac acaagtgcga   2820
tgcacaggca ggaagatcaa atctgtccca acaatacagg ggacagaggc tcaacctaca   2880
aacggaaaga acctggggca gtgtgaagac aacactgtag aagtcaaggc tgagttcact   2940
gaactctcgt tagtgagact acacagcaag gaggtggcgg gcactgagca gtgaggcccc   3000
gggaagtggg ggtgatggtg gtgactgtta agaactgggg gaaagaattg tggagaacca   3060
agctaaaaag ttatgtcaaa ccacatgttt aggagcctgg gttgacttca tagggagtag   3120
gtatggaggc taatctagag gtttgtgtat aggcaagaag tgaatcctga cccaagaata   3180
gagagtgcta aacggactta gctcaaagac aactgaaaaa gacaatgcct gcaaaacaaa   3240
gctaaggcca gagctcttgg actatgaaga gttcagggaa cctaagaaca gggaccatct   3300
gtgtacaggc caaggccggt agaagcagcc taggaaatgt caagagccaa cgtggatggg   3360
tgggcaaaga caggaaggga ctgttaggct gcagggatgt gccgacttca atttgtgctt   3420
cagtgttgtc cagattgtgt gcagccatat ggcccaggta taagaagttt aacagtggaa   3480
cacagatgcc cacatcagac agctgggggg tgggggggg gaacacagat acccatactg   3540
gaaagcaggt ggggcatttt cctaggaacg ggactgggct caatggcctc aggtctcatc   3600
tggtctggtg atcctgacat tgacaggccc aaatgttgga tcccaagctt atccccatga   3660
gcccagacac tggacgctga acctcgcgga cagttaagaa cccaggggcc tctgcgccct   3720
```

```
gggcccagct ctgtcccaca ccgcggtcac atggcaccac ctctcttgca gcctccacca     3780
agggcccatc ggtcttcccc ctggcaccct cctccaagag cacctctggg ggcacagcgg     3840
ccctgggctg cctggtcaag gactacttcc ccgaaccggt gacggtgtcg tggaactcag     3900
gcgccctgac cagcggcgtg cacaccttcc cggctgtcct acagtcctca ggactctact     3960
ccctcagcag cgtggtgacc gtgccctcca gcagcttggg cacccagacc tacatctgca     4020
acgtgaatca caagcccagc aacaccaagg tggacaagaa agttggtgag aggccagcac     4080
agggagggag ggtgtctgct ggaagccagg ctcagcgctc ctgcctggac gcatcccggc     4140
tatgcagccc cagtccaggg cagcaaggca ggccccgtct gcctcttcac ccggaggcct     4200
ctgcccgccc cactcatgct cagggagagg gtcttctggc ttttccccca ggctctgggc     4260
aggcacaggc taggtgcccc taacccaggc cctgcacaca aggggcagg tgctgggctc      4320
agacctgcca agagccatat ccgggaggac cctgccctg acctaagccc accccaaagg      4380
ccaaactctc cactccctca gctcggacac cttctctcct cccagattcc agtaactccc     4440
aatcttctct ctgcagagcc caaatcttgt gacaaaactc acacatgccc accgtgccca     4500
ggtaagccag cccaggcctc gccctccagc tcaaggcggg acaggtgccc tagagtagcc     4560
tgcatccagg gacaggcccc agccgggtgc tgacacgtcc acctccatct cttcctcagc     4620
acctgaactc ctggggggac cgtcagtctt cctcttcccc ccaaaaccca aggacaccct     4680
catgatctcc cggacccctg aggtcacatg cgtggtggtg gacgtgagcc acgaagaccc     4740
tgaggtcaag ttcaactggt acgtggacgg cgtggaggtg cataatgcca agacaaagcc     4800
gcggaggag cagttacaac agcacgtacc gtgtggtcag cgtcctcacc gtcctgcacc      4860
aggactggct gaatggcaag gagtacaagt gcaaggtctc caacaaagcc ctcccagccc     4920
ccatcgagaa aaccatctcc aaagccaaag gtgggacccg tggggtgcga gggccacatg     4980
gacagaggcc ggctcggccc accctctgcc ctgagagtga ccgctgtacc aacctctgtc     5040
cctacagggc agccccgaga accacaggtg tacaccctgc ccccatcccg ggatgagctg     5100
accaagaacc aggtcagcct gacctgcctg gtcaaaggct tctatcccag cgacatcgcc     5160
gtggagtggg agagcaatgg gcagccggag aacaactaca agaccacgcc tcccgtgctg     5220
gactccgacg gctccttctt cctctacagc aagctcaccg tggacaagag caggtggcag     5280
caggggaacg tcttctcatg ctccgtgatg catgaggctc tgcacaacca ctacacgcag     5340
aagagcctct ccctgtctcc gggtaaatga gtgcgacggc cggcaagccc ccgctccccg     5400
ggctctcgcg gtcgcacgag gatgcttggc acgtaccccc tgtacatact cccgggcgc     5460
ccagcatgga aataaagcac ccagcgctgc cctgggcccc tgcgagactg tgatggttct     5520
ttccacgggt caggccgagt ctgaggcctg agtggcatga gggaggcaga gcgggtccca     5580
ctgtcccac actggaagct tgggccacag cttgcagaca gacctttgcc atctctccgc      5640
tcagctttcc agaggctaag tctagcccgt atggtgatga tgcagggagc tctatgctat     5700
ctcagtgtta tcagactcct aagtggagga tcaacatggt cccattaaaa ccaacctgct     5760
cagcaacacc ctgccaataa ggcccgtatg tgaaaatgtg cacacatcta cacatgcaca     5820
ggcacacaca cacacacatg catgggcaca cacacataca gagagagaga atcacagaaa     5880
ctcccatgag catcctatac agtactcaaa gataaaaagg taccaggtct acccacatga     5940
tcatcctcgg catttacaag tgggccaact gatacagata aaactttct atgccaagga      6000
cgccaacaac cttcctcata tacacaagtc cgctcatgac aaatctgtcc ctgaacctca     6060
gactggcgcc cgtgactcac acagtggaca ctcctccaaa gctgtatagc ttccttact      6120
```

```
tccctgtgtg tactttctct gaagtacact catcacacag aagaggccct gtgattactc    6180
tggccctctg ttcttggtca tcagagaata gacagaagat caggcaaact acacagacac    6240
ttcccacaat catcacaggc cctgactctg ctctccagtc tcaaaactga aggctggagc    6300
acacagaaat aagctcctac acagcccaga ccagtatcgg gtccagtgtg tctgaatgag    6360
cccagggaca aaatggcagc actttgggga actgagattt ctggtccaag aaggagagat    6420
ggaggcccag ggagggtctg ctgacccagc ccagcccagc cagctgcag ctttctcctg     6480 ggcctccatg cagcttcctg ccacacaggg aatggcccta gccccacctt attgggacaa    6540
acactgaccg ccctctctgt ccagggctgc aactggacga acctgtgct gaggcccagg     6600 acggggagct ggacgggctc tggacgacca tcaccatctt catcagcctc ttcctgctca    6660
gcgtgtgcta cagcgctgct gtcacactct caaggtcag ccatactgtc cccacagtgt     6720
ctacaatgtc ctcatactct tccccatact gtccctgtgg tgacctatac cccacactgt    6780
cccatgctaa tgaccacagt cttacatgct atgtaatgct gtctacccett ctgtatgcac    6840 agtctcacaa tgtcccatgc agtctccacg atgctccatg ctgccccttg ttccacgcta    6900
tgctgtccca tgctattgtc tgtatttca tgctcttttc acactgtccc tagtgtcaca     6960
ttctgcccat gttgtccacc acattgtccc cactctgcac acagcctcac actgtaccct    7020 gctaccgat aatgttccct gttgtcccca actctctccc tgcatcattt gtcaactgtc     7080
ccctgaattc ccatgttgtt cccacactgt tagtgtgtaa tgtgctctgt cccaggtgta    7140
ccttgttccg tgctgtctca cttcatcgcc cattctgtcc tttactaac cccactctat     7200 caccacactg tccctatgca ctgcccacat tgtcctcata ctgtcccatt ttgtatcttc    7260
atcctgtccc catagtgtcc aatgatctac cccacactat tcccacttca tgcccctaca    7320
atttccctat tccatccctc tctggtcacc atgccatcct tcccactcct gcacagctgg    7380
agagggactc ccgggatgag tccttgccca gatgagctac ctatctagag gagtcttcag    7440
gtgggaaggg aatgcagtct tgatcttggt cttattcacc ctgtctcaca ggtaaagtgg    7500
atcttctcct cggtggtgga gctgaagcag acactggttc ctgaatacaa gaacatgatt    7560
gggcaagcgc cctaggccac ctcttgtaat ggcagggat ttcccaggcc ccaaaggacc     7620
ctgtccaata tgccaagcag cacaactgag atcacactgt ctgctcatct cgctttcctc    7680
cgaccccgag actcagctac tctcaaattt tccctctctg aaggaccatg tggacattac    7740
attgctccag gccacagcca ccaggaccta aaacaccatc acagcagcac caaagacact    7800
ggatagaccc acaagagcaa tagcttcctc aacagtatat ccaaactgtt gggacaaacg    7860
agcaatcact gaagaagtga caagttccca caatgtcagt gtccagctga aaggggcaa     7920 aaagtggtac cagccctgtc cacaccacct tctaattcac aggaatccgt gatagaagag    7980
gcaggttgta gatccgaaag atgagacaga ttttatcaac tccagaaaga gctgggccca    8040
actgaatcta actgaattat tctagcgacc ttggcattgc catgacctgc catgaccttc    8100
ctccttagca cttcgatgaa ccctgggata tggaaaatgc ctgtgtttct cagggtttgg    8160
gaagaaccat ccatgttggg attcttgtgt agatcctcct cctggtcaca gatgcaatac    8220
actggatttt caggcaaagg agcaaattca cagacaactc tggccctaca gtcctcagac    8280
ctagacacca ccatctcctt ggaattatca aatctaacac ccggcacaca acaaagaagg    8340
actgggactt tgaggccttt gtgtagccct agaggggca gaggccactg agcagggatt     8400
gggtgatcag caaggacctc ctggagaggg acctgaggag caggttccaa ttgggccaaa    8460
```

-continued

```
gaaagaagaa gaacaataga ggtgaaggat gctggaaaga gccatggtac agcagtcttg    8520
tccttcagac atgactctta cagcccagga ctcttacagt agctagctgg agcagaagtc    8580
caagggatta ccatgcccta gggccacagg ctactggagg gtggagtgag tctactacac    8640
aggtccaatg cctgtttctc catcgtttct cagccaatga gaaatcagag tctccaaaca    8700
ggaagaaaaa ggacggccgc accgcggtgg agctccagct tttgttccct ttagtgaggg    8760
ttaattgcgc gcttggcgta atcatggtca t                                    8791
```

```
<210> SEQ ID NO 4
<211> LENGTH: 44
<212> TYPE: PRT
<213> ORGANISM: Mus musculus

<400> SEQUENCE: 4

Gly Leu Gln Leu Asp Glu Thr Cys Ala Glu Ala Gln Asp Gly Glu Leu
1               5                   10                  15

Asp Gly Leu Trp Thr Thr Ile Thr Ile Phe Ile Ser Leu Phe Leu Leu
            20                  25                  30

Ser Val Cys Tyr Ser Ala Ala Val Thr Leu Phe Lys
        35                  40

<210> SEQ ID NO 5
<211> LENGTH: 107
<212> TYPE: PRT
<213> ORGANISM: Homo sapiens

<400> SEQUENCE: 5

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 6
<211> LENGTH: 97
<212> TYPE: PRT
<213> ORGANISM: Homo Sapiens

<400> SEQUENCE: 6

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
```

```
                    65                  70                  75                  80
Ile Cys Asn Val Asn His Lys Pro Ser Asn Thr Lys Val Asp Lys Lys
                    85                  90                  95
Val
```

<210> SEQ ID NO 7
<211> LENGTH: 4106
<212> TYPE: DNA
<213> ORGANISM: Artificial Sequence
<220> FEATURE:
<223> OTHER INFORMATION: chimeric mouse DNA
<220> FEATURE:
<221> NAME/KEY: misc_feature
<222> LOCATION: (937)..(937)
<223> OTHER INFORMATION: n is a, c, t, or g
<220> FEATURE:
<221> NAME/KEY: misc_feature
<222> LOCATION: (3367)..(3367)
<223> OTHER INFORMATION: n is a, c, t, or g
<220> FEATURE:
<221> NAME/KEY: misc_feature
<222> LOCATION: (3627)..(3627)
<223> OTHER INFORMATION: n is a, c, t, or g

<400> SEQUENCE: 7

| | | | | | |
|---|---|---|---|---|---|
| tacgccaagc | gcgcaattaa | ccctcactaa | agggaacaaa | agctggagct | ccaccgcggt | 60 |
| ggcggccgca | gcttggttat | atggaccaca | tgacaggaac | aactgtttct | tttaatggaa | 120 |
| ctgataaaaa | atttctctcc | tgatctagac | tgctgtggtc | ttttaagtag | catgaaaaac | 180 |
| atctgctaaa | gaaggaatta | gtttgaacat | gctagaaata | catctgtgat | actcttcatc | 240 |
| actcttgttg | gaaagatatg | caagaagcac | tatttggcta | ttatttggaa | agtgctataa | 300 |
| tgtattttga | tatcttaacc | tctgaaattc | ttctgtatgt | tggcagattg | taaactttta | 360 |
| taaggctttc | attctcttct | ctggagaaat | atgtctttgt | aggcaatcca | gaatttctta | 420 |
| tttctcgcta | atgaaatctc | ctcagtgtga | tatcacttta | gtttcatgtg | ttgtcatgct | 480 |
| tcatgtaatg | ttaagaaagt | taaagatgct | ccaatccata | ttgtaagaaa | cattccaagc | 540 |
| cctggaataa | ggcatggatt | tgagatgctc | tttatttcaa | actactgaat | atatcttaga | 600 |
| gatttcttta | gactgtgtta | aatatgtaac | catttaagta | ggagtcaagt | ctcctttaaa | 660 |
| tctcaacagc | tcttcaggta | accaacaaaa | ggataaatat | tctaataagt | cactaggagc | 720 |
| atgctcttct | gaccaggtct | ttcttataag | caacatgaag | acagtatgat | ttgcataagt | 780 |
| ttttctttct | tctaatgtcc | ctgcctctta | gagtattata | agaagatctt | tctcagggat | 840 |
| gtgtcatggt | ccacacaaac | tcagggaaag | tttgaagatg | gtatccacac | ctcagttcct | 900 |
| tgtatttttg | ctttttctgga | ttccamtvas | rthrrgnhva | hhtrrggtat | gactgtctgg | 960 |
| gtgtggcaaa | aaagtggaga | tgttatttga | agttcctatt | ctctagaaag | tataggaact | 1020 |
| tcgacgtcct | tttcccaagg | cagtctggag | catgcgcttt | agcagcccg | ctgggcactt | 1080 |
| ggcgctacac | aagtggcctc | tggctcgcac | acattccaca | tccaccggta | ggcgccaacc | 1140 |
| ggctccgttc | tttggtggcc | ccttcgcgcc | accttctact | cctcccctag | tcaggaagtt | 1200 |
| cccccccgcc | ccgcagctcg | cgtcgtgcag | gacgtgacaa | atggaagtag | cacgtctcac | 1260 |
| tagtctcgtg | cagatggaca | gcaccgctga | gcaatggaag | cgggtaggcc | tttggggcag | 1320 |
| cggccaatag | cagctttgct | ccttcgcttt | ctgggctcag | aggctgggaa | ggggtgggtc | 1380 |
| cggggggcggg | ctcaggggcg | ggctcagggg | cgggcgggc | gcccgaaggt | cctccggagg | 1440 |
| cccggcattc | tgcacgcttc | aaaagcgcac | gtctgccgcg | ctgttctcct | cttcctcatc | 1500 |

```
tccgggcctt tcgacctgca gcccggtgga cagcaagcga accggaattg ccagctgggg   1560
cgccctctgg taaggttggg aagccctgca aagtaaactg gatggctttc ttgccgccaa   1620
ggatctgatg gcgcagggga tcaagatctg atcaagagac aggatgagga tcgtttcgca   1680
tgattgaaca agatggattg cacgcaggtt ctccggccgc ttgggtggag aggctattcg   1740
gctatgactg ggcacaacag acaatcggct gctctgatgc cgccgtgttc cggctgtcag   1800
cgcaggggcg cccggttctt tttgtcaaga ccgacctgtc cggtgccctg aatgaactgc   1860
aggacgaggc agcgcggcta tcgtggctgg ccacgacggg cgttccttgc gcagctgtgc   1920
tcgacgttgt cactgaagcg ggaagggact ggctgctatt gggcgaagtg ccggggcagg   1980
atctcctgtc atctcacctt gctcctgccg agaaagtatc catcatggct gatgcaatgc   2040
ggcggctgca tacgcttgat ccggctacct gcccattcga ccaccaagcg aaacatcgca   2100
tcgagcgagc acgtactcgg atggaagccg gtcttgtcga tcaggatgat ctggacgaag   2160
agcatcaggg gctcgcgcca gccgaactgt tcgccaggct caaggcgcgc atgcccgacg   2220
gcgaggatct cgtcgtgacc catggcgatg cctgcttgcc gaatatcatg gtggaaaatg   2280
gccgcttttc tggattcatc gactgtggcc ggctgggtgt ggcggaccgc tatcaggaca   2340
tagcgttggc tacccgtgat attgctgaag agcttggcgg cgaatgggct gaccgcttcc   2400
tcgtgcttta cggtatcgcc gctcccgatt cgcagcgcat cgccttctat cgccttcttg   2460
acgagttctt ctgagacgtc gaagttccta ttcttcaaat agtataggaa cttcggtctc   2520
attatcagtt gacgtggcat acagtgtcag attttctgtt tatcaagcta gtgagattag   2580
gggcaaaaag aggctttagt tgagaggaaa gtaattaata ctatggtcac catccaagag   2640
attggatcgg agaataagca tgagtagtta ttgagatctg gtctgactg caggtagcgt    2700
ggtcttctag acgtttaagt gggagatttg gaggggatga ggaatgaagg aacttcagga   2760
tagaaaaggg ctgaagtcaa gttcagctcc taaaatggat gtgggagcaa actttgaaga   2820
taaactgaat gacccagagg atgaaacagc gcagatcaaa gaggggcctg gagctctgag   2880
aagagaagga gactcatccg tgttgagttt ccacaagtac tgtcttgagt tttgcaataa   2940
aagtgggata gcagagttga gtgagccgta ggctgagttc tctcttttgt ctcctaagtt   3000
tttatgacta caaaaatcag tagtatgtcc tgaataatc attaagctgt ttgaaagtat    3060
gactgcttgc catgtagata ccatggcttg ctgaataatc agaagaggtg tgactcttat   3120
tctaaaattt gtcacaaaat gtcaaaatga gagactctgt aggaacgagt ccttgacaga   3180
cagctcaagg ggtttttttc cttttgtctca tttctacatg aaagtaaatt tgaaatgatc   3240
tttttttatta aagagtaga aatacagttg ggttttgaact gtatgtttta atggccacgg   3300
ttttgtaaga catttggtcc tttgttttcc cagttattac tcgattgtaa ttttatatcg   3360
ccagcantgg actgaaacgg tccgcaacct cttctttaca actgggtgac ctcgcggctg   3420
tgccagccat ttggcgttca ccctgccgct aagggccatg tgaaccccg cggtagcatc     3480
ccttgctccg cgtggaccac tttcctgagg cacagtgata ggaacagagc cactaatctg   3540
aagagaacag agatgtgaca gactacacta atgtgagaaa acaaggaaa gggtgactta    3600
ttggagattt cagaaataaa atgcahndtt tattattata ttcccttatt ttaattttct   3660
attagggaat tagaaagggc ataaactgct ttatccagtg ttatattaaa agcttaatgt   3720
atataatctt ttagaggtaa aatctacagc cagcaaaagt catggtaaat attctttgac   3780
tgaactctca ctaaactcct ctaaattata tgtcatatta actggttaaa ttaatataaa   3840
tttgtgacat gaccttaact ggttaggtag gatattttc ttcatgcaaa aatatgacta    3900
```

| ataataattt agcacaaaaa tatttcccaa tactttaatt ctgtgataga aaaatgttta | 3960 |
| actcagctac tataatccca taattttgaa aactatttat tagcttttgt gtttgaccct | 4020 |
| tccctagcca aaggcaacta tttaaggacc ctttagggcc cggtaccccca attcgcccta | 4080 |
| tagtgagtcg tattacgcgc gctcac | 4106 |

```
<210> SEQ ID NO 8
<211> LENGTH: 16
<212> TYPE: PRT
<213> ORGANISM: Artificial Sequence
<220> FEATURE:
<223> OTHER INFORMATION: Mouse-vKappa-Leader-Exon

<400> SEQUENCE: 8
```

Met Val Ser Thr Pro Gln Phe Leu Val Phe Leu Leu Phe Trp Ile Pro
1               5                   10                  15

```
<210> SEQ ID NO 9
<211> LENGTH: 4430
<212> TYPE: DNA
<213> ORGANISM: Artificial Sequence
<220> FEATURE:
<223> OTHER INFORMATION: pBs MKappaG418M
<220> FEATURE:
<221> NAME/KEY: misc_feature
<222> LOCATION: (1334)..(1334)
<223> OTHER INFORMATION: n is a, c, g, or t
<220> FEATURE:
<221> NAME/KEY: misc_feature
<222> LOCATION: (1348)..(1348)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t

<400> SEQUENCE: 9
```

| acgccaagcg cgcaattaac cctcactaaa gggaacaaaa gctggagctc caccgcggtg | 60 |
| gcggccgcag gcctgggcta acacacatgg atgatatgta ctagatgatg tatacacatg | 120 |
| tggatgatat gtacaagatt atgtaaacac acatggatga tacatacatg aagatgtata | 180 |
| cacacataga tgatatgtac gagatggtac gtacacacat ggatgatatg taccaaatga | 240 |
| tgtatataca cggggatgat atgtacgaga tgatgtatac acgtggat gatatgtacg | 300 |
| agatatgtac acacatggat gatatgtacg agatgatgtg tacacacatg gatgatatat | 360 |
| acaagatgat gtacacacac gtggatgata tgtatgagat ggtacataca ctcatggatg | 420 |
| atatgtacga gatgatatgt acacacatgg atgatatgta cgagatgatg tgaacacaca | 480 |
| tggatgatat gtacgagatg atgtgtaaac acatggatga tatgtatgag atgatgtgta | 540 |
| cacacatgga tgatatgtac gagatgatgt gtacacacat ggatgatatg tacgagatga | 600 |
| tgtgtacaca aatggatgat aagtacgaga tgatgtgtac acacatggat gatatgtacg | 660 |
| aaatgatacc tacacacatg gatgatatgt acgagaggat gtgtacacac ttggatgtta | 720 |
| tgtaccagat gatgtataca cacgtggatg atatgtacga gatggtacgt acactcatgg | 780 |
| atgatatgta tgagatgata tgtacacaca tggatgatat gtatgagatg atgtgtacac | 840 |
| acatggatga tatatacgag atgatgtgta cacacatgga tgatatgtac gagatgatgt | 900 |
| gtacacaaat ggatgataag tacgagatga tgtgtacaca catggatgat atgtacgaaa | 960 |
| tgataccctac acatggat gatatgtacg agaggatgtg tacacacttg gatgttatgt | 1020 |
| acaagatgat gtatacacac gtggatgata tgtacgagat ggtacgtaca ctcatggatg | 1080 |

```
atatgtatga gatgatatgt acacacatgg atgatatgta tgagatgatg tgtacacaca    1140
tggatgatat atacgagatg atgtgtacac acatggatga tatgtacgag atgatgtgta    1200
cacacatgga tgatatgtat gaaatgatac ctacacacat ggatatgtac gagatgatgt    1260
gtaccacaca tggatgatat ctatgagata aatgctgagc tacagagctg attgatgttc    1320
agctagtcag tctntccatg ttatagtngg canactacta agggtctcct tgtttctagt    1380
gaacaaccaa gttagtgtgt aggggaatgg gaactgaaaa taaatcataa cacaagaaat    1440
tcaggctcct gcatacacac aggtctgtag aaggcttagc caaactcagg aatgtagtca    1500
tgtcacatga ctttaacaca gaaatcggat ctccaacctc aaaaggcagc agcacacagg    1560
gctggatctg attcagaaag tgttgtatcc atcaaggttg aaaccctcat cataggcctg    1620
gctcatatag aaaacagctc cagagcaggt aacaaactga tgcccactgc caccct taat    1680 tctgcccatg taaacataac actaaaattc attttt gatt taaaaaataa attaaataga    1740
taataattag tgtttacaaa aaatcttagt atgatattaa aaattacaac catttttgtt    1800
actgccagaa tccttgagta catttaaata acttcgtata atgtatgcta tacgaagtta    1860
tgacgtcctt ttcccaaggc agtctggagc atgcgcttta gcagccccgc tgggcacttg    1920
gcgctacaca agtggcctct ggctcgcaca cattccacat ccaccggtag gcgccaaccg    1980
gctccgttct ttggtggccc cttcgcgcca ccttctactc ctcccctagt caggaagttc    2040 cccccgccc cgcagctcgc gtcgtgcagg acgtgacaaa tggaagtagc acgtctcact    2100
agtctcgtgc agatggacag caccgctgag caatggaagc gggtaggcct ttggggcagc    2160
ggccaatagc agctttgctc cttcgctttc tgggctcaga ggctgggaag gggtgggtcc    2220
gggggcgggc tcaggggcgg gctcaggggc ggggcgggcg cccgaaggtc ctccggaggc    2280
ccggcattct gcacgcttca aaagcgcacg tctgccgcgc tgttctcctc ttcctcatct    2340
ccgggccttt cgacctgcag cccggtggac agcaagcgaa ccggaattgc cagctggggc    2400
gccctctggt aaggttggga agccctgcaa agtaaactgg atggctttct tgccgccaag    2460
gatctgatgg cgcaggggat caagatctga tcaagagaca ggatgaggat cgtttcgcat    2520
gattgaacaa gatggattgc acgcaggttc tccggccgct tgggtggaga ggctattcgg    2580
ctatgactgg gcacaacaga caatcggctg ctctgatgcc gccgtgttcc ggctgtcagc    2640
gcaggggcgc ccgttctttt tgtcaagac cgacctgtcc ggtgccctga atgaactgca    2700
ggacgaggca gcgcggctat cgtggctggc cacgacgggc gttccttgcg cagctgtgct    2760
cgacgttgtc actgaagcgg gaagggactg gctgctattg ggcgaagtgc cggggcagga    2820
tctcctgtca tctcaccttg ctcctgccga aaagtatcc atcatggctg atgcaatgcg    2880
gcggctgcat acgcttgatc cggctacctg cccattcgac caccaagcga acatcgcat    2940 cgagcgagca cgtactcgga tggaagccgg tcttgtcgat caggatgatc tggacgaaga    3000
gcatcagggg ctcgcgccag ccgaactgtt cgccaggctc aaggcgcgca tgcccgacgg    3060
cgaggatctc gtcgtgaccc atggcgatgc ctgcttgccg aatatcatgg tggaaaatgg    3120
ccgcttttct ggattcatcg actgtggccg gctgggtgtg gcggaccgct atcaggacat    3180
agcgttggct acccgtgata ttgctgaaga gcttggcggc gaatgggctg accgcttcct    3240
cgtgctttac ggtatcgccg ctcccgattc gcagcgcatc gccttctatc gccttcttga    3300
cgagttcttc tgagacgtca taacttcgta taatgtatac tatacgaagt tatccttagg    3360
gagccggctg agagaagttg ggaaataaac tgtctaggga tctcagagcc tttaggacag    3420
```

```
attatctcca catctttgca aaaacttaga atctgtgtga tggtgttggt ggagtccgta    3480
gttggagatt ttcagttttt agaataaaag tattaactgc ggagtatact tcaggaccac    3540
ctctgtgaca gcatttatac agtatccgat gcataggggc aaagagtgga gtggggcact    3600
ttctttagat ttgtgaggaa tgttccacac tagattgttt aaaacttcat ttgttggaag    3660
gagaggtgtc ttagtgattg agtcaaggga gaaaggcatc tagcctcggt ctcaaaaggg    3720
tagttgctgt ctagagaggt ctggtggagc ctgcaaaagt ccagctttca aaggaacaca    3780
gaagtatgtg tatggaatat tagaagatgt tgctttttact cttaagttgg ttcctaggaa    3840
aaatagttaa atactgtgac tttaaaatgt gagagggttt tcaagtactc attttttttaa    3900 atgtccaaaa tttttgtcaa tcaatttgag gtcttgtttg tgtagaactg acattactta    3960
aagtttaacc gaggaatggg agtgaggctc tctcataccc tattcagaac tgacttttaa    4020
caatgataaa ttaggtttca aatattttta aatgaactga gcaatgttga gttggagtca    4080
agatgaccga tcagaaccag aacacctgca gcagctggca ggaagcaggt catgtggcaa    4140
ggctatttgg ggaagggaaa ataaaaccac taggaaaact tgtggctgtg gtttgaagag    4200
gtggttttga aacactctgt ccagccccac caaaccgaaa gtccaggctg agcaaaacac    4260
cacctgggta atttgcattt ctaaaataag ttgaggattc agccgaaact ggagaggtcc    4320 tctttttaact tattgagttc aaccttttaa ttttagcttg agtagttcta gtttccccag    4380
ggcccggtac cccaattcgc cctatagtga gtcgtattac gcgcgctcac              4430

<210> SEQ ID NO 10
<211> LENGTH: 695
<212> TYPE: DNA
<213> ORGANISM: Artificial Sequence
<220> FEATURE:
<223> OTHER INFORMATION: Vector pBs FRTVKappa

<400> SEQUENCE: 10
tacgccaagc gcgcgaagtt cctattctct agaaagtata ggaacttcga cgtcaaatac      60
aaaattttct tgctttattt ggaagccaat gtcacatggg aattgacttt cagtttaaag     120
aacttgatac aataaaagtc atttattttt ctaagttgtt tagaagtgac tttcatattc     180
agtgttgtga tctactcatg tctcttctct ttttccagcc tccagaggtg acatcttgct     240
gactcagtct ccagccatcc tgtctgtgag tccaggagaa agagtcagtt ctcctgcag     300 ggccagtcag agcattggca taagtttaca ctggtatcag caaagaccaa gtgattctcc     360
aaggcttctc ataaagtatg cttctgagtc aatctctggg atcccttcca ggtttagtgg     420
cagtggatca gggacagatt ttactcttag catcaacagt gtggagtctg aagatattgc     480
agattattac tgtcaacaaa gtaatatctg gccaaccacg ttcggtgctg gaccaagct     540 ggagctgaaa cgtaagtaca cttttctcat cttttttat gtgtaagaca caggttttca     600
tgttaggggt taaagtcagt tcagaaaatc ttgagaaaat ggagagacgt cgaagttcct     660
attcttcaaa tagtatagga acttcgcgcg ctcac                               695

<210> SEQ ID NO 11
<211> LENGTH: 112
<212> TYPE: PRT
<213> ORGANISM: Artificial Sequence
<220> FEATURE:
<223> OTHER INFORMATION: vKappa-Exon

<400> SEQUENCE: 11

Ala Ser Arg Gly Asp Ile Leu Leu Thr Gln Ser Pro Ala Ile Leu Ser
```

```
            1               5                  10                 15
Val Ser Pro Gly Glu Arg Val Ser Phe Ser Cys Arg Ala Ser Gln Ser
            20                 25                 30

Ile Gly Ile Ser Leu His Trp Tyr Gln Gln Arg Pro Ser Asp Ser Pro
            35                 40                 45

Arg Leu Leu Ile Lys Tyr Ala Ser Glu Ser Ile Ser Gly Ile Pro Ser
 50                 55                 60

Arg Phe Ser Gly Ser Gly Ser Gly Thr Asp Phe Thr Leu Ser Ile Asn
 65                 70                 75                 80

Ser Val Glu Ser Glu Asp Ile Ala Asp Tyr Tyr Cys Gln Gln Ser Asn
                85                 90                 95

Ile Trp Pro Thr Thr Phe Gly Ala Gly Thr Lys Leu Glu Leu Lys Arg
                100                105                110
```

<210> SEQ ID NO 12
<211> LENGTH: 890
<212> TYPE: DNA
<213> ORGANISM: Artificial Sequence
<220> FEATURE:
<223> OTHER INFORMATION: Vector pBs loxPVH

<400> SEQUENCE: 12

```
tacgccaagc gcgcataact tcgtataatg tatgctatac gaagttatga cgtcaacctc      60
agaggatttg tcatctctag gcctgctcag tagaggttgc tatatagcag ggaaacatgc     120
aaataaggcc tctctcttct catgaaaacg agtcctgaac taaccttgaa tctgaagcaa     180
aggggatcag cccgagattc tcattcagtg atcaacactg aacacacatc ccttaccatg     240
gattttgggc tgattttttt tattgttgct cttttaaaag gtaattcatg gaaagagat      300
actgagtgtg ttactggtca tgagcaagat agatggtgag cctgtatggc agtttgctga     360
cagaattctc tgtgttttca ggggtccagt gtgaagtgaa gcttctcgag tctggaggtg     420
gcctggtgca gcctggagga tccctgaaac tctcctgtgc agcctcagga ttcgatttta     480
gtagattctg gatgacttgg gtccggcagg ctccagggaa agggctagaa tggattggag     540
aaattaatct agatagcagt acgataaact atacgccatc tctaaaggat aaattcatca     600
tctccaggga caacgccaaa aatacgctgt tcctgcaaat gagcaaagtg agatctgagg     660
acacagccct ttattactgt tcaagagaac aaaagctgat ctcagaagaa gatctagact     720
actggggtca gggaacctca gtcaccgtct cctcaggtaa gaatggcctc tccaggtctt     780
tatttttaac ctttgttatg gaattttctg agcattgcag actaatctta aatgtttgtc     840
gacgtcataa cttcgtataa tgtatactat acgaagttat gcgcgctcac              890
```

<210> SEQ ID NO 13
<211> LENGTH: 140
<212> TYPE: PRT
<213> ORGANISM: Artificial Sequence
<220> FEATURE:
<223> OTHER INFORMATION: Leader-Exon

<400> SEQUENCE: 13

```
Met Asp Phe Gly Leu Ile Phe Phe Ile Val Ala Leu Leu Lys Gly Val
 1               5                  10                 15

Gln Cys Glu Val Lys Leu Leu Glu Ser Gly Gly Gly Leu Val Gln Pro
                20                 25                 30

Gly Gly Ser Leu Lys Leu Ser Cys Ala Ala Ser Gly Phe Asp Phe Ser
            35                 40                 45
```

```
Arg Phe Trp Met Thr Trp Val Arg Gln Ala Pro Gly Lys Gly Leu Glu
 50                  55                  60
Trp Ile Gly Glu Ile Asn Leu Asp Ser Ser Thr Ile Asn Tyr Thr Pro
 65                  70                  75                  80
Ser Leu Lys Asp Lys Phe Ile Ile Ser Arg Asp Asn Ala Lys Asn Thr
                 85                  90                  95
Leu Phe Leu Gln Met Ser Lys Val Arg Ser Glu Asp Thr Ala Leu Tyr
                100                 105                 110
Tyr Cys Ser Arg Glu Gln Lys Leu Ile Ser Glu Glu Asp Leu Asp Tyr
            115                 120                 125
Trp Gly Gln Gly Thr Ser Val Thr Val Ser Ser Gly
            130                 135                 140

<210> SEQ ID NO 14
<211> LENGTH: 130
<212> TYPE: DNA
<213> ORGANISM: Artificial Sequence
<220> FEATURE:
<223> OTHER INFORMATION: cloning vector pBS FRTklon

<400> SEQUENCE: 14
tacgccaagc gcgcgaagtt cctattctct agaaagtata ggaacttcga cgtcacgcgt      60
aatgtcgact atgcggccgc gacgtcgaag ttcctattct caaatagta taggaacttc     120 gcgcgctcac                                                           130

<210> SEQ ID NO 15
<211> LENGTH: 129
<212> TYPE: DNA
<213> ORGANISM: Artificial Sequence
<220> FEATURE:
<223> OTHER INFORMATION: cloning vector pBS loxPklon

<400> SEQUENCE: 15
tacgccaagc gcgcataact tcgtataatg tatgctatac gaagttatga cgtccgcgta      60
atgtcgacta tgcggccgcg acgtcataac ttcgtataat gtatactata cgaagttatg     120
cgcgctcac                                                            129

<210> SEQ ID NO 16
<211> LENGTH: 4367
<212> TYPE: DNA
<213> ORGANISM: Artificial Sequence
<220> FEATURE:
<223> OTHER INFORMATION: vector pBS loxP-IgG1

<400> SEQUENCE: 16
tacgccaagc gcgcgaagtt cctattctct agaaagtata ggaacttcga cgtcataact      60
tcgtataatg tatgctatac gaagttatac gcgtataact tcgtataatg tatactatac     120
gaagttatgg atccatcccc atgagccagg acactggacg ctgaacctcg cggacagtta     180
agaacccagg ggcctctgcg ccctgggccc agctctgtcc cacaccgcgg tcacatggca     240
ccacctctct tgcagcctcc accaagggcc catcggtctt ccccctggca cctcctcca      300 agagcacctc tgggggcaca gcggccctgg gctgcctggt caaggactac ttccccgaac     360
cggtgacggt gtcgtggaac tcaggcgccc tgaccagcgg cgtgcacacc ttcccggctg     420
tcctacagtc ctcaggactc tactccctca gcagcgtggt gaccgtgccc tccagcagct     480
tgggcaccca gacctacatc tgcaacgtga atcacaagcc cagcaacacc aaggtggaca     540
agaaagttgg tgagaggcca gcacagggag ggagggtgtc tgctggaagc caggctcagc     600
```

```
gctcctgcct ggacgcatcc cggctatgca gccccagtcc agggcagcaa ggcaggcccc      660
gtctgcctct tcacccggag gcctctgccc gccccactca tgctcaggga gagggtcttc      720 tggcttttc cccaggctct gggcaggcac aggctaggtg ccctaaccc aggccctgca        780 cacaaagggg caggtgctgg gctcagacct gccaagagcc atatccggga ggaccctgcc      840
cctgacctaa gcccacccca aaggccaaac tctccactcc ctcagctcgg acaccttctc      900
tcctcccaga ttccagtaac tcccaatctt ctctctgcag agcccaaatc ttgtgacaaa      960
actcacacat gcccaccgtg cccaggtaag ccagcccagg cctcgccctc cagctcaagg     1020
cgggacaggt gccctagagt agcctgcatc cagggacagg ccccagccgg gtgctgacac     1080
gtccacctcc atctcttcct cagcacctga actcctgggg ggaccgtcag tcttcctctt     1140
ccccccaaaa cccaaggaca ccctcatgat ctcccggacc cctgaggtca catgcgtggt     1200
ggtggacgtg agccacgaag accctgaggt caagttcaac tggtacgtgg acggcgtgga     1260
ggtgcataat gccaagacaa agccgcggga ggagcagtac aacagcacgt accgtgtggt     1320
cagcgtcctc accgtcctgc accaggactg gctgaatggc aaggagtaca gtgcaaggt     1380 ctccaacaaa gccctcccag cccccatcga gaaaaccatc tccaaagcca aaggtgggac     1440
ccgtggggtg cgagggccac atggacagag gccggctcgg cccaccctct gccctgagag     1500
tgaccgctgt accaacctct gtccctacag ggcagcccg agaaccacag gtgtacaccc      1560
tgcccccatc ccgggatgag ctgaccaaga accaggtcag cctgacctgc ctggtcaaag     1620
gcttctatcc cagcgacatc gccgtggagt gggagagcaa tgggcagccg gagaacaact     1680
acaagaccac gcctcccgtg ctggactccg acggctcctt cttcctctac agcaagctca     1740
ccgtggacaa gagcaggtgg cagcagggga acgtcttctc atgctccgtg atgcatgagg     1800
ctctgcacaa ccactacacg cagaagagcc tctccctgtc tccgggtaaa tgagtgcgac     1860
ggccggcaag cccccgctcc ccgggctctc gcggtcgcac gaggatgctt ggcacgtacc     1920
ccctgtacat acttcccggg cgcccagcat ggaaataaag cacccagcgc tgccctgggc     1980
ccctgcgaga ctgtgatggt tctttccacg ggtcaggccg agtctgaggc ctgagtggca     2040
tgagggaggc agagcgggtc ccactgtccc cacactggaa gcttgggcca cagcttgcag     2100
acagaccttt gccatctctc cgctcagctt tccagaggct aagtctagcc cgtatggtga     2160
tgatgcaggg agctctatgc tatctcagtg ttatcagact cctaagtgga ggatcaacat     2220
ggtcccatta aaaccaacct gctcagcaac accctgccaa taaggcccgt atgtgaaaat     2280
gtgcacacat ctacacatgc acaggcacac acacacacac atgcatgggc acacacacat     2340
acagagagag agaatcacag aaactcccat gagcatccta tacagtactc aaagataaaa     2400
aggtaccagg tctacccaca tgatcatcct cggcatttac aagtgggcca actgatacag     2460
ataaaacttt tctatgccaa ggacgccaac aaccttcctc atatacacaa gtccgctcat     2520
gacaaatctg tccctgaacc tcagactggc gccgtgact cacacagtgg acactcctcc      2580
aaagctgtat agcttccttt acttccctgt gtgtactttc tctgaagtac actcatcaca     2640
cagaagaggc cctgtgatta ctctggccct ctgttcttgg tcatcagaga atagacagaa     2700
gatcaggcaa actacacaga cacttcccac aatcatcaca ggccctgact ctgctctcca     2760
gtctcaaaac tgaaggctgg agcacacaga aataagctcc tacacagccc agaccagtat     2820
cgggtccagt gtgtctgaat gagcccaggg acaaaatggc agcactttgg ggaactgaga     2880
tttctggtcc aagaaggaga gatggaggcc cagggagggt ctgctgaccc agcccagccc     2940
```

| | | |
|---|---|---|
| agcccagctg cagctttctc ctgggcctcc atgcagcttc ctgccacaca gggaatggcc | 3000 |
| ctagccccac cttattggga caaacactga ccgccctctc tgtccaggqc tgcaactgga | 3060 |
| cgagacctgt gctgaggccc aggacgggga gctggacggg ctctggacga ccatcaccat | 3120 |
| cttcatcagc ctcttcctgc tcagcgtgtg ctacagcgct gctgtcacac tcttcaaggt | 3180 |
| cagccatact gtccccacag tgtctacaat gtcctcatac tcttccccat actgtccctg | 3240 |
| tggtgaccta ccccacac tgtcccatgc taatgaccac agtcttacat gctatgtaat | 3300 |
| gctgtctacc cttctgtatg cacagtctca caatgtccca tgcagtctcc acgatgctcc | 3360 |
| atgctgcccc ttgttccacg ctatgctgtc ccatgctatt gtctgtattt tcatgctctt | 3420 |
| ttcacactgt ccctagtgtc acattctgcc catgttgtcc accacattgt ccccactctg | 3480 |
| cacacagcct cacactgtac cctgctaccc gataatgttc cctgttgtcc ccaactctct | 3540 |
| ccctgcatca tttgtcaact gtccctgaa ttcccatgtt gttcccacac tgttagtgtg | 3600 |
| taatgtgctc tgtcccaggt gtaccttgtt ccgtgctgtc tcacttcatc gcccattctg | 3660 |
| tcctttact aaccccactc tatcaccaca ctgtccctat gcactgccca cattgtcctc | 3720 |
| atactgtccc attttgtatc ttcatcctgt ccccatagtg tccaatgatc taccccacac | 3780 |
| tattcccact tcatgcccct acaatttccc tattccatcc ctctctggtc accatgccat | 3840 |
| ccttcccact cctgcacagc tggagaggga ctcccgggat gagtccttgc ccagatgagc | 3900 |
| tacctatcta gaggagtctt caggtgggaa gggaatgcag tcttgatctt ggtcttattc | 3960 |
| accctgtctc acaggtaaag tggatcttct cctcggtggt ggagctgaag cagacactgg | 4020 |
| ttcctgaata caagaacatg attgggcaag cgccctaggc cacctcttgt aatggcaggg | 4080 |
| gatttcccag gccccaaagg accctgtcca atatgccaag cagcacaact gagatcacac | 4140 |
| tgtctgctca tctcgctttc ctccgacccc gagactcagc tactctcaaa ttttccctct | 4200 |
| ctgaaggacc atgtggacat tacattgctc caggccacag ccaccaggac ctaaaacacc | 4260 |
| atcacagcag caccaaagac actggataga cccacaagag caatagcttc cggatccgac | 4320 |
| gtcgaagttc ctattcttca aatagtatag gaacttcgcg cgctcac | 4367 |

<210> SEQ ID NO 17
<211> LENGTH: 15
<212> TYPE: PRT
<213> ORGANISM: Homo sapiens

<400> SEQUENCE: 17

Glu Pro Lys Ser Cys Asp Lys Thr His Thr Cys Pro Pro Cys Pro
1               5                   10                  15

<210> SEQ ID NO 18
<211> LENGTH: 110
<212> TYPE: PRT
<213> ORGANISM: Homo sapiens

<400> SEQUENCE: 18

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asn Val Ser His Glu Asp Pro Glu Val Lys Phe Asn Trp Tyr
            35                  40                  45

Val Asn Gly Val Glu Val His Asn Ala Lys Thr Lys Pro Arg Glu Glu
        50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 19
<211> LENGTH: 27
<212> TYPE: PRT
<213> ORGANISM: Mus musculus

<400> SEQUENCE: 19

Val Lys Trp Ile Phe Ser Ser Val Val Glu Leu Lys Gln Thr Leu Val
 1               5                  10                  15

Pro Glu Tyr Lys Asn Met Ile Gly Gln Ala Pro
             20                  25

<210> SEQ ID NO 20
<211> LENGTH: 1906
<212> TYPE: DNA
<213> ORGANISM: Artificial Sequence
<220> FEATURE:
<223> OTHER INFORMATION: vector pBS FRT KappaHEAscFv215

<400> SEQUENCE: 20
```

| | | | | | |
|---|---|---|---|---|---|
| tacgccaagc | gcgcgaagtt | cctattctct | agaaagtata | ggaacttcga | cgtcaaatac | 60 |
| aaaattttct | tgctttattt | ggaagccaat | gtcacatggg | aattgacttt | cagtttaaag | 120 |
| aacttgatac | aataaaagtc | atttattttt | ctaagttgtt | tagaagtgac | tttcatattc | 180 |
| agtgttgtga | tctactcatg | tctcttctct | ttttccagcc | tccagaggtg | acatcttgct | 240 |
| gactcagtct | ccagccatcc | tgtctgtgag | tccaggagaa | agagtcagtt | ctcctgcag | 300 |
| ggccagtcag | agcattggca | taagtttaca | ctggtatcag | caaagaccaa | gtgattctcc | 360 |
| aaggcttctc | ataaagtatg | cttctgagtc | aatctctggg | atcccttcca | ggtttagtgg | 420 |
| cagtggatca | gggacagatt | ttactcttag | catcaacagt | gtggagtctg | aagatattgc | 480 |
| agattattac | tgtcaacaaa | gtaatatctg | gccaaccacg | ttcggtgctg | ggaccaagct | 540 |
| ggagctgaaa | cgaactgtgg | ctgcaccatc | tgtcttcatc | ttcccgccat | ctgatgagca | 600 |
| gttgaaatct | ggaactgcct | ctgttgtgtg | cctgctgaat | aacttctatc | ccagagaggc | 660 |
| caaagtacag | tggaaggtgg | ataacgcccT | ccaatcgggt | aactcccagg | agagtgtcac | 720 |
| agagcaggac | agcaaggaca | gcacctacag | cctcagcagc | accctgacgc | tgagcaaagc | 780 |
| agactacgag | aaacacaaag | tctacgcctg | cgaagtcacc | catcagggcc | tgagctcgcc | 840 |
| cgtcacaaag | agcttcaaca | ggggagagtg | tgatgagccc | aaatcttctg | acaaaactca | 900 |
| cacatcccca | ccgtccccac | aagttcagct | gcagcagtct | ggggctgaac | tggtgaggcc | 960 |
| tggggtctca | gtgaagattt | cctgcaaggg | ttctggctac | aaattcactg | attatgctac | 1020 |
| gcactgggtg | aaacagagtc | atgcaaagag | tctagagtgg | attggagtta | ttagtactta | 1080 |
| ctatggtgat | actacttata | accagaagtt | caagggcaag | gccacaatga | ctgtcgacaa | 1140 |
| atcctccagc | acagcctata | tggaacttcc | cagactgaca | tctgatgatt | ctgccatcta | 1200 |
| ttattgtgcc | ctgttacgcc | cctttgctta | ctggggccaa | gggaccacgg | tcaccgtctc | 1260 |
| ctcaggtgga | ggcggttcag | gcggaggtgg | ctctggcggt | ggcggatcgg | acatcgagct | 1320 |
| cactcagtct | ccatcctccc | tgagtgtgtc | agcaggagag | aaggtcacta | tgagctgcaa | 1380 |

```
gtccagtcag agtctgttaa acagtggaaa tcaaaataac gacttggcct ggtaccagca    1440
gaaaccaggg caacgtccta aactgttgat ctacggggca tccactaggg aatctggggt    1500
ccctgatcgc ttcacaggca gtggatctgg aaccgatttc actcttacca tcagcagtgt    1560
gcaggctgaa gacctggcag tttattactg tcagaatgat catagttatc cgttaacgtt    1620
cggtgctggc accaagctgg aaatcaaacg ggcggccgct ggatccgaac aaaagctgat    1680
ctcagaagaa gatctatccc atcatcacca tcatcattaa ctgcaaccac gttcggtgct    1740
gggaccaagc tggagctgaa acgtaagtac acttttctca tctttttta tgtgtaagac    1800 acaggttttc atgttagggg ttaaagtcag ttcagaaaat cttgagaaaa tggagagacg    1860
tcgaagttcc tattcttcaa atagtatagg aacttcgcgc gctcac                  1906
```

<210> SEQ ID NO 21
<211> LENGTH: 27
<212> TYPE: DNA
<213> ORGANISM: Artificial Sequence
<220> FEATURE:
<223> OTHER INFORMATION: chemically synthesized

<400> SEQUENCE: 21
aattatgtgt gttctctttc tcatctt                                           27

<210> SEQ ID NO 22
<211> LENGTH: 23
<212> TYPE: DNA
<213> ORGANISM: Artificial Sequence
<220> FEATURE:
<223> OTHER INFORMATION: chemically synthesized

<400> SEQUENCE: 22
catcctcctg ttgggtaatc cat                                               23

<210> SEQ ID NO 23
<211> LENGTH: 25
<212> TYPE: DNA
<213> ORGANISM: Artificial Sequence
<220> FEATURE:
<223> OTHER INFORMATION: chemically synthesized

<400> SEQUENCE: 23
gtggcatctg tgttttcttt ctcat                                             25

<210> SEQ ID NO 24
<211> LENGTH: 25
<212> TYPE: DNA
<213> ORGANISM: Artificial Sequence
<220> FEATURE:
<223> OTHER INFORMATION: chemically synthesized

<400> SEQUENCE: 24
tgtgtcgtcc atgtgtcatg tattt                                             25

<210> SEQ ID NO 25
<211> LENGTH: 23
<212> TYPE: DNA
<213> ORGANISM: Artificial Sequence
<220> FEATURE:
<223> OTHER INFORMATION: chemically synthesized

<400> SEQUENCE: 25
ggtccacatg tcacctatct tct                                               23

```
<210> SEQ ID NO 26
<211> LENGTH: 25
<212> TYPE: DNA
<213> ORGANISM: Artificial Sequence
<220> FEATURE:
<223> OTHER INFORMATION: chemically synthesized

<400> SEQUENCE: 26
gtgtcgtttg tcttcccttt cttat                                          25

<210> SEQ ID NO 27
<211> LENGTH: 24
<212> TYPE: DNA
<213> ORGANISM: Artificial Sequence
<220> FEATURE:
<223> OTHER INFORMATION: chemically synthesized

<400> SEQUENCE: 27
atggacatct atcttctttc tcaa                                           24

<210> SEQ ID NO 28
<211> LENGTH: 25
<212> TYPE: DNA
<213> ORGANISM: Artificial Sequence
<220> FEATURE:
<223> OTHER INFORMATION: chemically synthesized

<400> SEQUENCE: 28
tgtcatttac cttcccttttc ttatc                                         25

<210> SEQ ID NO 29
<211> LENGTH: 25
<212> TYPE: DNA
<213> ORGANISM: Artificial Sequence
<220> FEATURE:
<223> OTHER INFORMATION: chemically synthesized

<400> SEQUENCE: 29
gtggcatctg tgttttcttt ctcat                                          25

<210> SEQ ID NO 30
<211> LENGTH: 25
<212> TYPE: DNA
<213> ORGANISM: Artificial Sequence
<220> FEATURE:
<223> OTHER INFORMATION: chemically synthesized

<400> SEQUENCE: 30
actgatcatg ttactatcac tggtc                                          25

<210> SEQ ID NO 31
<211> LENGTH: 21
<212> TYPE: DNA
<213> ORGANISM: Artificial Sequence
<220> FEATURE:
<223> OTHER INFORMATION: chemically synthesized

<400> SEQUENCE: 31
acgcccacac ctgagggctc a                                              21

<210> SEQ ID NO 32
<211> LENGTH: 21
<212> TYPE: DNA
<213> ORGANISM: Artificial Sequence
<220> FEATURE:
<223> OTHER INFORMATION: chemically synthesized
```

```
<400> SEQUENCE: 32
acccccacac ctgagggctc a                                              21

<210> SEQ ID NO 33
<211> LENGTH: 23
<212> TYPE: DNA
<213> ORGANISM: Artificial Sequence
<220> FEATURE:
<223> OTHER INFORMATION: chemically synthesized

<400> SEQUENCE: 33
tacagcctat tcctccagca tcc                                            23

<210> SEQ ID NO 34
<211> LENGTH: 21
<212> TYPE: DNA
<213> ORGANISM: Artificial Sequence
<220> FEATURE:
<223> OTHER INFORMATION: chemically synthesized

<400> SEQUENCE: 34
cagcccactc agaggcatcc c                                              21

<210> SEQ ID NO 35
<211> LENGTH: 21
<212> TYPE: DNA
<213> ORGANISM: Artificial Sequence
<220> FEATURE:
<223> OTHER INFORMATION: chemically synthesized

<400> SEQUENCE: 35
ctgccctctc ctccagcgtc c                                              21

<210> SEQ ID NO 36
<211> LENGTH: 22
<212> TYPE: DNA
<213> ORGANISM: Artificial Sequence
<220> FEATURE:
<223> OTHER INFORMATION: chemically synthesized

<400> SEQUENCE: 36
gccttcacct cagatgtccc ac                                             22

<210> SEQ ID NO 37
<211> LENGTH: 22
<212> TYPE: DNA
<213> ORGANISM: Artificial Sequence
<220> FEATURE:
<223> OTHER INFORMATION: chemically synthesized

<400> SEQUENCE: 37
tgccctctgt tcaggcatcc ca                                             22

<210> SEQ ID NO 38
<211> LENGTH: 21
<212> TYPE: DNA
<213> ORGANISM: Artificial Sequence
<220> FEATURE:
<223> OTHER INFORMATION: chemically synthesized

<400> SEQUENCE: 38
gggctcagtc ctctcctcag g                                              21

<210> SEQ ID NO 39
<211> LENGTH: 22
```

```
<212> TYPE: DNA
<213> ORGANISM: Artificial Sequence
<220> FEATURE:
<223> OTHER INFORMATION: chemically synthesized

<400> SEQUENCE: 39
cacagcctac tctgaggcat cc                                              22

<210> SEQ ID NO 40
<211> LENGTH: 21
<212> TYPE: DNA
<213> ORGANISM: Artificial Sequence
<220> FEATURE:
<223> OTHER INFORMATION: chemically synthesized

<400> SEQUENCE: 40
gtcctctcct caggtgtccc a                                               21

<210> SEQ ID NO 41
<211> LENGTH: 21
<212> TYPE: DNA
<213> ORGANISM: Artificial Sequence
<220> FEATURE:
<223> OTHER INFORMATION: chemically synthesized

<400> SEQUENCE: 41
cccggcctct cctcagatgt c                                               21

<210> SEQ ID NO 42
<211> LENGTH: 22
<212> TYPE: DNA
<213> ORGANISM: Artificial Sequence
<220> FEATURE:
<223> OTHER INFORMATION: chemically synthesized

<400> SEQUENCE: 42
tgccctctcc tcaggcatct ca                                              22

<210> SEQ ID NO 43
<211> LENGTH: 21
<212> TYPE: DNA
<213> ORGANISM: Artificial Sequence
<220> FEATURE:
<223> OTHER INFORMATION: chemically synthesized

<400> SEQUENCE: 43
cggcctctcc tcagatgtcc c                                               21

<210> SEQ ID NO 44
<211> LENGTH: 21
<212> TYPE: DNA
<213> ORGANISM: Artificial Sequence
<220> FEATURE:
<223> OTHER INFORMATION: chemically synthesized

<400> SEQUENCE: 44
gccttctcct caggcgtccc a                                               21

<210> SEQ ID NO 45
<211> LENGTH: 21
<212> TYPE: DNA
<213> ORGANISM: Artificial Sequence
<220> FEATURE:
<223> OTHER INFORMATION: chemically synthesized

<400> SEQUENCE: 45
```
ccttctcgtc aggcgtccca g                                                21

<210> SEQ ID NO 46
<211> LENGTH: 22
<212> TYPE: DNA
<213> ORGANISM: Artificial Sequence
<220> FEATURE:
<223> OTHER INFORMATION: chemically synthesized

<400> SEQUENCE: 46
ccctgggtcc tgctctttct tc                                               22

<210> SEQ ID NO 47
<211> LENGTH: 23
<212> TYPE: DNA
<213> ORGANISM: Artificial Sequence
<220> FEATURE:
<223> OTHER INFORMATION: chemically synthesized

<400> SEQUENCE: 47
ccagggtgag cctaaaagac tgg                                              23

<210> SEQ ID NO 48
<211> LENGTH: 23
<212> TYPE: DNA
<213> ORGANISM: Artificial Sequence
<220> FEATURE:
<223> OTHER INFORMATION: chemically synthesized

<400> SEQUENCE: 48
tccagggaga gcctaaaaga ctg                                              23

<210> SEQ ID NO 49
<211> LENGTH: 23
<212> TYPE: DNA
<213> ORGANISM: Artificial Sequence
<220> FEATURE:
<223> OTHER INFORMATION: chemically synthesized

<400> SEQUENCE: 49
cccagggaga gtctaaaaga ctg                                              23

<210> SEQ ID NO 50
<211> LENGTH: 22
<212> TYPE: DNA
<213> ORGANISM: Artificial Sequence
<220> FEATURE:
<223> OTHER INFORMATION: chemically synthesized

<400> SEQUENCE: 50
ccagggtgag cccaaaagac tg                                               22

<210> SEQ ID NO 51
<211> LENGTH: 23
<212> TYPE: DNA
<213> ORGANISM: Artificial Sequence
<220> FEATURE:
<223> OTHER INFORMATION: chemically synthesized

<400> SEQUENCE: 51
tcccagggtg agctcaaaag act                                              23

<210> SEQ ID NO 52
<211> LENGTH: 21
<212> TYPE: DNA
<213> ORGANISM: Artificial Sequence

```
<220> FEATURE:
<223> OTHER INFORMATION: chemically synthesized

<400> SEQUENCE: 52
ccagggcgag cccaaaagac t                                        21

<210> SEQ ID NO 53
<211> LENGTH: 22
<212> TYPE: DNA
<213> ORGANISM: Artificial Sequence
<220> FEATURE:
<223> OTHER INFORMATION: chemically synthesized

<400> SEQUENCE: 53
cccagggcga gcccaaaaga ct                                       22

<210> SEQ ID NO 54
<211> LENGTH: 23
<212> TYPE: DNA
<213> ORGANISM: Artificial Sequence
<220> FEATURE:
<223> OTHER INFORMATION: chemically synthesized

<400> SEQUENCE: 54
gcctttttct gcatttgagg ttc                                      23

<210> SEQ ID NO 55
<211> LENGTH: 21
<212> TYPE: DNA
<213> ORGANISM: Artificial Sequence
<220> FEATURE:
<223> OTHER INFORMATION: chemically synthesized

<400> SEQUENCE: 55
ttgtagacct gagggccccg g                                        21

<210> SEQ ID NO 56
<211> LENGTH: 22
<212> TYPE: DNA
<213> ORGANISM: Artificial Sequence
<220> FEATURE:
<223> OTHER INFORMATION: chemically synthesized

<400> SEQUENCE: 56
agcctattcc tccagcgtcc ca                                       22

<210> SEQ ID NO 57
<211> LENGTH: 23
<212> TYPE: DNA
<213> ORGANISM: Artificial Sequence
<220> FEATURE:
<223> OTHER INFORMATION: chemically synthesized

<400> SEQUENCE: 57
cactatctcc aaaggcctct cac                                      23

<210> SEQ ID NO 58
<211> LENGTH: 22
<212> TYPE: DNA
<213> ORGANISM: Artificial Sequence
<220> FEATURE:
<223> OTHER INFORMATION: chemically synthesized

<400> SEQUENCE: 58
ccagcctctc ctcagatgtc cc                                       22
```

```
<210> SEQ ID NO 59
<211> LENGTH: 22
<212> TYPE: DNA
<213> ORGANISM: Artificial Sequence
<220> FEATURE:
<223> OTHER INFORMATION: chemically synthesized

<400> SEQUENCE: 59
ccagcctctc ctcagatgtc cc                                              22

<210> SEQ ID NO 60
<211> LENGTH: 21
<212> TYPE: DNA
<213> ORGANISM: Artificial Sequence
<220> FEATURE:
<223> OTHER INFORMATION: chemically synthesized

<400> SEQUENCE: 60
ggctcagtcc tctcctcagg t                                               21

<210> SEQ ID NO 61
<211> LENGTH: 25
<212> TYPE: DNA
<213> ORGANISM: Artificial Sequence
<220> FEATURE:
<223> OTHER INFORMATION: chemically synthesized

<400> SEQUENCE: 61
gcactataac atcagaaagc tggaa                                           25

<210> SEQ ID NO 62
<211> LENGTH: 22
<212> TYPE: DNA
<213> ORGANISM: Artificial Sequence
<220> FEATURE:
<223> OTHER INFORMATION: chemically synthesized

<400> SEQUENCE: 62
cagcccactc tgaggcatct gt                                              22

<210> SEQ ID NO 63
<211> LENGTH: 22
<212> TYPE: DNA
<213> ORGANISM: Artificial Sequence
<220> FEATURE:
<223> OTHER INFORMATION: chemically synthesized

<400> SEQUENCE: 63
agcctactcc tcaagggtcc ca                                              22

<210> SEQ ID NO 64
<211> LENGTH: 23
<212> TYPE: DNA
<213> ORGANISM: Artificial Sequence
<220> FEATURE:
<223> OTHER INFORMATION: chemically synthesized

<400> SEQUENCE: 64
aattgtgtcg tccgtgtgtc atg                                             23

<210> SEQ ID NO 65
<211> LENGTH: 22
<212> TYPE: DNA
<213> ORGANISM: Artificial Sequence
<220> FEATURE:
<223> OTHER INFORMATION: chemically synthesized
```

<400> SEQUENCE: 65
gagcacctgt ccccaagtct ga                                          22

<210> SEQ ID NO 66
<211> LENGTH: 20
<212> TYPE: DNA
<213> ORGANISM: Artificial Sequence
<220> FEATURE:
<223> OTHER INFORMATION: chemically synthesized

<400> SEQUENCE: 66
ccagacccag gccggctgca                                             20

<210> SEQ ID NO 67
<211> LENGTH: 22
<212> TYPE: DNA
<213> ORGANISM: Artificial Sequence
<220> FEATURE:
<223> OTHER INFORMATION: chemically synthesized

<400> SEQUENCE: 67
caaggagccc ccggacatta tc                                          22

<210> SEQ ID NO 68
<211> LENGTH: 23
<212> TYPE: DNA
<213> ORGANISM: Artificial Sequence
<220> FEATURE:
<223> OTHER INFORMATION: chemically synthesized

<400> SEQUENCE: 68
caggagaccc agcaccctta ttt                                         23

<210> SEQ ID NO 69
<211> LENGTH: 23
<212> TYPE: DNA
<213> ORGANISM: Artificial Sequence
<220> FEATURE:
<223> OTHER INFORMATION: chemically synthesized

<400> SEQUENCE: 69
aatgcctcca agactctgac cct                                         23

<210> SEQ ID NO 70
<211> LENGTH: 22
<212> TYPE: DNA
<213> ORGANISM: Artificial Sequence
<220> FEATURE:
<223> OTHER INFORMATION: chemically synthesized

<400> SEQUENCE: 70
aacatgcccc gaggaccaac ct                                          22

<210> SEQ ID NO 71
<211> LENGTH: 24
<212> TYPE: DNA
<213> ORGANISM: Artificial Sequence
<220> FEATURE:
<223> OTHER INFORMATION: chemically synthesized

<400> SEQUENCE: 71
cactaggaat ttactcagcc cagt                                        24

<210> SEQ ID NO 72

```
<211> LENGTH: 22
<212> TYPE: DNA
<213> ORGANISM: Artificial Sequence
<220> FEATURE:
<223> OTHER INFORMATION: chemically synthesized

<400> SEQUENCE: 72
gcagtttact cagcccaggg tg                                              22

<210> SEQ ID NO 73
<211> LENGTH: 20
<212> TYPE: DNA
<213> ORGANISM: Artificial Sequence
<220> FEATURE:
<223> OTHER INFORMATION: chemically synthesized

<400> SEQUENCE: 73
ggaatttact cagcccagtg                                                 20

<210> SEQ ID NO 74
<211> LENGTH: 24
<212> TYPE: DNA
<213> ORGANISM: Artificial Sequence
<220> FEATURE:
<223> OTHER INFORMATION: chemically synthesized

<400> SEQUENCE: 74
ctaggattat actcggtcag tgtg                                            24

<210> SEQ ID NO 75
<211> LENGTH: 22
<212> TYPE: DNA
<213> ORGANISM: Artificial Sequence
<220> FEATURE:
<223> OTHER INFORMATION: chemically synthesized

<400> SEQUENCE: 75
gcagtttact cagcccaggg tg                                              22

<210> SEQ ID NO 76
<211> LENGTH: 22
<212> TYPE: DNA
<213> ORGANISM: Artificial Sequence
<220> FEATURE:
<223> OTHER INFORMATION: chemically synthesized

<400> SEQUENCE: 76
ctcagcccag agtgctcagt ac                                              22

<210> SEQ ID NO 77
<211> LENGTH: 24
<212> TYPE: DNA
<213> ORGANISM: Artificial Sequence
<220> FEATURE:
<223> OTHER INFORMATION: chemically synthesized

<400> SEQUENCE: 77
attcagccag tgtagccact aatg                                            24

<210> SEQ ID NO 78
<211> LENGTH: 24
<212> TYPE: DNA
<213> ORGANISM: Artificial Sequence
<220> FEATURE:
<223> OTHER INFORMATION: chemically synthesized

<400> SEQUENCE: 78
```

```
cactaggaat tttctcagcc agtg                                                24
```

<210> SEQ ID NO 79
<211> LENGTH: 23
<212> TYPE: DNA
<213> ORGANISM: Artificial Sequence
<220> FEATURE:
<223> OTHER INFORMATION: chemically synthesized

<400> SEQUENCE: 79

```
ctcagccaat gtgctcagta cag                                                 23
```

<210> SEQ ID NO 80
<211> LENGTH: 25
<212> TYPE: DNA
<213> ORGANISM: Artificial Sequence
<220> FEATURE:
<223> OTHER INFORMATION: chemically synthesized

<400> SEQUENCE: 80

```
tactcggttc agtgtgctga gtact                                               25
```

<210> SEQ ID NO 81
<211> LENGTH: 22
<212> TYPE: DNA
<213> ORGANISM: Artificial Sequence
<220> FEATURE:
<223> OTHER INFORMATION: chemically synthesized

<400> SEQUENCE: 81

```
actcagccca gggtgctcag ta                                                  22
```

<210> SEQ ID NO 82
<211> LENGTH: 24
<212> TYPE: DNA
<213> ORGANISM: Artificial Sequence
<220> FEATURE:
<223> OTHER INFORMATION: chemically synthesized

<400> SEQUENCE: 82

```
cactaacagt ttactcagcc caga                                                24
```

<210> SEQ ID NO 83
<211> LENGTH: 22
<212> TYPE: DNA
<213> ORGANISM: Artificial Sequence
<220> FEATURE:
<223> OTHER INFORMATION: chemically synthesized

<400> SEQUENCE: 83

```
ctcagccagt gggctcagta ca                                                  22
```

<210> SEQ ID NO 84
<211> LENGTH: 24
<212> TYPE: DNA
<213> ORGANISM: Artificial Sequence
<220> FEATURE:
<223> OTHER INFORMATION: chemically synthesized

<400> SEQUENCE: 84

```
ggaatttact cagccagtgt gctc                                                24
```

<210> SEQ ID NO 85
<211> LENGTH: 23
<212> TYPE: DNA

<213> ORGANISM: Artificial Sequence
<220> FEATURE:
<223> OTHER INFORMATION: chemically synthesized

<400> SEQUENCE: 85
agcagtttac tcagcccagt gtg                23

<210> SEQ ID NO 86
<211> LENGTH: 24
<212> TYPE: DNA
<213> ORGANISM: Artificial Sequence
<220> FEATURE:
<223> OTHER INFORMATION: chemically synthesized

<400> SEQUENCE: 86
gaaagaggga atggtagagg aaac               24

<210> SEQ ID NO 87
<211> LENGTH: 24
<212> TYPE: DNA
<213> ORGANISM: Artificial Sequence
<220> FEATURE:
<223> OTHER INFORMATION: chemically synthesized

<400> SEQUENCE: 87
gaaatatgac gtctggtgct ctga               24

<210> SEQ ID NO 88
<211> LENGTH: 25
<212> TYPE: DNA
<213> ORGANISM: Artificial Sequence
<220> FEATURE:
<223> OTHER INFORMATION: chemically synthesized

<400> SEQUENCE: 88
aaaactccta aaagcagtgc tctga              25

<210> SEQ ID NO 89
<211> LENGTH: 23
<212> TYPE: DNA
<213> ORGANISM: Artificial Sequence
<220> FEATURE:
<223> OTHER INFORMATION: chemically synthesized

<400> SEQUENCE: 89
ctggggaaga ctgacacaga aag                23

<210> SEQ ID NO 90
<211> LENGTH: 23
<212> TYPE: DNA
<213> ORGANISM: Artificial Sequence
<220> FEATURE:
<223> OTHER INFORMATION: chemically synthesized

<400> SEQUENCE: 90
ggaacgatga ccagtgctct gat                23

<210> SEQ ID NO 91
<211> LENGTH: 24
<212> TYPE: DNA
<213> ORGANISM: Artificial Sequence
<220> FEATURE:
<223> OTHER INFORMATION: chemically synthesized

<400> SEQUENCE: 91
gagggaatgg tagaggaaac ttct               24

<210> SEQ ID NO 92
<211> LENGTH: 29
<212> TYPE: DNA
<213> ORGANISM: Artificial Sequence
<220> FEATURE:
<223> OTHER INFORMATION: chemically synthesized

<400> SEQUENCE: 92
aaaatataaa ggtctcttat actttacaa                                   29

<210> SEQ ID NO 93
<211> LENGTH: 25
<212> TYPE: DNA
<213> ORGANISM: Artificial Sequence
<220> FEATURE:
<223> OTHER INFORMATION: chemically synthesized

<400> SEQUENCE: 93
gcagtgctct gaataatatc ttgag                                       25

<210> SEQ ID NO 94
<211> LENGTH: 22
<212> TYPE: DNA
<213> ORGANISM: Artificial Sequence
<220> FEATURE:
<223> OTHER INFORMATION: chemically synthesized

<400> SEQUENCE: 94
tggtgtgggg tcttctggag ac                                          22

<210> SEQ ID NO 95
<211> LENGTH: 24
<212> TYPE: DNA
<213> ORGANISM: Artificial Sequence
<220> FEATURE:
<223> OTHER INFORMATION: chemically synthesized

<400> SEQUENCE: 95
atgaccagtg ctctgattaa gaac                                        24

<210> SEQ ID NO 96
<211> LENGTH: 22
<212> TYPE: DNA
<213> ORGANISM: Artificial Sequence
<220> FEATURE:
<223> OTHER INFORMATION: chemically synthesized

<400> SEQUENCE: 96
ctcttgccac ctctgctcag ca                                          22

<210> SEQ ID NO 97
<211> LENGTH: 21
<212> TYPE: DNA
<213> ORGANISM: Artificial Sequence
<220> FEATURE:
<223> OTHER INFORMATION: chemically synthesized

<400> SEQUENCE: 97
ctcctgccac ctctgctcag c                                           21

<210> SEQ ID NO 98
<211> LENGTH: 23
<212> TYPE: DNA
<213> ORGANISM: Artificial Sequence
<220> FEATURE:

<223> OTHER INFORMATION: chemically synthesized

<400> SEQUENCE: 98
agtcctgtta cctggcaact ctg                                        23

<210> SEQ ID NO 99
<211> LENGTH: 24
<212> TYPE: DNA
<213> ORGANISM: Artificial Sequence
<220> FEATURE:
<223> OTHER INFORMATION: chemically synthesized

<400> SEQUENCE: 99
actccatcag gagttttctc tgct                                       24

<210> SEQ ID NO 100
<211> LENGTH: 21
<212> TYPE: DNA
<213> ORGANISM: Artificial Sequence
<220> FEATURE:
<223> OTHER INFORMATION: chemically synthesized

<400> SEQUENCE: 100
ctcctgccac ctctgctcag c                                          21

<210> SEQ ID NO 101
<211> LENGTH: 21
<212> TYPE: DNA
<213> ORGANISM: Artificial Sequence
<220> FEATURE:
<223> OTHER INFORMATION: chemically synthesized

<400> SEQUENCE: 101
ctcctgccac ctctgctcag c                                          21

<210> SEQ ID NO 102
<211> LENGTH: 23
<212> TYPE: DNA
<213> ORGANISM: Artificial Sequence
<220> FEATURE:
<223> OTHER INFORMATION: chemically synthesized

<400> SEQUENCE: 102
caagtcctgt tacctggcaa ctc                                        23

<210> SEQ ID NO 103
<211> LENGTH: 27
<212> TYPE: DNA
<213> ORGANISM: Artificial Sequence
<220> FEATURE:
<223> OTHER INFORMATION: chemically synthesized

<400> SEQUENCE: 103
cagagtaata tctgtgtaga aataaaa                                    27

<210> SEQ ID NO 104
<211> LENGTH: 22
<212> TYPE: DNA
<213> ORGANISM: Artificial Sequence
<220> FEATURE:
<223> OTHER INFORMATION: chemically synthesized

<400> SEQUENCE: 104
tctcctctgt gccaccaagt cc                                         22

```
<210> SEQ ID NO 105
<211> LENGTH: 24
<212> TYPE: DNA
<213> ORGANISM: Artificial Sequence
<220> FEATURE:
<223> OTHER INFORMATION: chemically synthesized

<400> SEQUENCE: 105
gattgcagag tcaccttata gatc                                          24

<210> SEQ ID NO 106
<211> LENGTH: 24
<212> TYPE: DNA
<213> ORGANISM: Artificial Sequence
<220> FEATURE:
<223> OTHER INFORMATION: chemically synthesized

<400> SEQUENCE: 106
ccctggcatc cgactaatga aaat                                          24

<210> SEQ ID NO 107
<211> LENGTH: 24
<212> TYPE: DNA
<213> ORGANISM: Artificial Sequence
<220> FEATURE:
<223> OTHER INFORMATION: chemically synthesized

<400> SEQUENCE: 107
gggtgaccag gtttattcaa ccaa                                          24

<210> SEQ ID NO 108
<211> LENGTH: 24
<212> TYPE: DNA
<213> ORGANISM: Artificial Sequence
<220> FEATURE:
<223> OTHER INFORMATION: chemically synthesized

<400> SEQUENCE: 108
ggtactcttt ggaattgacc tgag                                          24

<210> SEQ ID NO 109
<211> LENGTH: 26
<212> TYPE: DNA
<213> ORGANISM: Artificial Sequence
<220> FEATURE:
<223> OTHER INFORMATION: chemically synthesized

<400> SEQUENCE: 109
ccaatcttta ccaaactcct atttga                                        26

<210> SEQ ID NO 110
<211> LENGTH: 20
<212> TYPE: DNA
<213> ORGANISM: Artificial Sequence
<220> FEATURE:
<223> OTHER INFORMATION: chemically synthesized

<400> SEQUENCE: 110
ccacaggacc tctgggctga                                               20

<210> SEQ ID NO 111
<211> LENGTH: 21
<212> TYPE: DNA
<213> ORGANISM: Artificial Sequence
<220> FEATURE:
<223> OTHER INFORMATION: chemically synthesized
```

```
<400> SEQUENCE: 111
ggcttcaggg acctctgggc t                                              21

<210> SEQ ID NO 112
<211> LENGTH: 21
<212> TYPE: DNA
<213> ORGANISM: Artificial Sequence
<220> FEATURE:
<223> OTHER INFORMATION: chemically synthesized

<400> SEQUENCE: 112
ggcttcgggg acctctgggc t                                              21

<210> SEQ ID NO 113
<211> LENGTH: 22
<212> TYPE: DNA
<213> ORGANISM: Artificial Sequence
<220> FEATURE:
<223> OTHER INFORMATION: chemically synthesized

<400> SEQUENCE: 113
ggaaatggcc ttggggacct ct                                             22

<210> SEQ ID NO 114
<211> LENGTH: 21
<212> TYPE: DNA
<213> ORGANISM: Artificial Sequence
<220> FEATURE:
<223> OTHER INFORMATION: chemically synthesized

<400> SEQUENCE: 114
agagaggccc tgggaagccc a                                              21

<210> SEQ ID NO 115
<211> LENGTH: 22
<212> TYPE: DNA
<213> ORGANISM: Artificial Sequence
<220> FEATURE:
<223> OTHER INFORMATION: chemically synthesized

<400> SEQUENCE: 115
ggccctggga agcctatgga tt                                             22

<210> SEQ ID NO 116
<211> LENGTH: 20
<212> TYPE: DNA
<213> ORGANISM: Artificial Sequence
<220> FEATURE:
<223> OTHER INFORMATION: chemically synthesized

<400> SEQUENCE: 116
ccctgggaag cccatggggc                                                20

<210> SEQ ID NO 117
<211> LENGTH: 20
<212> TYPE: DNA
<213> ORGANISM: Artificial Sequence
<220> FEATURE:
<223> OTHER INFORMATION: chemically synthesized

<400> SEQUENCE: 117
gatcgagggg agggtccctg                                                20

<210> SEQ ID NO 118
<211> LENGTH: 21
```

```
<212> TYPE: DNA
<213> ORGANISM: Artificial Sequence
<220> FEATURE:
<223> OTHER INFORMATION: chemically synthesized

<400> SEQUENCE: 118
gaggggtcca ggaagcccat g                                              21

<210> SEQ ID NO 119
<211> LENGTH: 20
<212> TYPE: DNA
<213> ORGANISM: Artificial Sequence
<220> FEATURE:
<223> OTHER INFORMATION: chemically synthesized

<400> SEQUENCE: 119
tggatgggct cggcggggct                                                20

<210> SEQ ID NO 120
<211> LENGTH: 19
<212> TYPE: DNA
<213> ORGANISM: Artificial Sequence
<220> FEATURE:
<223> OTHER INFORMATION: chemically synthesized

<400> SEQUENCE: 120 gcaggggggag gggctgctg                                                19

<210> SEQ ID NO 121
<211> LENGTH: 21
<212> TYPE: DNA
<213> ORGANISM: Artificial Sequence
<220> FEATURE:
<223> OTHER INFORMATION: chemically synthesized

<400> SEQUENCE: 121
tgccccaggc tcagtgccca t                                              21

<210> SEQ ID NO 122
<211> LENGTH: 22
<212> TYPE: DNA
<213> ORGANISM: Artificial Sequence
<220> FEATURE:
<223> OTHER INFORMATION: chemically synthesized

<400> SEQUENCE: 122
ccaggctcag tccccacaga tt                                             22

<210> SEQ ID NO 123
<211> LENGTH: 24
<212> TYPE: DNA
<213> ORGANISM: Artificial Sequence
<220> FEATURE:
<223> OTHER INFORMATION: chemically synthesized

<400> SEQUENCE: 123
ctcaacccca tattatcatg ctag                                           24

<210> SEQ ID NO 124
<211> LENGTH: 23
<212> TYPE: DNA
<213> ORGANISM: Artificial Sequence
<220> FEATURE:
<223> OTHER INFORMATION: chemically synthesized

<400> SEQUENCE: 124
```

```
gctggggctg attgcagggg ata                                             23

<210> SEQ ID NO 125
<211> LENGTH: 20
<212> TYPE: DNA
<213> ORGANISM: Artificial Sequence
<220> FEATURE:
<223> OTHER INFORMATION: chemically synthesized

<400> SEQUENCE: 125
ccagaccctg ccccaggctc                                                 20

<210> SEQ ID NO 126
<211> LENGTH: 22
<212> TYPE: DNA
<213> ORGANISM: Artificial Sequence
<220> FEATURE:
<223> OTHER INFORMATION: chemically synthesized

<400> SEQUENCE: 126
actctatccc tggggaccca ca                                              22

<210> SEQ ID NO 127
<211> LENGTH: 21
<212> TYPE: DNA
<213> ORGANISM: Artificial Sequence
<220> FEATURE:
<223> OTHER INFORMATION: chemically synthesized

<400> SEQUENCE: 127
cctcagagat cagggccagc c                                               21

<210> SEQ ID NO 128
<211> LENGTH: 22
<212> TYPE: DNA
<213> ORGANISM: Artificial Sequence
<220> FEATURE:
<223> OTHER INFORMATION: chemically synthesized

<400> SEQUENCE: 128
gggtcagcca cacagcctga tt                                              22

<210> SEQ ID NO 129
<211> LENGTH: 23
<212> TYPE: DNA
<213> ORGANISM: Artificial Sequence
<220> FEATURE:
<223> OTHER INFORMATION: chemically synthesized

<400> SEQUENCE: 129
gagtctcagt gtccaaccta cac                                             23

<210> SEQ ID NO 130
<211> LENGTH: 24
<212> TYPE: DNA
<213> ORGANISM: Artificial Sequence
<220> FEATURE:
<223> OTHER INFORMATION: chemically synthesized

<400> SEQUENCE: 130
cccagggaat tcagggaaat gttt                                            24

<210> SEQ ID NO 131
<211> LENGTH: 21
<212> TYPE: DNA
<213> ORGANISM: Artificial Sequence
```

```
<220> FEATURE:
<223> OTHER INFORMATION: chemically synthesized

<400> SEQUENCE: 131
ccccaaaggg acccccacct c                                      21

<210> SEQ ID NO 132
<211> LENGTH: 22
<212> TYPE: DNA
<213> ORGANISM: Artificial Sequence
<220> FEATURE:
<223> OTHER INFORMATION: chemically synthesized

<400> SEQUENCE: 132
gaccctcagc atcctcatgc cc                                     22

<210> SEQ ID NO 133
<211> LENGTH: 21
<212> TYPE: DNA
<213> ORGANISM: Artificial Sequence
<220> FEATURE:
<223> OTHER INFORMATION: chemically synthesized

<400> SEQUENCE: 133
ccacagggac ctctgggctg a                                      21

<210> SEQ ID NO 134
<211> LENGTH: 21
<212> TYPE: DNA
<213> ORGANISM: Artificial Sequence
<220> FEATURE:
<223> OTHER INFORMATION: chemically synthesized

<400> SEQUENCE: 134
cagaggggag gaagccccag a                                      21

<210> SEQ ID NO 135
<211> LENGTH: 24
<212> TYPE: DNA
<213> ORGANISM: Artificial Sequence
<220> FEATURE:
<223> OTHER INFORMATION: chemically synthesized

<400> SEQUENCE: 135
gctgaccaca agttgagaca agat                                   24

<210> SEQ ID NO 136
<211> LENGTH: 24
<212> TYPE: DNA
<213> ORGANISM: Artificial Sequence
<220> FEATURE:
<223> OTHER INFORMATION: chemically synthesized

<400> SEQUENCE: 136
gctgaccaca agttgagaca agat                                   24

<210> SEQ ID NO 137
<211> LENGTH: 22
<212> TYPE: DNA
<213> ORGANISM: Artificial Sequence
<220> FEATURE:
<223> OTHER INFORMATION: chemically synthesized

<400> SEQUENCE: 137
gcttagacct tagccttcga ca                                     22
```

```
<210> SEQ ID NO 138
<211> LENGTH: 500
<212> TYPE: PRT
<213> ORGANISM: Homo sapiens

<400> SEQUENCE: 138

Ala Ser Arg Gly Asp Ile Leu Leu Thr Gln Ser Pro Ala Ile Leu Ser
1               5                   10                  15

Val Ser Pro Gly Glu Arg Val Ser Phe Ser Cys Arg Ala Ser Gln Ser
                20                  25                  30

Ile Gly Ile Ser Leu His Trp Tyr Gln Gln Arg Pro Ser Asp Ser Pro
            35                  40                  45

Arg Leu Leu Ile Lys Tyr Ala Ser Glu Ser Ile Ser Gly Ile Pro Ser
50                  55                  60

Arg Phe Ser Gly Ser Gly Ser Gly Thr Asp Phe Thr Leu Ser Ile Asn
65                  70                  75                  80

Ser Val Glu Ser Glu Asp Ile Ala Asp Tyr Tyr Cys Gln Gln Ser Asn
                85                  90                  95

Ile Trp Pro Thr Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Glu Pro Lys Ser Ser
210                 215                 220

Asp Lys Thr His Thr Ser Pro Pro Ser Pro Gln Val Gln Leu Gln Gln
225                 230                 235                 240

Ser Gly Ala Glu Leu Val Arg Pro Gly Val Ser Val Lys Ile Ser Cys
                245                 250                 255

Lys Gly Ser Gly Tyr Lys Phe Thr Asp Tyr Ala Thr His Trp Val Lys
            260                 265                 270

Gln Ser His Ala Lys Ser Leu Glu Trp Ile Gly Val Ile Ser Thr Tyr
        275                 280                 285

Tyr Gly Asp Thr Thr Tyr Asn Gln Lys Phe Lys Gly Lys Ala Thr Met
    290                 295                 300

Thr Val Asp Lys Ser Ser Ser Thr Ala Tyr Met Glu Leu Pro Arg Leu
305                 310                 315                 320

Thr Ser Asp Asp Ser Ala Ile Tyr Tyr Cys Ala Leu Leu Arg Pro Phe
                325                 330                 335

Ala Tyr Trp Gly Gln Gly Thr Val Thr Val Ser Ser Gly Gly Gly Gly
            340                 345                 350

Gly Ser Gly Gly Gly Gly Ser Gly Gly Gly Gly Ser Asp Ile Glu Leu
        355                 360                 365

Thr Gln Ser Pro Ser Ser Leu Val Ser Ala Gly Glu Lys Val Thr
370                 375                 380
```

```
Met Ser Cys Lys Ser Ser Gln Ser Leu Leu Asn Ser Gly Asn Gln Asn
385                 390                 395                 400

Asn Asp Leu Ala Trp Tyr Gln Gln Lys Pro Gly Gln Arg Pro Lys Leu
            405                 410                 415

Leu Ile Tyr Gly Ala Ser Thr Arg Glu Ser Gly Val Pro Asp Arg Phe
        420                 425                 430

Thr Gly Ser Gly Ser Gly Thr Asp Phe Thr Leu Thr Ile Ser Ser Val
        435                 440                 445

Gln Ala Glu Asp Leu Ala Val Tyr Tyr Cys Gln Asn Asp His Ser Tyr
    450                 455                 460

Pro Leu Thr Phe Gly Ala Gly Thr Lys Leu Glu Ile Lys Arg Ala Ala
465                 470                 475                 480

Ala Gly Ser Glu Gln Lys Leu Ile Ser Glu Glu Asp Leu Ser His His
            485                 490                 495

His His His His
        500

<210> SEQ ID NO 139
<211> LENGTH: 1900
<212> TYPE: DNA
<213> ORGANISM: Artificial Sequence
<220> FEATURE:
<223> OTHER INFORMATION: vector pBS FRT KappaHEA1a

<400> SEQUENCE: 139
tacgccaagc gcgcgaagtt cctattctct agaaagtata ggaacttcga cgtcaaatac      60
aaaattttct tgctttattt ggaagccaat gtcacatggg aattgacttt cagtttaaag     120
aacttgatac aataaaagtc atttattttt ctaagttgtt tagaagtgac tttcatattc     180
agtgttgtga tctactcatg tctcttctct ttttccagcc tccagaggtg acatcttgct     240
gactcagtct ccagccatcc tgtctgtgag tccaggagaa agtcagtt tctcctgcag      300 ggccagtcag agcattggca taagtttaca ctggtatcag caaagaccaa gtgattctcc     360
aaggcttctc ataaagtatg cttctgagtc aatctctggg atcccttcca ggtttagtgg     420
cagtggatca gggacagatt ttactcttag catcaacagt gtggagtctg aagatattgc     480
agattattac tgtcaacaaa gtaatatctg gccaaccacg ttcggtgctg ggaccaagct     540
ggagctgaaa cgaactgtgg ctgcaccatc tgtcttcatc ttcccgccat ctgatgagca     600
gttgaaatct ggaactgcct ctgttgtgtg cctgctgaat aacttctatc ccagagaggc     660
caaagtacag tggaaggtgg ataacgccct ccaatcgggt aactcccagg agagtgtcac     720
agagcaggac agcaaggaca gcacctacag cctcagcagc accctgacgc tgagcaaagc     780
agactacgag aaacacaaag tctacgcctg cgaagtcacc catcagggcc tgagctcgcc     840
cgtcacaaag agcttcaaca ggggagagtg tgatgagccc aaatcttctg acaaaactca     900
cacatcccca ccgtccccac aagttcagga acgctggtg aaagtaaaag atgctgaaga     960
tcagttgggt gcacgagtgg gttacatcga actggatctc aacagcggta agatccttga    1020
gagttttcgc cccgaagaac gttttccaat gatgagcact tttaaagttc tgctatgtgg    1080
cgcggtatta tcccgtattg acgccgggca agagcaactc ggtcgccgca tacactattc    1140
tcagaatgac ttggttgagt actcaccagt cacagaaaag catcttacgg atggcatgac    1200
agtaagagaa ttatgcagtg ctgccataac catgagtgat aacactgcgg ccaacttact    1260
tctgacaacg atcggaggac cgaaggagct aaccgctttt ttgcacaaca tgggggatca    1320
```

-continued

```
tgtaactcgc cttgatcgtt gggaaccgga gctgaatgaa gccataccaa acgacgagcg    1380
tgacaccacg atgcctgtag caatggcaac aacgttgcgc aaactattaa ctggcgaact    1440
acttactcta gcttcccggc aacaattaat agactggatg gaggcggata agttgcagg    1500 accacttctg cgctcggccc ttccggctgg ctggtttatt gctgataaat ctggagccgg    1560
tgagcgtggg tctcgcggta tcattgcagc actggggcca gatggtaagc cctcccgtat    1620
cgtagttatc tacacgacgg ggagtcaggc aactatggat gaacgaaata gacagatcgc    1680
tgagataggt gcctcactga ttaagcattg gtaactgcaa ccacgttcgg tgctgggacc    1740
aagctggagc tgaaacgtaa gtacactttt ctcatctttt tttatgtgta agacacaggt    1800
tttcatgtta ggggttaaag tcagttcaga aaatcttgag aaaatggaga acgtcgaag     1860 ttcctattct tcaaatagta taggaacttc gcgcgctcac                         1900
```

<210> SEQ ID NO 140
<211> LENGTH: 498
<212> TYPE: PRT
<213> ORGANISM: Artificial Sequence
<220> FEATURE:
<223> OTHER INFORMATION: pBS FRT KappaHEAbla

<400> SEQUENCE: 140

```
Ala Ser Arg Gly Asp Ile Leu Leu Thr Gln Ser Pro Ala Ile Leu Ser
1               5                   10                  15

Val Ser Pro Gly Glu Arg Val Ser Phe Ser Cys Arg Ala Ser Gln Ser
            20                  25                  30

Ile Gly Ile Ser Leu His Trp Tyr Gln Gln Arg Pro Ser Asp Ser Pro
        35                  40                  45

Arg Leu Leu Ile Lys Tyr Ala Ser Glu Ser Ile Ser Gly Ile Pro Ser
    50                  55                  60

Arg Phe Ser Gly Ser Gly Ser Gly Thr Asp Phe Thr Leu Ser Ile Asn
65                  70                  75                  80

Ser Val Glu Ser Glu Asp Ile Ala Asp Tyr Tyr Cys Gln Gln Ser Asn
                85                  90                  95

Ile Trp Pro Thr Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Glu Pro Lys Ser Ser
    210                 215                 220

Asp Lys Thr His Thr Ser Pro Pro Ser Pro Gln Val Gln Glu Thr Leu
225                 230                 235                 240

Val Lys Val Lys Asp Ala Glu Asp Gln Leu Gly Ala Arg Val Gly Tyr
                245                 250                 255

Ile Glu Leu Asp Leu Asn Ser Gly Lys Ile Leu Glu Ser Phe Arg Pro
```

```
                260             265                 270
Glu Glu Arg Phe Pro Met Met Ser Thr Phe Lys Val Leu Leu Cys Gly
            275                 280                 285
Ala Val Leu Ser Arg Ile Asp Ala Gly Gln Glu Gln Leu Gly Arg Arg
            290                 295                 300
Ile His Tyr Ser Gln Asn Asp Leu Val Glu Tyr Ser Pro Val Thr Glu
305                 310                 315                 320
Lys His Leu Thr Asp Gly Met Thr Val Arg Glu Leu Cys Ser Ala Ala
                325                 330                 335
Ile Thr Met Ser Asp Asn Thr Ala Ala Asn Leu Leu Thr Thr Ile
                340                 345                 350
Gly Gly Pro Lys Glu Leu Thr Ala Phe Leu His Asn Met Gly Asp His
            355                 360                 365
Val Thr Arg Leu Asp Arg Trp Glu Pro Glu Leu Asn Glu Ala Ile Pro
            370                 375                 380
Asn Asp Glu Arg Asp Thr Thr Met Pro Val Ala Met Ala Thr Leu
385                 390                 395                 400
Arg Lys Leu Leu Thr Gly Glu Leu Leu Thr Leu Ala Ser Arg Gln Gln
                405                 410                 415
Leu Ile Asp Thr Met Glu Ala Asp Lys Val Ala Gly Pro Leu Leu Arg
                420                 425                 430
Ser Ala Leu Pro Ala Gly Trp Phe Ile Ala Asp Lys Ser Gly Ala Gly
            435                 440                 445
Glu Arg Gly Ser Arg Gly Ile Ile Ala Ala Leu Gly Pro Asp Gly Lys
            450                 455                 460
Pro Ser Arg Ile Val Val Ile Tyr Thr Thr Gly Ser Gln Ala Thr Met
465                 470                 475                 480
Asp Glu Arg Asn Arg Gln Ile Ala Glu Ile Gly Ala Ser Leu Ile Lys
                485                 490                 495
His Trp

<210> SEQ ID NO 141
<211> LENGTH: 713
<212> TYPE: DNA
<213> ORGANISM: Artificial Sequence
<220> FEATURE:
<223> OTHER INFORMATION: vector pBS FRT vKappa21

<400> SEQUENCE: 141
tacgccaagc gcgcgaagtt cctattctct agaaagtata ggaacttcga cgtcaaatac     60
aaaattttct tgctttattt ggaagccaat gtcacatggg aattgacttt cagtttaaag    120
aacttgatac aataaaagtc atttattttt ctaagttgtt tagaagtgac tttcatattc    180
agtgttgtga tctactcatg tctcttctct ttttccagcc tccagaggtg atatcgagct    240
cactcagtct ccatcctccc tgagtgtgtc agcaggagag aaggtcacta tgagctgcaa    300
gtccagtcag agtctgttaa acagtggaaa tcaaataac gacttggcct ggtaccagca    360
gaaaccaggg caacgtccta aactgttgat ctacggggca tccactaggg aatctggggt    420
ccctgatcgc ttcacaggca gtggatctgg aaccgatttc actcttacca tcagcagtgt    480
gcaggctgaa gacctggcag tttattactg tcagaatgat catagttatc cgttaacgtt    540
cggtgctggg accaagctgg agctgaaacg taagtacact tttctcatct ttttttatgt    600
gtaagacaca ggttttcatg ttaggggtta aagtcagttc agaaaatctt gagaaaatgg    660
agagacgtcg aagttcctat tcttcaaata gtataggaac ttcgcgcgct cac           713
```

<210> SEQ ID NO 142
<211> LENGTH: 118
<212> TYPE: PRT
<213> ORGANISM: Artificial Sequence
<220> FEATURE:
<223> OTHER INFORMATION: pBS FRT vKappa215

<400> SEQUENCE: 142

```
Ala Ser Arg Gly Asp Ile Glu Leu Thr Gln Ser Pro Ser Ser Leu Ser
1               5                   10                  15

Val Ser Ala Gly Glu Lys Val Thr Met Ser Cys Lys Ser Ser Gln Ser
            20                  25                  30

Leu Leu Asn Ser Gly Asn Gln Asn Asn Asp Leu Ala Trp Tyr Gln Gln
        35                  40                  45

Lys Pro Gly Gln Arg Pro Lys Leu Leu Ile Tyr Gly Ala Ser Thr Arg
    50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Gln Asn Asp His Ser Tyr Pro Leu Thr Phe Gly Ala Gly Thr
            100                 105                 110

Lys Leu Glu Leu Lys Arg
        115
```

<210> SEQ ID NO 143
<211> LENGTH: 1294
<212> TYPE: DNA
<213> ORGANISM: Artificial Sequence
<220> FEATURE:
<223> OTHER INFORMATION: vector pBS lox-FdHEA

<400> SEQUENCE: 143

| | | |
|---|---|---|
| tacgccaagc gcgcataact tcgtataatg tatgctatac gaagttatga cgtcaacctc | 60 |
| agaggatttg tcatctctag gcctgctcag tagaggttgc tatatagcag ggaaacatgc | 120 |
| aaataaggcc tctctcttct catgaaaacg agtcctgaac taaccttgaa tctgaagcaa | 180 |
| agggatcag cccgagattc tcattcagtg atcaacactg aacacacatc ccttaccatg | 240 |
| gatttgggc tgattttttt tattgttgct cttttaaaag gtaattcatg gaaagagat | 300 |
| actgagtgtg ttactggtca tgagcaagat agatggtgag cctgtatggc agtttgctga | 360 |
| cagaattctc tgtgttttca ggggtccagt gtgaagtgaa gcttctcgag tctgaggtg | 420 |
| gcctggtgca gcctggagga tccctgaaac tctcctgtgc agcctcagga ttcgatttta | 480 |
| gtagattctg gatgacttgg gtccggcagg ctccagggaa agggctagaa tggattggag | 540 |
| aaattaatct agatagcagt acgataaact atacgccatc tctaaaggat aaattcatca | 600 |
| tctccaggga caacgccaaa aatacgctgt tcctgcaaat gagcaaagtg agatctgagg | 660 |
| acacagccct ttattactgt tcaagagaac aaaagctgat ctcagaagaa gatctagact | 720 |
| actggggtca gggaacctca gtcaccgtct cctcaggtaa gaatggcctc tccaggtctt | 780 |
| tattttaac ctttgttatg gaattttctg agcattgcag actaatctta aatgtttgtc | 840 |
| gaccctcgcg gacagttaag aacccagggg cctctgcgcc ctgggcccag ctctgtccca | 900 |
| caccgcggtc acatggcacc acctctcttg cagcctccac caaggcccca tcggtcttcc | 960 |
| ccctggcacc ctcctccaag agcacctctg ggggcacagc ggccctgggc tgcctggtca | 1020 |

```
aggactactt ccccgaaccg gtgacggtgt cgtggaactc aggcgccctg accagcggcg   1080
tgcacacctt cccggctgtc ctacagtcct caggactcta ctccctcagc agcgtggtga   1140
ccgtgccctc cagcagcttg ggcacccaga cctacatctg caacgtgaat cacaagccca   1200
gcaacaccaa ggtggacaag aaagtttgag gtgagaggcc agtcgacgtc ataacttcgt   1260
ataatgtata ctatacgaag ttatgcgcgc tcac                               1294
```

<210> SEQ ID NO 144
<211> LENGTH: 140
<212> TYPE: PRT
<213> ORGANISM: Artificial Sequence
<220> FEATURE:
<223> OTHER INFORMATION: pBS loxP-FdHEA

<400> SEQUENCE: 144

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Phe Trp Met Thr Trp Val Arg Gln Ala Pro Gly Lys Gly Leu Glu
    50                  55                  60

Trp Ile Gly Glu Ile Asn Leu Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Phe Leu Gln Met Ser Lys Val Arg Ser Glu Asp Thr Ala Leu Tyr
            100                 105                 110

Tyr Cys Ser Arg Glu Gln Lys Leu Ile Ser Glu Glu Asp Leu Asp Tyr
        115                 120                 125

Trp Gly Gln Gly Thr Ser Val Thr Val Ser Ser Gly
    130                 135                 140
```

<210> SEQ ID NO 145
<211> LENGTH: 106
<212> TYPE: PRT
<213> ORGANISM: Homo sapiens

<400> SEQUENCE: 145

```
Cys Glu Gly Arg Asn Phe Ser Lys Thr Val Pro Ser Ser Leu Gly Gln
1               5                   10                  15

His Thr Val Glu Cys Ala Tyr Val Lys His Lys Glu Tyr Asp Ala Lys
            20                  25                  30

Ser Leu Thr Leu Thr Ser Ser Leu Ser Tyr Thr Ser Asp Lys Ser Asp
        35                  40                  45

Gln Glu Thr Val Ser Glu Gln Ser Asn Gly Ser Gln Leu Ala Asn Asp
    50                  55                  60

Val Lys Trp Gln Val Lys Ala Glu Arg Pro Tyr Phe Asn Asn Leu Leu
65                  70                  75                  80

Cys Val Val Ser Ala Thr Gly Ser Lys Leu Gln Glu Asp Ser Pro Pro
                85                  90                  95

Phe Ile Phe Val Ser Pro Ala Ala Val Thr
            100                 105
```

<210> SEQ ID NO 146
<211> LENGTH: 34

```
<212> TYPE: DNA
<213> ORGANISM: Artificial Sequence
<220> FEATURE:
<223> OTHER INFORMATION: FLP Recombinase Recognition Site (FRT)

<400> SEQUENCE: 146
gaagttccta ttctctagaa agtataggaa cttc                               34

<210> SEQ ID NO 147
<211> LENGTH: 34
<212> TYPE: DNA
<213> ORGANISM: Artificial Sequence
<220> FEATURE:
<223> OTHER INFORMATION: FRT3

<400> SEQUENCE: 147
gaagttccta ttcttcaaat agtataggaa cttc                               34

<210> SEQ ID NO 148
<211> LENGTH: 34
<212> TYPE: DNA
<213> ORGANISM: Artificial Sequence
<220> FEATURE:
<223> OTHER INFORMATION: lox66 site

<400> SEQUENCE: 148
taccgttcgt ataatgtatg ctatacgaag ttat                               34

<210> SEQ ID NO 149
<211> LENGTH: 34
<212> TYPE: DNA
<213> ORGANISM: Artificial Sequence
<220> FEATURE:
<223> OTHER INFORMATION: lox71 site

<400> SEQUENCE: 149
ataacttcgt ataatgtatg ctatacgaac ggta                               34

<210> SEQ ID NO 150
<211> LENGTH: 34
<212> TYPE: DNA
<213> ORGANISM: Artificial Sequence
<220> FEATURE:
<223> OTHER INFORMATION: loxP site

<400> SEQUENCE: 150
ataacttcgt ataatgtatg ctatacgaag ttat                               34

<210> SEQ ID NO 151
<211> LENGTH: 34
<212> TYPE: DNA
<213> ORGANISM: Artificial Sequence
<220> FEATURE:
<223> OTHER INFORMATION: loxP511 site

<400> SEQUENCE: 151
ataacttcgt ataatgtata ctatacgaag ttat                               34

<210> SEQ ID NO 152
<211> LENGTH: 34
<212> TYPE: DNA
<213> ORGANISM: Artificial Sequence
<220> FEATURE:
<223> OTHER INFORMATION: loxG site

<400> SEQUENCE: 152
```
ataacttcgt atagcataca ttatacgaag ttgc                            34

<210> SEQ ID NO 153
<211> LENGTH: 12
<212> TYPE: DNA
<213> ORGANISM: Artificial Sequence
<220> FEATURE:
<223> OTHER INFORMATION: chemically synthesized

<400> SEQUENCE: 153
attataacgc gt                                                    12

<210> SEQ ID NO 154
<211> LENGTH: 14
<212> TYPE: DNA
<213> ORGANISM: Artificial Sequence
<220> FEATURE:
<223> OTHER INFORMATION: chemically synthesized

<400> SEQUENCE: 154
attatagcgg ccgc                                                  14

<210> SEQ ID NO 155
<211> LENGTH: 37
<212> TYPE: DNA
<213> ORGANISM: Artificial Sequence
<220> FEATURE:
<223> OTHER INFORMATION: chemically synthesized

<400> SEQUENCE: 155
ttcgaagttc ctatactatt tgaagaatag gaacttc                         37

<210> SEQ ID NO 156
<211> LENGTH: 50
<212> TYPE: DNA
<213> ORGANISM: Artificial Sequence
<220> FEATURE:
<223> OTHER INFORMATION: sequence flanked by FRT sites

<400> SEQUENCE: 156
attatagacg tcacgcgtaa tgtcgactat gcggccgcga cgtcaatata           50

<210> SEQ ID NO 157
<211> LENGTH: 37
<212> TYPE: DNA
<213> ORGANISM: Artificial Sequence
<220> FEATURE:
<223> OTHER INFORMATION: chemically synthesized

<400> SEQUENCE: 157
ttcgaagttc ctattctcta gaaagtatag gaacttc                         37

<210> SEQ ID NO 158
<211> LENGTH: 6
<212> TYPE: DNA
<213> ORGANISM: Artificial Sequence
<220> FEATURE:
<223> OTHER INFORMATION: MluI restriction site

<400> SEQUENCE: 158 acgcgt                                                            6

<210> SEQ ID NO 159
<211> LENGTH: 37
<212> TYPE: DNA
<213> ORGANISM: Artificial Sequence

```
<220> FEATURE:
<223> OTHER INFORMATION: sequence with loxP site

<400> SEQUENCE: 159
ttcataactt cgtataatgt atgctatacg aagttat                              37

<210> SEQ ID NO 160
<211> LENGTH: 14
<212> TYPE: DNA
<213> ORGANISM: Artificial Sequence
<220> FEATURE:
<223> OTHER INFORMATION: NotI restriction site

<400> SEQUENCE: 160
attatagcgg ccgc                                                      14

<210> SEQ ID NO 161
<211> LENGTH: 37
<212> TYPE: DNA
<213> ORGANISM: Artificial Sequence
<220> FEATURE:
<223> OTHER INFORMATION: sequence with loxP511 site

<400> SEQUENCE: 161
cctataactt cgtataatgt atactatacg aagttat                             37
```

METHOD FOR PRODUCING PROTEIN LIBRARIES AND FOR SELECTING PROTEINS FROM SAID LIBRARIES

This application is a U.S. National Phase of PCT/EP02/10852, filed Sep. 27, 2002, which claims the benefit of European patent application number 01123596.7, filed on Oct. 1, 2001, the disclosures of which are incorporated by reference herein in their entirety.

FIELD OF THE INVENTION

The present invention relates to a method of producing a protein library with great diversity and of selecting proteins therefrom, in particular human monoclonal antibodies having the desired specificity.

BACKGROUND OF THE INVENTION

Numerous attempts have already been made to obtain antibodies having a desired specificity in high yields and with good human compatibility, in particular as therapeutic agents, the individual methods being briefly described below.
Hybridoma Antibodies.

In the 70ies, Köhler and Milstein developed a method of obtaining antibodies, i.e. the hybridoma method (Köhler and Milstein, 1975, Continuous cultures of fused cells secreting antibody of predefined specificity. Nature, 256, 495-497). It first calls for an immunization of an experimental animal (usually a mouse or rat). Then, the spleen or lymph nodes are removed and the B lymphocytes contained therein in large numbers (initial stages of the antibody-producing cells) are collected. On account of "its" individual gene rearrangement, every B lymphocyte produces antibodies having only a single binding specificity. The descendents of these B lymphocytes, i.e. the B lymphocyte clones, only produce antibodies of this binding specificity.

Some of the cells obtained from the spleen of an immunized animal produce antibodies having the desired specificity. In order to be able to produce them in vitro, the B lymphocytes have to be multiplied in a cell culture. This is achieved by fusing them with myeloma cells, descendents of a plasma cell tumor. The resulting hybridoma cells show properties of both fusion partners: On the one hand, they have the immortality of cancer cells and, on the other hand, they produce the particular antibody of the B lymphocyte partner. The descendents of an individual hybridoma cell (i.e. their clone) produce antibodies having this defined specificity. They are thus also referred to as monoclonal antibodies. The method of producing hybridomas is shown in FIG. 1 by way of diagram. An advantage of the monoclonal antibodies as compared to the polyclonal antibodies is that they can be produced by the then immortal cells in a quantity which is unlimited, in principle.
Drawbacks:

In the former hybridoma method, mice are immunized and the murine B lymphocytes are then fused to a myeloma cell line. Thereafter, the thus formed hybridoma cells are propagated separately as individual cell clones and the supernatant of the individual clones is searched for antibodies having the desired specificity. Then, the identified individual clones must immediately be subcloned in a second selection run, since they are genetically instable during this period. This method is very time-consuming so that in the final analysis a maximum of several thousand hybridoma clones can be tested for the desired specificity. By means of this technique it is rather limited to establish and screen a hybridoma library. As a result, it is very difficult to automate this method. This conventional method does not permit the production of human antibodies.
Murine Strains Producing Human Hybridoma Antibodies.

Special cases are human hybridoma antibodies which can be obtained from transgenic mice, whose own immunoglobulin gene locus was replaced by parts of the human immunoglobulin gene locus (Jakobovits, 1995, Production of fully human antibodies by transgenic mice. Curr Opin Biotechnol 6, 561-566; Lonberg and Huszar, 1995, Human antibodies from transgenic mice. Int Rev Immunol. 13, 65-93; Kucherlapati et al., U.S. Pat. No. 6,114,598: Generation of xenogeneic antibodies). The human antibody genes are rearranged, pass through the class switch and are hypermutated somatically. These transgenic mice thus produce human antibodies in murine cells which (in contrast to human hybridoma cells) result in stable murine hybridomas.
Drawbacks:

Although human antibodies can be produced by means of this technique, it is as time-consuming, expensive and complex as the above discussed hybridoma technique. Little has been known about the actual quality of the generated transgenic murine strains to date. This includes questions such as: Does the interplay between humanized antibodies and other murine signals create a disturbance? What quality has the immune response of the mice? How many antibody genes function/are in the murine genome? etc. For this reason, it is not yet clear whether these "humanized mice" can meet the expectations placed on them.
Humanized Hybridoma Antibody.

A plurality of murine hybridoma antibodies which might be of therapeutic interest is already available. However, a problem with their therapeutic use is their murine origin, since proteins from a foreign species are recognized to be foreign by the human immune system. This also applies to murine antibodies. What is called the "HAMA" immune response (human anti-murine antibodies) occurs. These antibodies formed by the human immune system within some days usually neutralize the therapeutically used murine antibody, thus rendering it ineffective. Also, a repeated therapy is only possible to a very limited extent (Courtenyl-Luck et al., 1986, Development of Primary and Secondary Immune Responses to Mouse Monoclonal Antibodies Used in the Diagnosis and Therapy of Malignant Neoplasms. Cancer Res. 46, 6489-6493; Lamers et al., 1995, Inhibition of bispecific monoclonal antibody (bsAb) targeted cytolsis by human anti mouse antibodies in ovarian carcinoma patients treated with bsAb targeted activated T lymphocytes. Int J Cancer 60, 450-457).

The large majority of the HAMA antibodies is directed against the constant antibody part and this is why the production of antibody chimeras has been favored. The latter contain a variable mouse antibody domain, followed by the constant antibody domains from humans. For this purpose, a human antibody gene is initially inserted in a cloning vector (Wright et al., 1992, Genetically engineered Antibodies: Progress and Prospects. Critical Rev Immunol. 12, 125 168). The individual antibody domains form compact folding units which are interconnected by a peptide strand. The possibility of a disturbance of the antibody function is the least when whole antibody domains are exchanged. By means of the PCR invention it is possible, without any problems, to produce chimeric cDNAs since cloning down to the base is substantially simplified by this method. The resulting chimeric antibodies still bind specifically to the antigen. Yet the HAMA response is markedly reduced.

However, another fact is more important than the HAMA response: Since the constant domains are now derived from humans, these chimeric antibodies are also markedly better for activating some helper functions of the human immune system, such as antibody dependent cellular cytotoxicity (ADCC) or complement activation. This is another reason why some of these humanized antibodies are already in clinical use (McLaughlin et al., 1998, Clinical status and optimal use of Rituximab for B-cell lymphomas. Oncology 12, 1763-1777).

Drawbacks:

The humanization of already existing hybridoma antibodies is also very difficult and time-consuming. The stability of the thus produced hybridomas often creates a problem: The cells mutate or they secrete only some antibodies into the medium.

Humanization by Homologous Recombination.

U.S. Pat. No. 5,202,238 describes a method by which monoclonal murine antibodies can be humanized. This method focuses on what is called "homologous recombination". Here, human sequences flanked by suitable genomic murine sequences are recombined in the active antibody site at the proper locations. The major advantage of this method is that the signals, optimized with respect to good antibody production, of the antibody site are largely maintained (Yarnold and Fell, 1994, Chimerization of antitumor antibodies via homologous recombination conversion vectors. Cancer Research 54, 506-512; Fell et al., 1989, Homologous recombination in hybridoma cells: heavy chain chimeric antibody produced by gene targeting. PNAS 86, 8507-8511).

Drawbacks:

Similar to the generation of hybridomas this method calls for a lot of work in order to isolate a single humanized hybridoma. Thousands of clones have to be cultured and analyzed separately for this. Another drawback results from the employed selection marker: It obviously causes a large number of revertants (the human antibody locus recombined thereinto is again excised in the reverse reaction) and/or an impairment of the expression level (Baker et al., 1994, J. Immunological Methods 168, 25-32). In addition, the inserted resistance genes prevent the surface presentation of the antibodies when they are inserted in the intron between the CH3 exon and the M1 exon of an IgG.

Recombinant Antibodies.

In the last few years, a possibility based on genetic-engineering methods for the production of antibody fragments was opened up by the construction of recombinant antibodies (Breitling and Dübel, 1997, "Rekombinante Antikörper" [recombinant antibodies], Spektrum-Verlag ISBN 3-8274-0029-5). Here, the antibodies are no longer produced in an experimental animal (or in a human organism) but in vitro in bacteria or a cell culture and the focus is laid on the antigen-binding part of the antibody. Usually the rest of the antibody molecule is dispensed with to the advantage of a greater yield. Of course, these fragments can no longer convey all the functions of a naturally produced antibody. However, they can be fused in a comparatively simple way with enzymes or other antibodies. These recombinant antibodies are thus given completely new properties. The term "recombinant antibody" has become established for an antibody fragment produced in vitro by means of genetic engineering and otherwise defined exclusively via its antigen specificity.

Drawbacks:

Recombinant antibodies lack the constant antibody portion and thus the effector functions essential for many therapy approaches. For this reason, newly discovered "antibody heads" are "grafted" onto eukaryotic expression vectors for many applications, i.e. the above described labor-intensive method is used. Along with the resulting experimental work, a poor expression may result since the bacterial system prefers codons differing from those preferred in the eukaryotic systems. Another drawback results from the properties of the "single chain" antibodies usually used (svFv): They are usually rather unstable and aggregate readily. In addition, many variable domains are obviously attacked by E. coli proteases. Thus, the published complexities of the scFv antibody libraries (up to $10^{11}$) also have to be taken with caution. In addition to the just described problems, these libraries obviously also still contain a large number of cloning artifacts. This in turn means that the selected clones represent almost exclusively artifacts after 4 selection runs at the latest. Another drawback is the fact that usually more than one selection run is required to obtain the desired antibody. This is because per phage only about 0.1 scFv antibodies are presented on the phage surface. It is very likely that this value varies widely, depending on the presented antibody. Another drawback is that the identities of the individual clones (i.e. does the selected clone actually produce an antibody?) have to be checked in a rather time-consuming and costly manner.

Presentation of Antibodies on the Surface of Hybridoma Cells.

This technique is based on the above described hybridoma technique. In contrast thereto, however, the latter uses (and produces) a stable myeloma cell line which anchors large amounts of an antibody binding protein (e.g. protein G) on the cell surface (Breitling et al., 1999, Selektion von monoklonalen Antikörpern [selection of monoclonal antibodies]. DE 199 00 635 A1. PCT-Application under number PCT DE00/00079). This serves for avoiding a major part of the work which results from the cloning and subcloning of the monoclonal hybridomas. The desired antibody specificities can be isolated in a FACS sorter or with magnetobeads from a pool of hybridomas instead, since the produced antibodies are anchored to the described antibody binding protein on the cell surface as a result of the bond.

Drawbacks:

This technique prevents only part of the time-consuming work required for selecting individual antibody specificities. Mice still have to be immunized and the murine B lymphocytes then have to be fused with a myeloma cell line. This is done with relatively poor efficiency: Only 100-500 different hybridomas are usually generated per fusion and mouse. The thus formed hybridoma cells also have an undesired high variability as regards the number of presented antibodies, which strongly impairs the selection in the FACS sorter. In addition, a cross-talk between different antibody specificities results because of the non-covalent antibody anchorage on the surface. As a result, the different hybridoma cells do not only present "their" specific antibody on the surface but also other antibody specificities which are released into the medium by other hybridoma cells. This method is also time-consuming so that in the final analysis only a maximum of several ten thousand different hybridomas can be generated (and can then be tested for the desired specificity). Thus, the establishment and the screening of a hybridoma library by means of this technique are limited. This also applies to the automation of this method. Moreover, this technique also fails to enable the production of human antibodies.

Cassette Exchange by Means of Specific Recombination.

There are meanwhile a number of methods enabling a DNA site-specific recombination within a eukaryotic cell (see e.g. Sauer, U.S. Pat. No. 4,959,317: Site-specific recombination of DNA in eukaryotic cells: Lebouch et al., U.S. Pat. No. 5,928,914: "Methods and compositions for transforming cells; Feng et al., 1999, Site-specific chromosomal integration in mammalian cells: highly efficient CRE recombinase-mediated cassette exchange. J. Mol. Biol. 292, 779-785). All of these methods use recombinase (e.g. Flp, Cre, Int, etc.) which recognizes specific DNA sequences and recombines them with other DNA sequences. Characteristics of these methods are the often rather high efficiencies of the specific recombination events which can be achieved in vitro but also in vivo by means of these methods. These methods are applied, e.g. as cloning aids (exchange of DNA cassettes in vitro) but also in vivo for a recombination in living bacteria, in living eukaryotic cells and even in transgenic mice.

Drawbacks:

The cassette exchange of antibody genes in eukaryotic cells in combination with the surface expression and subsequent selection of monoclonal antibodies has not yet been described.

SUMMARY OF THE INVENTION

The technical problem underlying the present invention is thus the provision of a method for establishing a protein library, preferably an antibody library, and/or for selecting proteins, preferably antibodies, having desired specificities, which does not comprise the drawbacks of the former methods described above. This method should also comprise the establishment of a library of different T cell receptors, for example. In particular, this method shall combine the advantages of the recombinant antibody technique and the hybridoma antibody technique:

The simple selection of specific reactivities from a very large number of different antibodies (more generally: proteins), if possible, in connection with a high signal intensity during the selection step (e.g. because each cell presents many antibodies of the same kind);

the comparatively simple modification of the expressed genes, such as e.g. the fusion of the light antibody chain with a single-chain antibody (bispecific antibodies) or the fusion with another protein portion (see also: Bispecific antibodies by Michael W. Fanger. Springer Verlag, 1995, ISBN 3-540-58885-X);

the production of large quantities of the selected antibodies (proteins) in good quality for diagnostic or therapeutic purposes, in particular by a variant released into the culture medium, and as a result, the simple verification and characterization of the selected cell line or sub-library.

This technical problem is solved by providing the embodiments characterized in the claims. The selection of cells producing specific proteins (e.g. monoclonal antibodies) can be accelerated by means of the present invention. The number of cells which can be searched for a given specificity can be raised by the method according to the invention by several orders. Proteins (antibodies) are here selected in a single selection run. This is enabled by the large number of proteins (antibodies) presented on the cell surface and in addition by the comparatively homogeneous number of proteins (antibodies) presented by the particular cells. The search for different antibody specificities can readily be carried out by means of the antibody library produced by the method according to the invention. In addition, it enables the automation of the search for monoclonally expressed antibodies so as to better use the huge range of application of monoclonal antibodies. This, in turn, enables a better use of the obviously large potential of human or humanized antibodies in the therapy of diseases. The above mentioned simplified selection of monoclonal hybridoma antibodies yields cell clones producing large amounts of monoclonal antibodies which, compared with the recombinant antibodies, also have a superior quality. Moreover, the selection of the cells can be carried out without inserted resistance markers, which is advantageous since they obviously impair the expression of the modified gene product and simultaneously the stability of the resulting cell line in many cases. For example, the integration of the resistance marker between the CH3 exon (where appropriate, CH4 exon) and the M1 exon prevents a membrane-bound splicing variant from anchoring the antibodies on the surface of the cell which presents them so as to prevent an especially simple selection on account of the surface expression of antigen-specific antibodies (FIG. 2). Besides, one embodiment of the present invention enables the simple humanization of murine hybridomas and thus e.g. also the establishment of a wide range of monoclonal antibodies having equal antigen specificity and different Fc portions. Because of this aspect it is possible to use the huge preliminary work in the field of monoclonal murine antibodies for the comparativebly simple production of human therapeutic agents.

The method according to the invention is based on the fact that a large and, compared from cell to cell, highly uniform number of antibodies are bonded covalently to the surface of a eukaryotic cell and thus comparable signals from cell to cell can be expected. Hence specific antibodies can be selected together with the presenting cell from a plurality of cells in a comparatively easy way. This selection serves for obtaining a monoclonal antibody. The group of antibody-presenting cells is obtained by a reconstruction of a eukaryotic cell. This is done in particular by several homologous (FIGS. 3, 4, 7 and 8) and specific (FIGS. 5, 6, and 9) recombination events carried out one after the other. In particular murine hybridoma cells (FIG. 3) are used for this purpose. Alternatively, e.g. a human myeloma cell line can also be used as a basis for the sequential homologous recombinations (FIG. 4). This has the additional advantage that the glycosylation, slightly different in comparison with human cells, of the antibodies produced by murine cells is avoided. However, it is also possible to use other stable cell lines, in particular cell lines which produce large quantities of a certain gene product, such as T cell lymphomas. A wide antibody variety is generated by the method according to the invention (FIGS. 5, 6, 9). Another element of this invention enables the selection of individual cells from the previously generated diversity. This is enabled by the surface presentation of the antibodies (FIGS. 2, 9, 10). In contrast to the formerly used technique, however, this is done (a) preferably by covalent linkage of the antibodies on the cell surface, and (b) by means of eukaryotic cells, preferably mammalian cells, the above described drawbacks of some of the formerly used techniques being avoided.

In a special embodiment, the method according to the invention is followed by a somatic hypermutation of the presented antibodies (and genes), in particular to select antibodies which can bind an antigen with increased affinity. For this purpose, e.g. in the context of the antibody gene loci, expression vectors for RAD54, RecQ4 and for the DNA polymerase polX mu can be used (FIG. 11), in particular in combination with a vector which expresses anti-sense RNA or siRNA (Martines et al., (2002), Cell 110, 563 et seq.; Elbashir et al., (2001), Nature 411, 494-498) against XRCC2, XRCC3 or RAD51VB. Alternatively, e.g.:

A plurality of non-directed mutations is introduced by an error-prone PCR, in particular into already pre-selected variable antibody genes;

a plurality of these mutated variable antibody genes is recombined into the antibody site by means of specific recombination signals (FIGS. 5, 6); and the cells which present an antibody of higher affinity on the surface are subsequently selected in a FACS, for example (FIG. 10).

Here, the non-directed mutations can be combined according to the method developed by Stemmer (1994, Nature 370, 389-391), for example. However, it is also possible to simply exchange the variable domain of an antibody chain with a plurality of other variable domains in a previously selected antibody-producing cell by means of the specific recombination signals (FIGS. 5, 6, 9) and then search for more affine variants. Thus, the method according to the invention shows several possibilities enabling a somatic hypermutation in vitro followed by a selection of more affine antibodies (FIGS. 10, 11).

In summary, the method according to the invention has the following advantages: It permits the production of a highly complex library, e.g. as a source for monoclonal antibodies (FIGS. 6, 9), and the simple selection in particular of highly affine human monoclonal antibodies (FIGS. 10, 11). At the same time, the chances of success of such a selection can be increased. The signal strength can markedly be increased in the search for specific monoclonal antibodies by the large and rather uniform number of presenting antibodies. The human high-affinity monoclonal antibodies which can be obtained in high yields by the method according to the invention can be used as tumor diagnostic agents and tumor therapeutic agents, for example. In addition, other proteins or individual protein domains, in particular exons, can be presented on the surface of "their" particular cell in place of antibodies so as to enable a particularly simple search for binding partners for these presented protein fragments.

Figure 1:
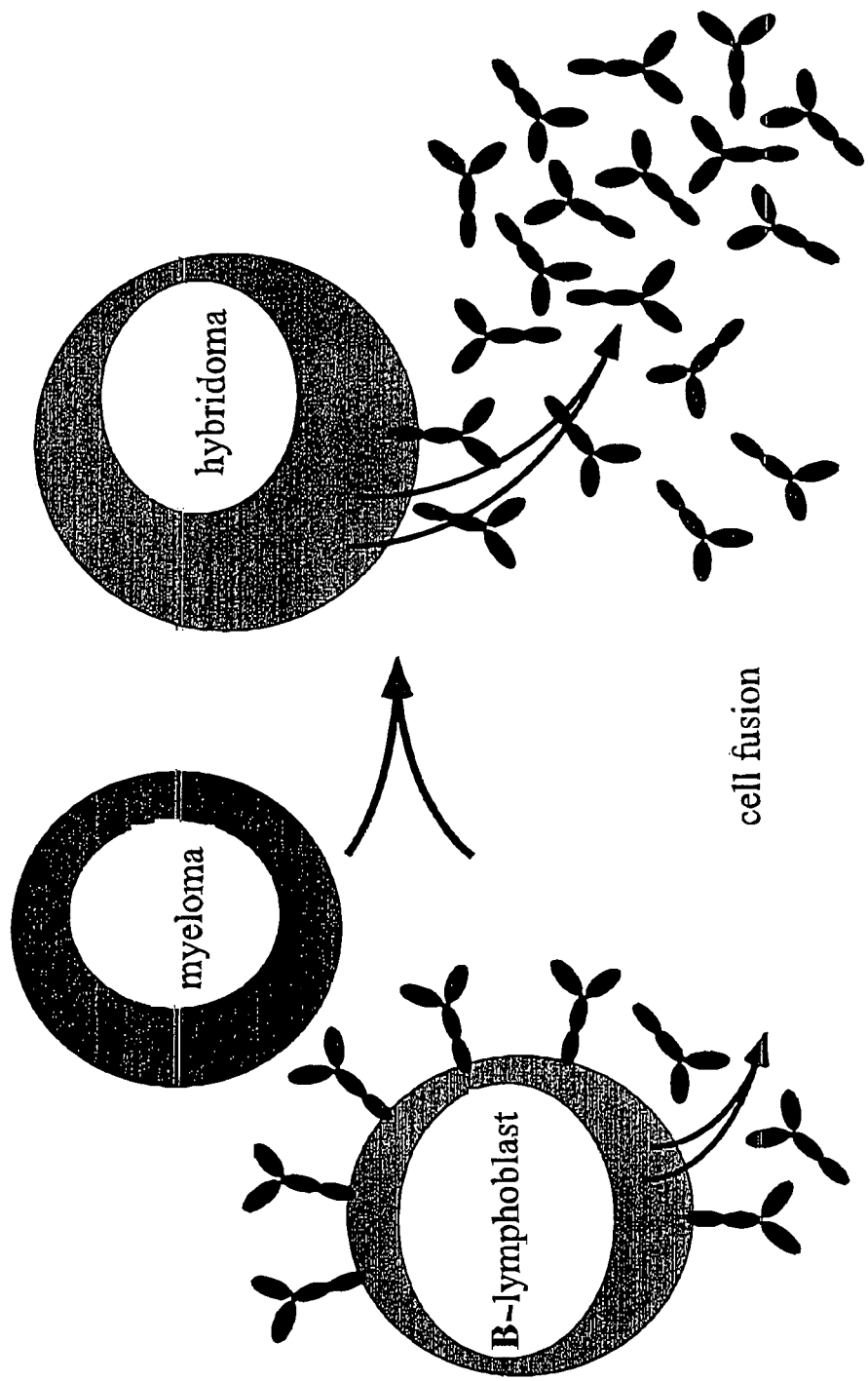
FIG. 1

Diagram showing the production of hybridoma cells. B lymphoblasts are usually fused with a myeloma cell line (e.g. Ag8.653) by adding a mixture of polyethylene glycol (PEG) and DMSO. Thereafter, individual cell clones are propagated by limited dilution, and the cell culture supernatant thereof is analyzed as to the searched specific antibody reactivity after about 14 days. The resulting hybridoma cell acquires properties of both parental cells: The myeloma cell contributes the immortality of a tumor cell line and some control signals for an efficient production of antibodies while the B lymphoblast contributes a specific antibody reactivity of genomically recombined antibody fragments. Initially, the resulting hybridoma cell is genetically unstable so that a genetically more stable variant has to be established in at least one further selection run.

FIG. 2

A. Genomic sequences of a genomically recombined IgG1 antibody gene. This part shows the genomic structure of the light chain including promoter (P), enhancer (e), leader exon (L), the vL domain (vL) with genomically recombined J segment (J) and the exon for the constant domain of the light chain (cL). It also shows the genomic structure of the heavy chain including promoter (P), enhancer (e), leader exon (L), the vH domain (vH) with genomically recombined D and J segments (DJ) and the exons for the constant CH1, Hinge (H), CH2 and CH3 domains of the heavy chain. Two exons coding for a membrane anchor (M1 and M2) are located at the 3' end of the IgG1 gene.

B. This part shows spliced mRNAs of an IgG1 antibody. The spliced mRNA of the light chain and two differentially spliced mRNAs of the heavy chain which code for a secretory variant (sIgG1) and/or a membrane-bound variant (mIgG1) of an IgG1.

C. IgG1 antibody protein. This part shows the light antibody chain including vL and CL domains. The leader peptide is splitt off. The heavy antibody chain exists as 2 variants
with vH, CH1, H, CH2, CH3 domains (secreted form; sIgG1) and
with vH, CH1, H, CH2, CH3, M1 and M2 domains (membrane-bound form; mIgG1).

FIG. 3

Homologous recombination. The DNA sequences of defined gene loci can be modified by means of homologous recombination. This technique is presently the focus above all for the production of modified ES cell lines and/or transgenic mice. An experimentalist initially charges a defined first DNA sequence which is flanked on either side by further DNA sequences. These further DNA sequences should usually contain >700 Bp long homologous regions which have their equivalent in the chromosomes: the thus definable gene loci. Recombination events have to take place within these further DNA sequences (shown by crossed lines) so as to exchange the chromosomal regions located between the further DNA sequences between the chimeric DNA and the chromosomal DNA. After the transfection of suitable chimeric, in particular linearized, DNA (shown above the chromosomal DNA), this very rare event takes place in about 1 out of $10^7$ cells. The figure shows gene loci of the murine hybridoma cell line HEA125 suited for this purpose within the meaning of this invention (see also FIG. 2). If on account of a homologous recombination the antibody presented on the surface is modified, the corresponding cell can be isolated by means of FACS. Depending on the selection of said further DNA sequences the experimentalist decides whether in addition to the introduction of said first DNA sequence more or less large areas are deleted after the homologous recombination. The figure shows:

I. The exchange of the exon for the constant murine kappa domain with an exon which codes for a constant human kappa domain, II. the exchange of the CH1, CH2 and CH3 exons for the constant murine IgG1 domains with the corresponding exons of the constant human IgG1 domains (the hinge exon is not shown), III. like (II.), DNA sequences of the intron being additionally deleted between the CH3 domain and the M1 domain of the encoded IgG1, IV. the exchange of the exon for the active variable L1 domain with an exon which codes for a vL2 domain selectable in FACS, for example, two specific recombination signals (FRT0 and FRT3) which are recognized by Flp recombinase being simultaneously introduced, and V. the exchange of the exon for the active variable H1 domain with an exon coding for a vH2 domain selectable in FACs, for example, two specific recombination signals (loxP1 and loxP2) which are recognized by Cre recombinase being simultaneously introduced.

If recombination events I, III, IV and V shown in the figure are carried out one after the other and the corresponding cell lines are isolated, a hybridoma cell line will result which presents a comparatively large number of a defined monoclonal antibody on its surface. The variable domains of this monoclonal antibody can be exchanged rather easily with the corresponding domains of other antibodies or groups of antibodies on account of the introduced specific recombination signals.

FIG. 4

Figure 3:
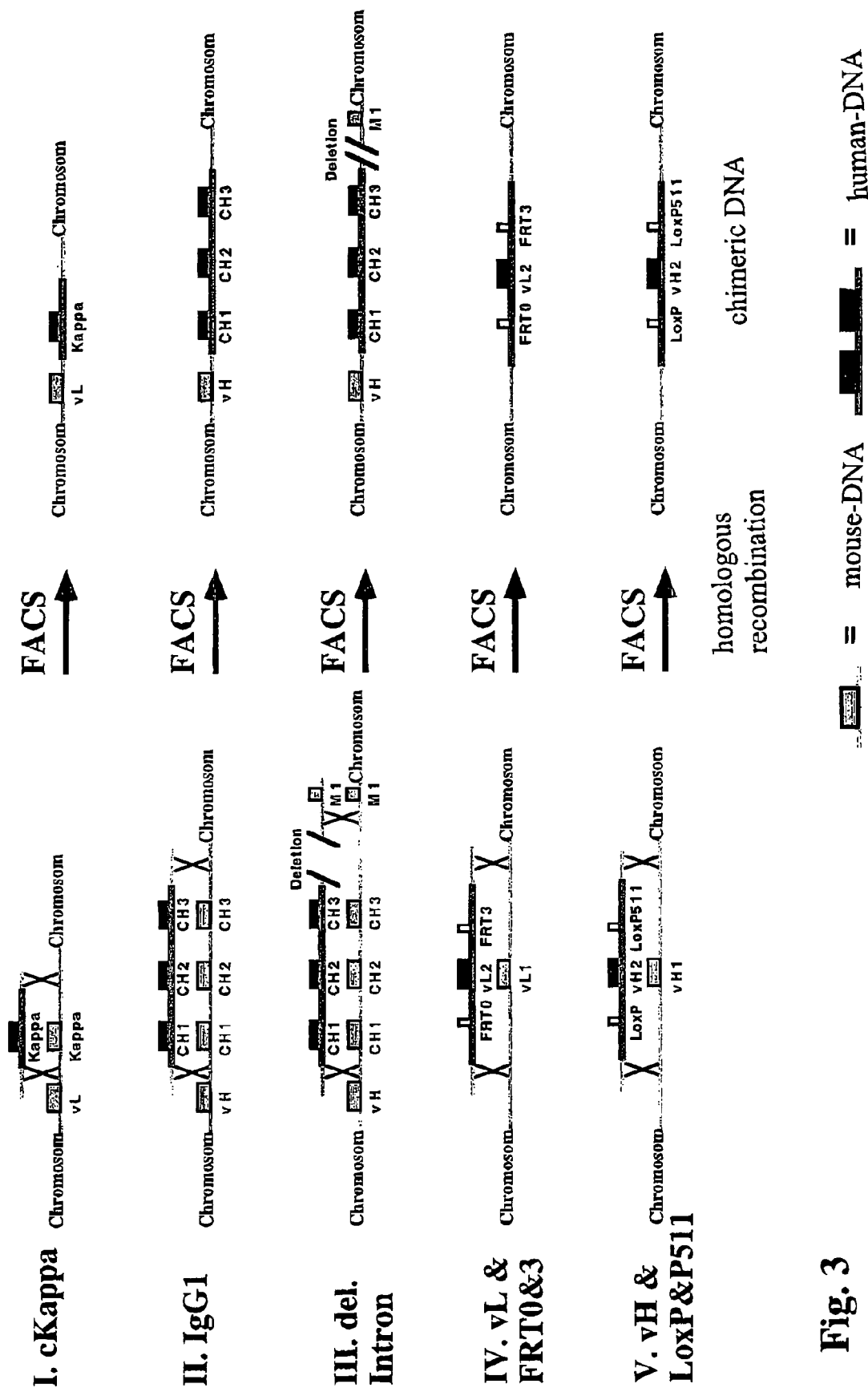
Figure 4:
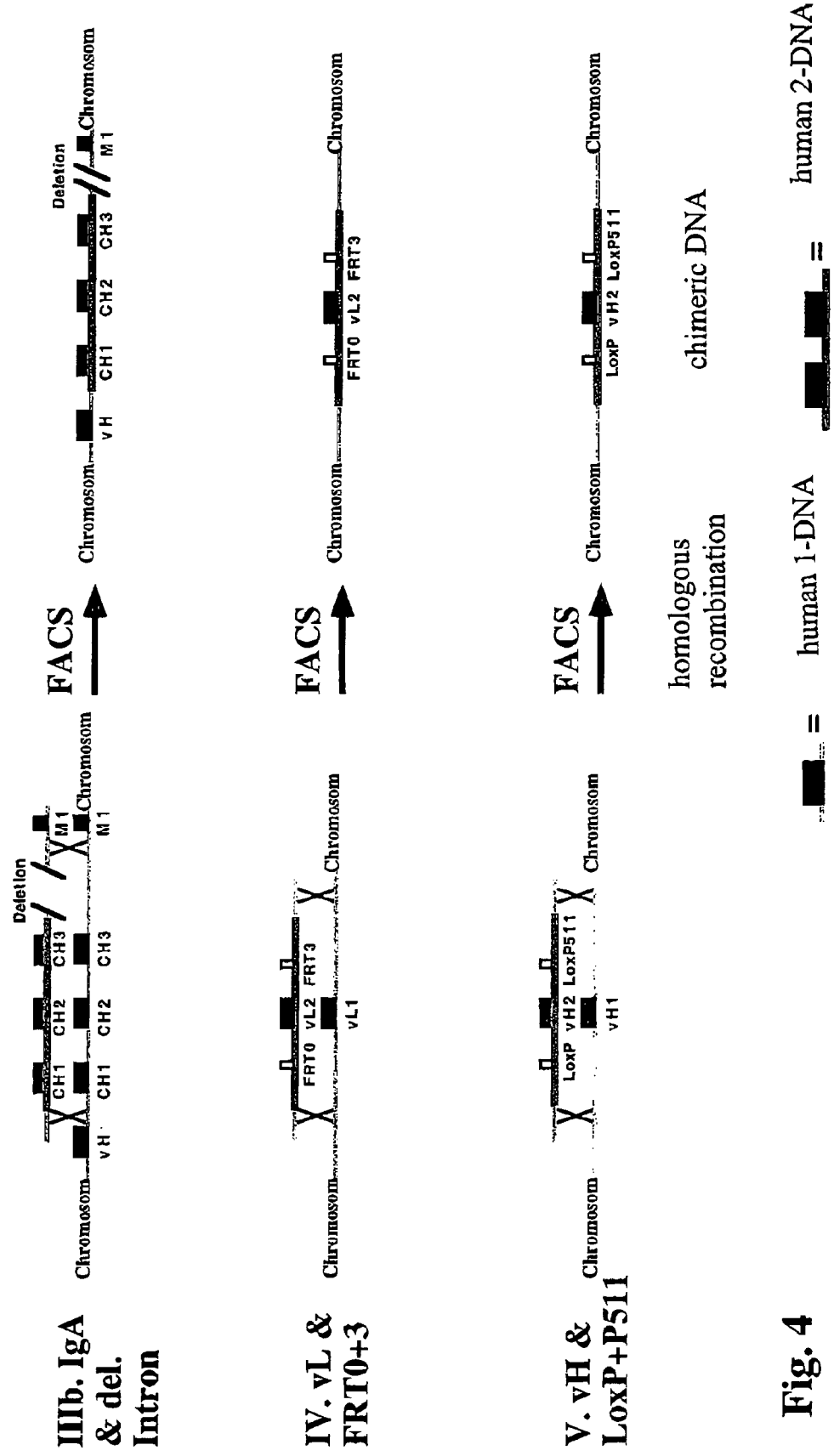

Reconstruction of a human cell line by homologous recombination. In contrast to the homologous recombination events shown in FIG. 3, FIG. 4 shows the modification of a human cell line (e.g. IM-9 or U266) by various homologous recombination events. The figure shows:

- III. (b.) The exchange of the CH1, CH2 and CH3 exons, e.g. for the constant human IgA domains, with the corresponding exons of the constant human IgG1 domains, DNA sequences of the intron being additionally deleted between the CH3 domain and M1 domain of the encoded IgG1/IgA,
- IV. the exchange of the exon for the active variable L1 domain with an exon which codes for an vL2 domain selectable in FACS, for example, two specific recombination signals being simultaneously introduced (FRT0 and FRT3) which are recognized by Flp recombinase (as in FIG. 3), and
- V. the exchange of the exon for the active variable vH1 domain with an exon which codes for a vH2 domain selectable in FACS, for example, two specific recombination signals being simultaneously introduced (loxP1 and loxP2) which are recognized by Cre recombinase (as in FIG. 3).

FIG. 5

Specific recombination. Chromosomal DNA sequences or defined gene loci can be modified with comparatively high efficiency by means of specific recombination. Here, DNAs recombine under the influence of a recombinase, such as Cre or Flp, at specific recombination signals so as to also exchange the DNA sequences flanked by these signals. In this kind of cassette exchange, the DNA to be exchanged is flanked in each case by two different recombination signals which do not react with each other. The figure shows the cassette exchange of DNA sequences by means of Cre or Flp. After the transfection of suitable chimeric, in particular circular, DNA (shown above the chromosomal DNA), the circular DNA initially integrates into the chromosome by recombination to one of the two specific recombination signals (shown by crossed lines). Thereafter, an also circular DNA is excised on account of the recombinase action (not shown). This is done randomly, either at the same recombination signals as in the integration or at the two other recombination signals. As a result, an equilibrium of original and exchanged DNA sequences adjusts. If a modified antibody is then presented on the surface (see also FIG. 2), the corresponding cell can be isolated by means of FACS. The figure shows:

- VI. The exchange of the exon for a defined vkappa domain with an exon from a group of different exons each coding for different vkappa domains,
- VII. the exchange of the exon for a defined vlambda domain with an exon from a group of different exons, each coding for different lambda domains, and
- VIII. the exchange of the exon for a defined vH domain with an exon from a group of different exons each coding for different vH domains.

If the specific recombination events VI and VIII or VII and VIII shown in the figures are carried out one after the other and the corresponding group of cells is enriched, a hybridoma antibody library will be established whose individual representatives (cells) each present a comparatively large number of a defined monoclonal antibody on their surface. Hybridoma cells isolated therefrom produce monoclonal, in particular human, antibodies in good yield and quality.

FIG. 6

Figure 6:
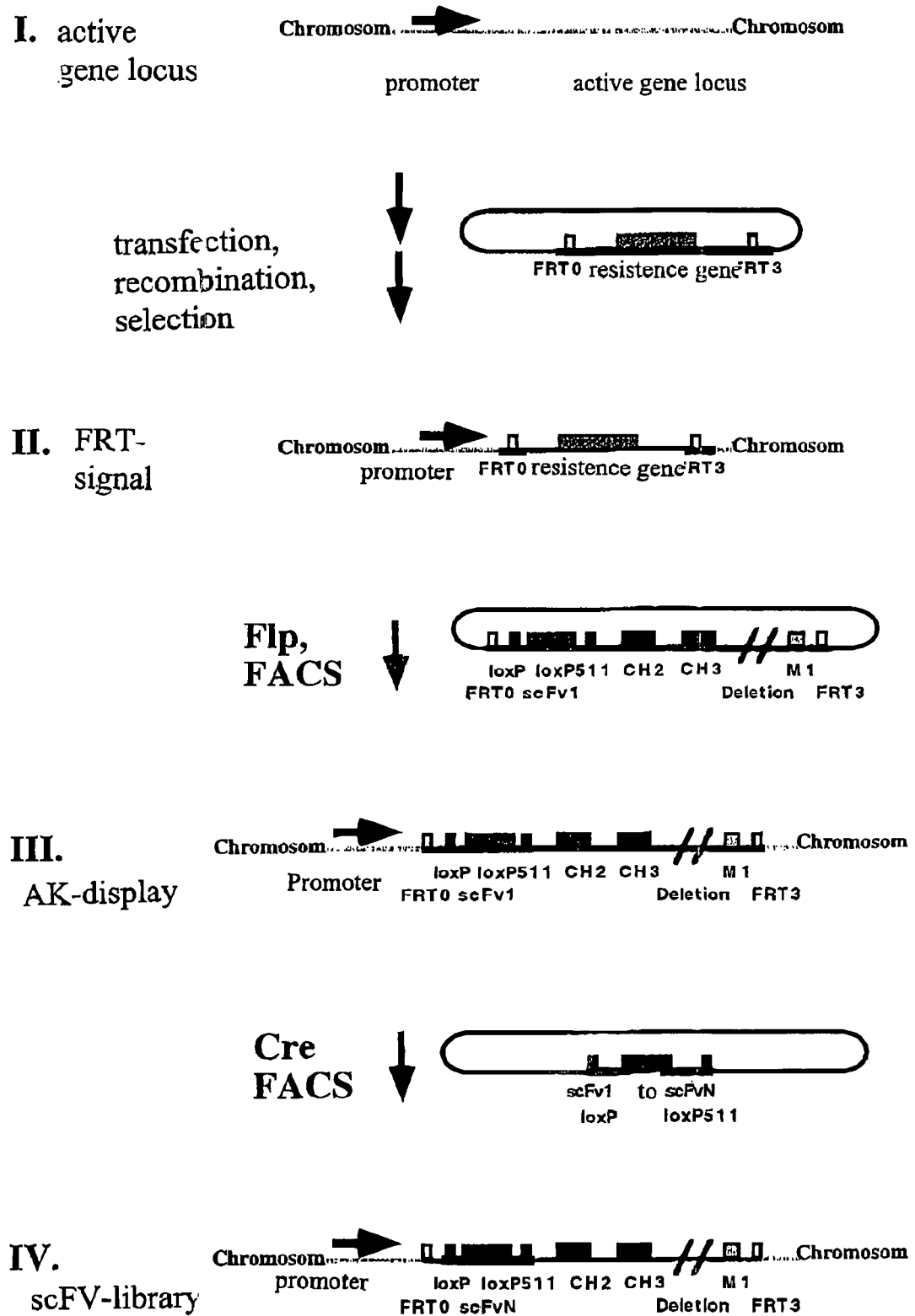

Introduction of specific recombination signals into active gene loci. The figure shows:

- I. The transfection of a cell line with vector DNA which codes for a resistance gene (e.g. G418 resistance) flanked by 2 different FRT sites, and the selection (e.g. by G418) of a cell line carrying the resistance gene together with the FRT sites chromosomally while integrated in an active gene locus;
- II. the cassette exchange of the resistance gene by means of specific recombination by Flp with DNA sequences which encode the Hinge (not shown), CH2, CH3, M1 and optionally M2 exons of an IgG antibody while fused to a first gene of a first scFv antibody (see also FIG. 2). The gene of the first scFv antibody is flanked by two different loxP sites. This recombination event is selected e.g. in a FACS by the surface presentation of the svFv antibody fusion protein on the cell surface;
- III. the exchange of the first gene of a first scFv antibody with another gene from a group of further genes of further scFv antibodies by means of Cre;
- IV. if the recombination events I, II and III shown in the figure are carried out one after the other and the corresponding group of cells is enriched, an scFv antibody library will result, whose individual representatives (cells) present in each case a comparatively large number of a defined monoclonal scFv antibody on their surface. Cells isolated therefrom produce monoclonal, in particular human, scFv-CH2-CH3 antibodies in good yield and quality.

Where appropriate, the circular DNA sequence having a first scFv antibody gene and shown in FIG. 6, II., can contain further scFV antibody genes flanked by a loxP site and a loxP511 site each (e.g. loxP scFv1 loxP511 loxP scFv2 loxP511 . . . loxP scFvN loxP511). Thus, a recombined DNA sequence results in many different antibody-presenting cells by the Cre activity within this cell. Said plurality can be intensified by a combination of a plurality of vH exons and vL exons.

FIG. 7

Humanization of a murine hybridoma cell line (2) by homologous recombination. The phenotype of different modified hybridoma cells (2Kh, 2h, 2H) is shown after carrying out the homologous recombination events described in FIG. 3, part (I.) and (II.) or (III.). The very rare homologous recombination events take place in about 1 of $10^7$ cells. The modified cells then have to be selected in a FACS, for example. The center of the figure shows a homologously recombined hybridoma cell (2H) by way of example, where initially the homologous recombination event described in FIG. 3, part (I.) and then that of part (III.) have taken place. The figure shows:

- I. The exchange of the exon for the constant murine kappa domain with an exon which codes for a constant human kappa domain results in the surface presentation of a constant human kappa domain while the antigen specificity of the presented antibody remains constant (2kh),
- II. the exchange of the CH1, CH2 and CH3 exons for the constant murine IgG1 domains with the corresponding exons of the constant human IgG1 domains results in the surface presentation of constant human IgG1 domains while the antigen specificity of the presented antibody remains the same (2h), and
- III. as in (II.), DNA sequences of the intron being additionally deleted between the CD3 domain and M1 domain of the encoded IgG1 (see FIG. 2) so as to present markedly more antibodies on the surface of the hybridoma cell (2H).

If the homologous recombination events I and II or I and III shown in the figure are carried out one after the other and the corresponding cell lines are isolated, a hybridoma cell line will be formed which produces a humanized monoclonal antibody having the original antigen specificity (2H).

FIG. 8

Introduction of specific recombination signals with simultaneous modification of the antibody specificity of a hybridoma cell line (2H) by homologous recombination. The phenotype of the modified hybridoma cells (3aH, 3H) is shown after carrying out the homologous recombination events described in FIG. 3, parts (IV.) and (V.). The modified cells are then selected in FACS, for example. The initial cell line (2H) is described in FIG. 7. The center of the figure shows a homologously recombined hybridoma cell (3H) by way of example, where initially the homologous recombination event described in FIG. 3, item (IV.) and then that of item (V.) have taken place. The figure shows:

IV. The exchange of the exon for the active variable vL1 domain with an exon which codes for a vL2 domain which can be selected in a FACS, for example, results in the surface presentation of a modified vL domain so as to modify the antigen specificity of the presented antibody (3aH) while 2 FRT sites are simultaneously introduced, and V. the subsequent exchange of the exon for the active variable vH1 domain with an exon which codes for a vH2 domain which can be selected in a FACS, for example, results in the surface presentation of a modified vH domain so as to modify the antigen specificity of the presented antibody (3H) while 2 loxP sites are simultaneously introduced.

If the homologous recombination events IV and V as shown (also in FIG. 3) are carried out one after the other and the corresponding cells are isolated, a modified hybridoma cell line will result which presents a modified humanized monoclonal antibody on its surface. The antigen specificity of this antibody depends on the variable recombined domains.

FIG. 9

Production of a hybridoma antibody library (2H, 3H, 4H, 5H, 6H) by specific recombination. The phenotype of the modified hybridoma cells (2H, 3H, 4H, 5H, 6H) is shown after carrying out initially the homologous recombination events described in FIG. 3, parts (I.), (III.), (IV.) and (V.) and subsequently the specific recombination events described in FIG. 5, parts (VI. & VIII.) or (VII. & VIII.). The initial cell line (3H) has been described in FIG. 8. The hybridoma cell line (3H) shown in FIG. 9 is transfected in each case with a group of different DNA sequences, and then a group of different phenotypes is selected for specific recombination events in a FACS. The figure shows:

IV. The exchange of the exon for the active variable vL3 domain with a group of exons results in the surface presentation of a group of differently modified vL domains, and V. the subsequent exchange of the exon for the active variable H3 domain with a group of exons results in the surface presentation of a group of differently modified vH domains so as to modify the antigen specificity of the presented antibodies (2H, 3H, 4H, 5H, 6H).

If the specific recombination events IV and V shown in the figure are carried out one after the other with a group of cells or a group of different DNA sequences and the corresponding groups of different cells are enriched, a hybridoma antibody library will result whose individual representatives each present different humanized monoclonal antibodies on their surfaces. The initial cells (3H) and incorrectly or unproductively recombined cells (0H) are depleted in this method.

FIG. 10

"On-line" affinity comparison of presented antibodies. The affinity of an antibody for its antigen is a measure of the ration of antibody-bound antigens to free antibodies and free antigens in solution (generally: receptor to ligand). Simultaneously with the selection by means of FACS, this enables a direct affinity comparison of different surface-presenting antibodies or different presented proteins (or the corresponding hybridoma cells) by fluorescence-labeled antigens (red triangles). In order to normalize the number of antibodies each presented per cell, they can be counterstained using FITC-labeled protein G, for example (green circles). In the example as shown, the antibody presented by the hybridoma cell B binds in a markedly more affine way to the antigen in comparison with the antibody presented by cell A. In this case, the measure of the affinity is the quotient of red to green fluorescence of the cells sorted in FACS.

FIG. 11

Somatic hypermutation. First, the exons of the active variable vL2 domain are exchanged with a group of exons each coding for a differently mutated vL2 domain by specific recombination as described in FIG. 9 (see also FIGS. 5 and 6). As a result, unproductive mutations (2d), antibodies having reduced affinity (2c and 2e) and in rare cases antibodies having increased affinity (2b) are formed. As described in FIG. 10, they can be sorted in a FACS. Alternatively, the expression of RAD54, RecQ4 and simultaneously of polX mu within the hybridoma cell line (2) results in an introduction of non-directed mutations within about 1.5 kb downstream of the particular promoters for the active light and heavy antibody chain. Preferably, anti-sense RNA or siRNA is simultaneously expressed against XRCC2, XRCC3 or RAD51B. A precondition for this alternative route for the introduction of somatic hypermutations is the context of the active antibody gene locus.

FIG. 12

Chimeric mouse-man DNA for the humanization of the hybridoma cell line HEA125.

A. Humanization of the constant kappa domain by means of the DNA vector pBS MhKappaM. The vector pBS MhKappaM is shown with the chimeric DNA sequences for the humanization of the constant kappa domain of the hybridoma cell line HEA125. The cloning vector is pBSIISK+ from Stratagene company. Restriction sites are underlined. Sequencing primers are shown in blue. The cyan and underlined PCR primers HK1 and HK2 served for the multiplication of the human exon which codes for the constant kappa chain. Template DNA is here human genomic DNA. The coding sequence of the constant human kappa domain exon is green and written in small letters. The red PCR primers MK1 and MK2 or MK3 and MK4, which are written in small letters, served for multiplying the flanking homologous regions of the murine genome of HEA125. The template DNA was here the genomic DNA of HEA125. The boundary between murine and human sequences is marked by the restriction sites NotI and BstB1, respectively. Prior to electroporation in HEA125 cells, the vector DNA is linearized with the restriction enzyme BglI. The cyan and underlined PCR primers HK3 and HK4 serve (in combination with the surface presentation of humanized antibodies) for sequencing and verifying the subclones changed by homologous recombination of the hybridoma cell HEA125.

B. Humanization of the constant IgG1-$CH_1$, CH2 and CH3 domains by means of the DNA vector pBS MhIgG1M. The vector pBS MhIgG1M with the chimeric DNA sequences for humanization of the constant IgG1-CH1, CH2 and CH3 domains of the hybridoma cell line HEA125 is shown. The cloning vector is PBSIISK+ from Stratagene company. Restriction sites are underlined. The cyan PCR and underlined primers HG1 and HG2 serve for multiplying the human exons which code for the constant IgG1 domains. The template DNA is here human genomic DNA. The red PCR primers MG1 and MG2 or MG3 and MG4, written in small letters, serve for multiplying the flanking homologous regions of the murine HEA125 genome. The template DNA is here the genomic DNA of HEA125. The boundary between murine and human sequences is marked by two HindIII restriction sites. Coding human sequences and the murine M1 and murine M2 exons are written in green small letters. Prior to the electroporation in HEA125 cells, the vector DNA is linearized using the restriction enzyme SspI. The cyan and underlined PCR primers HG3 and HG4 serve (in combination with the surface presentation of humanized antibodies) for sequencing and verifying the subclones, modified by homologous recombination, of the hybridoma cell HEA125.

5 different primers are underlined, blue and in italics (primers delta1 to delta5). By means of them it is possible to delete DNA sequences having a length of between about 350 bp and about 900 bp and located between the next HindIII site and the particular primers. For this purpose, a PCR is carried out with primer MG4 and the particular primers delta1 to delta5. They have an additional HindIII overhang which is not shown. As a result, the 5 PCR bands can be ligated into the vector pBS MhIgG1M excised by HindIII (partial digestion) and EagI. The resulting deletions in the intron between the CH3 and M1 domains lead to an enhanced surface expression. The pBS MhIgG1Mdelta350 vector is identical with the pBS MhIgG1M vector, it only lacks the sequences between primers MG3 (including the MG3 primer sequences) and delta1 (excluding the delat1 primer sequences).

FIG. 13

Chimeric murine G418 resistance DNA for introducing specific recombination signals into the vH and vkappa gene locus of the hybridoma cell line HEA125.

A. Insertion of FRT sites in the vkappa gene locus of the hybridoma cell line HEA125 by means of the DNA vector pBS MKappaG418M. The vector pBS MKappaG418M with the chimeric DNA sequences for the insertion of FRT sites in the active vkappa gene locus of the hybridoma cell line HEA125 is shown. The cloning vector is PBSIISK+ from Stratagene company. Restriction sites are underlined. The resistance gene PGKneo is multiplied using the PCR primers Neo1 and Neo2 (underlined and written in red small letters) and subsequently cloned in by means of AatII. Here, the vector ploxPfrtPGKneofrtloxP serves as a source or template for the PGKneo resistance gene (Dr. Erich Greiner, dkfz, Department: Molecular Cell Biology I). The coding sequence of the neophosphoryl transferase II gene and the murine vkappa leader exon is green and written in small letters. The neophosphoryl transferase II gene is controlled by the promoter for phosphoglycerin kinase (PGK; cyan and in italics). The PCR primers MVK1 and MVK2 or MVK3 and MVK4, shown in red and small letters, serve for multiplying the homologous regions, flanking the vkappa domain, of the murine HEA125 genome. The template DNA is here genomic DNA of HEA125. Said primers additionally carry along in a subsequent PCR the sequences of the respectively flanking FRT site and half an AatII site. The boundary between murine and PGKneo sequences is marked by the FRT0 and/or FRT3 sites shown in blue and in italics. The vector DNA is linearized prior to the electroporation in HEA125 cells. The cyan and underlined PCR primers KG418-3 and KG418-4 (and primers outside the regions as shown) serve for sequencing and verifying the subclones, modified by homologous recombination, of the HEA125 hybridoma cell.

B. Insertion of loxP sites in the vH gene locus of the hybridoma cell line HEA125 by means of the pBS MvHG418M vector. The vector pBS MvHG418M with the chimeric DNA sequences for inserting loxP sites in the active vH gene locus of the hybridoma HEA125 cell line is shown. The cloning vector is PBSIISK+ from Stratagene company. Restriction sites are underlined. The resistance gene PGKneo is cloned in using AatII, the source of the DNA is the same as shown in (A.). The coding sequence of the neophosphoryl transferase II gene is green and written in small letters. The PGK promoter is cyan and written in italics. The vector pBS MvHG418MdeltaPGK lacks the PGK promoter sequences shown in cyan and in italics, as for the rest, this vector is identical with pBS MvHG418M. In order to produce this vector, the neophosphoryl transferase II gene is multiplied with the PCR primers Neo2 and Neo3 (underlined and written in red and small letters). Here, the primers carry along in each case overhanging AatII sites at the 5' end. The template is here the ploxPfrtPGKneofrtloxP vector. The PCR primers MvH1 and MvH2 or MvH3 and MvH4, which are written in red and small letters, serve for multiplying the homologous regions, flanking the vH domain, of the murine HEA125 genome. The template DNA is here the genomic DNA of HEA125. Said primers carry along in a downstream PCR additionally the sequences of respectively flanking loxP site and half an AatII site. The boundary between murine genomic and PGKneo sequences is marked by the loxP and/or loxP511 sites shown in blue and in italics. The vector rDNA is linearized prior to the electroporation in HEA125 cells. The cyan and underlined PCR primers vHG418-3 and vHG418-4 (and primers outside the regions as shown) serve for sequencing and verifying the hybridoma cell HEA125 subclones modified by homologous recombination.

FIG. 14

Primers for multiplying the plurality of genomically recombined human antibody genes. Shown are primers with which the genomic DNA of the corresponding variable genes can be multiplied. The associated J segment primers serve as counterstrand primers. The human gene sequences were identified by means of the book Immunoglobulin Facts Book (Lefranc and Lefranc, 2001, Academic Press, ISBN 0-12-441351-X). The DNA sequences of the variable antibody genes listed therein were imported by means of the accession numbers from the publicly available database Genbank and then vH gene-specific primers were designed. They hybridize in each case about 182 by away from the 5' end of the ATG start codon of the leader exon. Analogous steps were taken with vkappa-specific and vlambda-specific PCR primers. They hybridize within the intron between leader exon and vL exon. The 5' ends of these primers hybridize in each case about 130 bp away from the 5' end of the vL exon. The 5' ends of the $J_H$ segment-specific counterstrand primers hybridize about 83 bp away from the 3' end of the $J_H$ segments in the 3' direction. The 5' ends of the $J_{kappa}$ and $J_{lambda}$ segment-specific counterstrand primers hybridize about 89 bp away from the 3' end of the $J_L$ segments in the 3' direction. The following PCRs are carried out at 65° C. (+/−5° C.) with the listed PCR primers and, genomic DNA from human peripheral lymphocytes as templates:

4 $J_{lambda}$ segments×24 vlambda genes=96 vlambda-specific PCRs;

5 $J_{kappa}$ segments×35 vkappa genes=170 vkappa-specific PCRs; and

6 $J_H$ segmemts×44 vH genes=264 vH-specific PCRs,

A. human vlambda primers and $J_{lambda}$ primers (SEQ ID NOs:110-137)

B. human vkappa primers and $J_{kappa}$ primers (SEQ ID NOs:71-109)

C. human vH primers and $J_H$ primers (SEQ ID NO:21-70).

FIG. 15

Vector for the insertion of variable exons in the vH and vkappa gene locus of the hybridoma cell line HEA125 by means of specific recombination.

A. Shown is the vector pBS FRTvKappa by which by means of Flp the original vkappa domain of HEA125 can be recombined again into the vkappa gene locus of the hybridoma cell line HEA125. Restriction sites are underlined. The coding sequences of the vkappa exon are green and written in small letters. The PCR primers vKHEA1 and vKHEA2 which are written in red and small letters, serve for multiplying the genomic DNA of the active vkappa gene of HEA125. The template DNA is here genomic DNA of HEA125. Said primers carry along in a downstream PCR additionally the sequences of the respectively flanking FRT site and a BssHII site. The PCR fragment is cloned in pBSIISK+ by means of BssHII. The boundary of the genomic vkappa sequences is marked by the FRT0 and/or FRT3 sites shown in blue and in italics. The PCR primers KG418-3 and KG418-4 underlined and written in cyan in FIG. 13A, serve for sequencing and verifying the subclones, modified by specific recombination, of the HEA125 hybridoma cell. The sequence of the active HEA125-vkappa gene locus results from FIGS. 15A (active gnomically recombined vkappa exon) and 13A (5' and 3' flanking regions), two additional FRT sites which are not present in the HEA125 genome being shown in the figures).

B. Shown is the vector pBS loxPvHmyc, by which by means of Cre the original vH domain of HEA 125 (+myc-tag) can be recombined again into the vH gene locus of the hybridoma cell line HEAs125. Restriction sites are underlined. The coding sequences of the leader exon and the vH exon are shown in green and in small letters. The PCR primers vHEA1 and vHEA2 shown in red and small letters serve for multiplying the genomic DNA of the active vH gene of HEA125. The template DNA is here genomic DNA from HEA125. Said primers carry along in a subsequent PCR additionally the sequences of the respectively flanking loxP site and a BssHII site. The PCR fragment is cloned into pBSIISK+ by means of BssHII. The boundary of the genomic vH sequences is marked by the loxP and/or loxP511 sites shown in italics and in blue. In addition to the sequences naturally occurring in HEA125, a magenta and underlined myc-tag is inserted in the CDR3 region. For this purpose, the illustrated DNA sequence is synthesized and cloned in by means of the flanking restriction sites BsmB1 and BglII. Apart from this myc-tag, the pBS loxPvH vector is identical with the pBS loxPvHmyc vector.

The PCR primers vHG418-3 and vHG418-4, which are underlined and shown in cyan in FIG. 13B, serve for sequencing and verifying the subclones modified by specific recombination of the hybridoma cell HEA125.

The sequence of the active HEA125-vH gene locus results from FIGS. 15B (active genomically recombined vH exon) and 13B (5' and 3' flanking regions), two additional loxP sites which do not exist in the HEA125 genome being shown in the figures. In addition, FIG. 15B shows in the CDR3 of the vH domain a myc-tag which is not present in the original HEA125 genome either.

C. The cloning vector pBS FRTclone is shown (SEQ ID NO:14).

D. The cloning vector pBS loxPclone is shown (SEQ ID NO:15).

FIG. 16

Vector for the insertion of specific recombination signals in pre-selected gene loci. Shown is the vector pBS loxP-IgG1 by which by means of Flp the constant domains including the membrane domains M1 and M2 of an IgG1 can be recombined into a pre-selected FRT cassette, for example. In addition, this vector carries along a loxP cassette into which e.g. variable domains can be recombined by means of Cre. The cloning vector is initially the pBS FRTvKappa vector excised using AatII (FIG. 15A). Synthetic oligonucleotide sequences are added thereto, which encode the loxP and loxP511 sites with an additional BamH1 site. The resulting vector is excised using BamH1. The cyan and underlined PCR primers hIgG1-1 and hIgG1-2 serve for multiplying a chimeric genomic IgG1 gene. These primers carry along in a downstream PCR reaction one BamH1 site each. The template DNA is here the pBS MhIgG1M vector described in FIG. 12B (alternatively pBS MhIgG1Mdelta350). Following ligation of this PCR band also BamH1-digested, the vector pBS loxP-IgG1 and alternatively the vector pBS loxP-IgG1delta350 are formed. Restriction sites are underlined. The boundary between murine and human sequences is marked by the HindIII restriction site. Coding human sequences and the murine M1 and murine M2 exons are shown in green small letters. The splice acceptor at the 5' end of the hinge exon is underlined and red.

Based on the pBS loxP-IgG1 vector, the vector pBS loxP-IgG1deltaCH1 is obtained. Both vectors are identical, the vector pBS loxP-IgG1deltaCH1 only lacks the DNA sequences between the PfMl and BamH1 sites. For this purpose, the vector pBS loxP-IgG1 is excised using BamH1 and a fragment obtained by means of the PCR primer deltaCH1-1 and hIgG1-2 was cloned in. Here, the pBS loxP-IgG1 vector serves as a DNA template.

FIG. 17

(A) Bispecific antibodies. Shown is the pBS FRT Kappa-HEAscFv215 vector by which by means of Flp a chimeric gene can be recombined into the active vkappa gene locus of the hybridoma cell line HEA125-mhloxPmycFrTG418 (Example 12). Under the control of the kappa promoter (with endogenous leader exon) and the kappa enhancer located in the adjacent intron (before the endogenous ckappa exon) this chimeric gene encodes:

the vkappa domain of HEA125 (small letters);

fused to the ckappa mouse domain of HEA125 (capital letters);

fused to a linker sequence (in italics);

fused to the vH domain of the scFv antibody 215 (small letters);

fused to a GlySer linker (in italics);

fused to the vkappa domain of the scFv antibody 215 (small letters); and finally fused to a myc-tag and a His-tag (each in italics).

Restrictions sites are underlined. The PvuII/MscI restriction site shown in parentheses contains residual sequences resulting from cloning. The PCR primers vHEAcDNA1 and vHEAcDNA2 shown in red and small letters serve for multiplying the cDNA of the active kappa gene of HEA125. The template DNA is here the cDNA of HEA125. The primer vHEAcDNA2 carried carries along in a downstream PCR additionally the sequences of the shown flanking linker up to the PvuII site inclusive. This PCR fragment is ligated into the MscI-cleaved cloning vector pBS FRTvKappa (see FIG. 15A). Thereafter, the resulting vector pBS FRT KappaHEAP-vuII is excised using PvuII. The PCR primers svFv1 and scFv2 shown in red and small letters, serve for multiplying the coding DNA of the scFv antibody. The template DNA is here the pOPE101-215 plasmid. Having cloned in this PCR fragment, the vector pBS FRT KappaHEAscFv215 results.

B. Bifunctional antibody. Shown is the pBS FRT Kappa-HEAbla vector by which a bifunctional chimeric gene can be recombined into the active vkappa gene locus of the hybridoma cell line HEA125-mhloxPmycFRTG418 by means of Flp (Example 13). Under the control of the kappa promoter (with endogenous leader exon) and the kappa enhancer located in the adjacent intron (before the endogenous ckappa exon) this chimeric gene encodes:

the vkappa domain of HEA125 (green small letters);
fused to the ckappa mouse domain of HEA125 (blue capital letters);
fused to a linker sequence (in italics, magenta); and
fused to the coding sequence of the beta lactamase (green small letters).

Restriction sites are underlined. The restriction sites PvuII and/or PvuII/MscI which are written in parentheses contain residual sequences resulting from cloning. The starting point is the PvuII-cleaved vector pBS FRT KappaHEAPvuII which is described in FIG. 17A. The PCR primers bla1 and bla2 shown in red and small letters, serve for multiplying the coding DNA of beta-lactamase. The template DNA is here the PBSIISK+ plasmid. Having cloned in this PCR fragment, the pBS FRT KappaHEAbla vector is formed.

FIG. 18

Further examples of modified antibodies presented by hybridoma cells.

A. Modified antibody specificity by means of specific recombination. Shown is the pBS FRT vKappa215 vector by which by means of Flp a modified vkappa exon can be recombined into the active vkappa gene locus of the hybridoma cell line HEA125-mhloxPmycFRTG418 (Example 14). Under the control of the kappa promoter (with endogenous leader exon) and the kappa enhancer located in the adjacent intron (before the endogenous ckappa exon) this exon codes for the vkappa domain of the 215 antibody (Kontermann et al., 1995, Characterization of the epitope recognised by a monoclonal antibody directed against the largest subunit of *Drosophila* RNA polymerase II. Biol. Chem. Hoppe-Seyler 376, 473-481; green small letters). This vkappa domain is combined by splicing with the ckappa domain encoded endogenously by HEA125. Restriction sites are underlined. The PCR primers K215-1 and K215-2 shown in red and small letters, serve for multiplying the vkappa(215) domain. The PCR primer K215-1 here carries along a silent point mutation which serves for inserting an EcoRV site. The template DNA is here the plasmid pOPE101-215 (see FIG. 17A). This PCR fragment is ligated into the EarI and AvaII-excised vector pBS FRTvKappa (see FIG. 15A). The vector pBS FRT vkappa215 is thus formed.

B. Fab antibody by means of specific recombination. Shown is the vector pBS loxP-FdHEA by which by means of Cre a modified vH exon can be recombined into the active vH gene locus of the hybridoma cell line HEA125-mhRek (Example 15). This exon codes for the vH domain of the HEA125 antibody under the control of the vH promoter and the IgG1 enhancer located in the adjacent intron (before the endogenous CH1 exon) (green small letters). This vH domain is combined by splicing with the adjacent IgG1-CH1 domain (green small letters). Restriction sites are underlined. The PCR primers Fd1 and Fd2 which are written in red and small letters, serve for multiplying the IgG1-CH1 domain. The PCR primer Fd2 here carries along a stop codon and a SalI site. The template DNA is here the genomic DNA of HEA125. This PCR fragment is ligated into the SalI-excised vector pBS loxPvH (see FIG. 15B). As a result, the pBS loxP-FdHEA vector is formed.

ABBREVIATIONS

Ag8 myeloma cell line X63AG8.653
Antibody library a plurality (>100) of antibody-producing cells and/or of the corresponding antibody genes and proteins
Antibody database see antibody library
bla beta-lactamase, gene for
Bp, bp base pairs
Antigen ligand binding specifically an antibody; within the meaning of this invention also a ligand binding specifically to a receptor
Antibody protein binding specifically an antigen; within the meaning of this invention also more generally a protein binding specifically a ligand
cH constant domains of the heavy antibody chain, gene therefor
CH1 first constant immunoglobulin domain (IgG, IgA, IgE, IgD, IgM), exon therefor
CH2 second constant immunoglobulin domain (IgG, IgA, IgE, IgD, IgM), exon therefore
CH3 third constant immunoglobulin domain (IgG, IgA, IgE, IgD; IgM), exon therefore
CH4 fourth constant immunoglobulin domain (IgE, IgM), exon therefore
cL constant domain of the light antibody chain, gene therefore
D D segment of the vH domain
DMSO dimethylsulfoxide
downstream based on the 3' end of a DNA sequence in the 3' direction
e enhancer
Fab antibody part consisting of a light chain, vH and CH1 domains, gene therefore
FACS Florescence Activated Cell Sorting
FRT Flp Recognition Targets

```
                                         (SEQ ID NO: 146)
FRT0    GAAGTTCCTATTCTCTAGAAAGTATAGGAACTTC (SEQ ID NO: 147)
FRT3    GAAGTTCCTATTCTTCAAATAGTATAGGAACTTC
```

G418 see Neo
H hinge, hinge exon
His-tag a sequence of 5 or 6 histidines suited for affinity purification per NiChelate; DNA sequences therefore
$J_H$ joining segment of the vH domain, gene segment therefore
$J_{lambda}$ joining segment of the vlambda domain; gene segment therefore
$J_{kappa}$ joining segment of the vkappa domain, gene segment therefore
L leader, signal peptide, exon therefore;
the leader exons of the antibody genes only code for the N-terminal part of the leader peptide
loxP DNA sequences recognized by Cre recombinase

| | | (SEQ ID NO: 148) |
|---|---|---|
| lox66 site | TACCGTTCGTATAATGTATGCTATACGAAGTTAT | |
| | | (SEQ ID NO: 149) |
| lox71 site | ATAACTTCGTATAATGTATGCTATACGAACGGTA | |
| | | (SEQ ID NO: 150) |
| loxP site | ATAACTTCGTATAATGTATGCTATACGAAGTTAT | |
| | | (SEQ ID NO: 151) |
| loxP511 site | ATAACTTCGTATAATGTATACTATACGAAGTTAT | |
| | | (SEQ ID NO: 152) |
| loxG site | ATAACTTCGTATAGCATACATTATACGAAGTTGC | |

M membrane domain of an immunoglobulin (IgA1, IgA2), exon therefore

M1 first membrane domain of an immunoglobulin (IgG, IgE, IgD, IgM), exon therefore M2 second membrane domain of an immunoglobulin (IgG, IgE, IgD, IgM), exon therefore mIgG1 membrane-bound IgG1; mRNA therefore myc-tag peptide sequence which is recognized by the monoclonal 1-9E10 antibody; DNA sequences therefore Myeloma fusion partner for the production of a hybridoma; descendent of a plasmacytoma cell line Neo the neophosphoryl transferase II gene conveys resistance to neomycin or to G418, gene therefor P promoter pBS185 Cre expression vector from Life Technologies (Gibco-BRL) #10347-011

PEG polyethylene glycol pGH-1 neo gene and HSV-tk gene flanked by a loxP site; Gu and Rajewsky, 1993, Cell 73, 1155-1164

PGK phosphoglycerin kinase

PGKneo neo (G418) resistance gene under the control of the PGK promoter pMC-Cre Cre expression vector; Gu and Rajewsky, 1993, Cell 73, 1155-1164; see also Transgenic Animal Web: www.med.umich.edu/tamc/mta.html pIC-Cre Cre expression vector; Gu and Rajewsky, 1993, Cell 73, 1155-1164 pOG44 Flp expression vector from Invitrogen company, order number V6005-20 or from the kit Flp-In™ pcDNA5/FRT Core order number K6010-02 polX mu EMBL database accession number AJ251804 (mouse), AJ131891 (homo sapiens); complete mRNA pOPE101-215 EMBL database accession number ASY14585; synthetic gene of an scFv(215) antibody; see also Kontermann et al., 1995, Biol. Chem. Hoppe-Seyler 376, 473-481 pREP4 Invitrogen V004-50; plasmid replicating episomally in mammalian cells, selectable by hygromycin pSH47 EMBL database accession number AF298782; Cre expression vector for yeast pSVlacZT Cre recombination substrate vector for the detection of Cre activity; Torres and Kuhn Laboratory Protocols for Conditional Gene Targeting, 1997, Oxford University Press, ISBN 0-19-963677-X Protein G antibody binding protein for the detection of the constant antibody domains RAD 54 EMBL database accession number BC001965; complete mRNA RAD51B EMBL database accession number U84138; complete mRNA RecQ4 EMBL database accession number AB006532; complete mRNA scFv, scFvn single chain Fv antibody sIgG1 secreted IgG1; mRNA therefore Stop stop codon upstream based on the 5' end of a DNA sequence in the 5' direction vH, vH1, vHn variable domain of the heavy antibody chain vL, vL1, vLn variable domain of the light antibody chain vlambda variable domain of the light lambda antibody chain vkappa variable domain of the light kappa antibody chain XRCC2 EMBL database accession number AF035587; complete mRNA XRCC3 EMBL database accession number AF035586; complete mRNA.

DETAILED DESCRIPTION OF THE INVENTION

Figure 5:
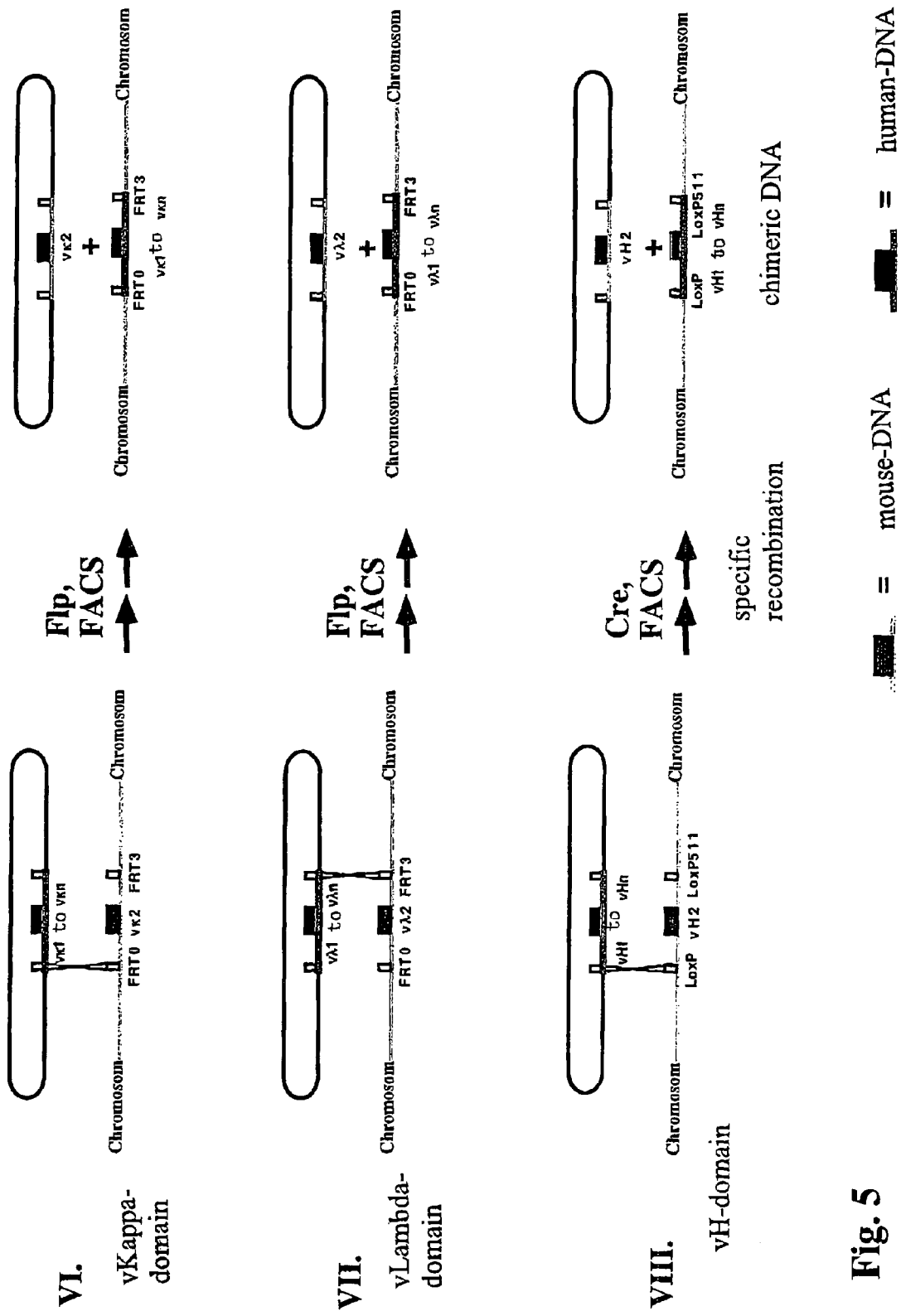

A first aspect of the present invention is thus a method of producing a protein library, in particular a human antibody library (FIGS. 5, 6, 9), the method being characterized by:

initially inserting specific recombination signals in one or two active gene loci, in particular in the expressed vH and vL genes of a B cell line (i.e. acceptors for DNA sequences are generated; FIGS. 3, 4, 6), in particular by homologous recombination (FIGS. 3, 4);

expanding the resulting cell line;

multiplying a plurality of different gene fragments by a comparatively small number of gene segment-specific PCR primers, in particular by vH, vkappa and vlambda-specific primers and by $J_H$, $J_{kappa}$ and $J_{lambda}$ segment specific counterprimers (FIG. 14);

flanking the plurality of the multiplied gene fragments with specific recombination signals each (i.e. donor DNA sequences are generated; FIGS. 5, 6);

transfecting said plurality of multiplied gene fragments into said cell line where a plurality of specific recombination events (FIGS. 5, 6) occur within said active gene loci under the influence of a specific recombinase, in particular of Cre or Flp; and forming on account of the specific recombination events many different cells, each having different proteins, in particular antibodies, modified with respect to the starting cell on the surface of the particular cell surface (FIG. 9).

Another aspect of this invention relates to a method by which already existing genes, in particular antibody genes or groups of antibody genes, can be modified advantageously and readily in the context of their chromosomal gene locus, in particular to obtain more affine (FIGS. 10, 11), bispecific (FIG. 17A) or bifunctional (FIG. 17B) antibodies. This method is characterized in that said genes, in particular antibody genes, are mutated or modified in particular in a non-directed way or are exchanged with a group of similar genes or gene fragments;

said mutated genes code for a protein which is presented on the surface of the cell encoding them; and this surface presentation is utilized for the selection of the modified cell containing the mutation(s).

Figure 7:
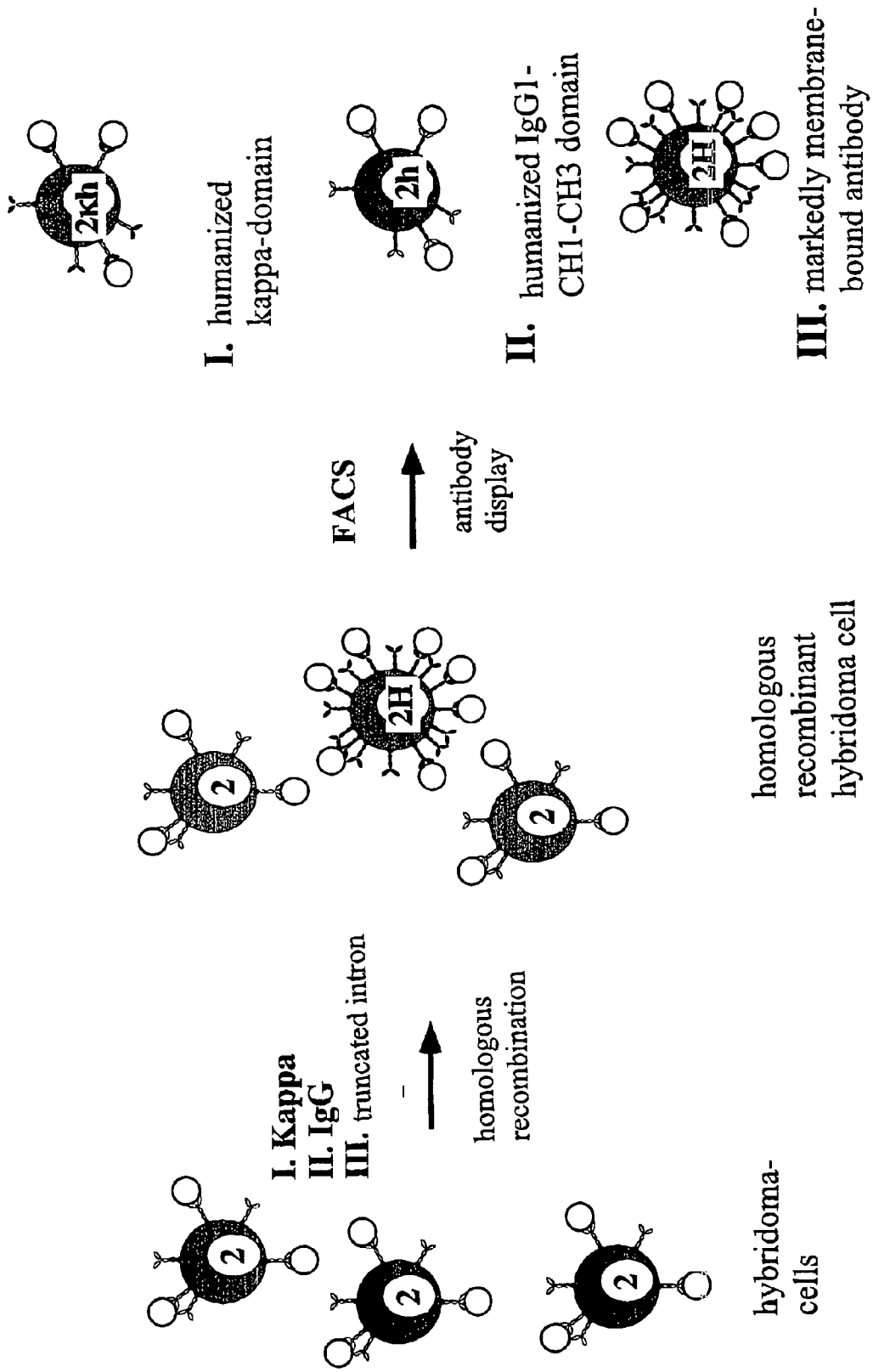

Finally, the present invention relates to a method by which already existing murine hybridoma cells can be modified, in particular humanized, advantageously and readily (FIGS. 3, 7). This method is characterized in that said hybridoma cells are modified by a homologous recombination within the active antibody locus without a disturbing resistance marker being used;

said homologous recombination results in a modified gene product, in particular in a humanized antibody;

said modified gene product, in particular the humanized antibody, is presented on the surface of said hybridoma cell modified by homologous recombination, and this surface presentation is utilized for the selection of the modified cell.

In a first embodiment, the present invention thus relates to a method of producing a library of protein-producing eukaryotic cells, which is characterized by (a) initially introducing specific recombination signals into one or two chromosomal gene loci of the cells;

(b) expanding at least one of the thus modified cells which as a modification exhibits said specific recombination signals in the gene loci;

(c) transfecting into the expanded cells a plurality of different DNA sequences, each flanked by specific recombination signals; and (d) integrating said plurality of different DNA sequences into said gene loci of said expanded cells on account of the specific recombination signals and the recombinase specific thereto, a plurality of cells forming, each expressing different proteins each encoded by the different DNA sequences integrated into the gene loci, and the expressed proteins being bound to the surface of the particular cells expressing them.

In a preferred embodiment, the method according to the invention is characterized by carrying out in step (a) the introduction of the recombination signals by homologous recombination of transfected DNA with the particular gene loci and flanking the recombination signals of the transfected DNA by regions homologous to the particlar gene loci of the cell, and expanding in step (b) at least one of the cells modified by homologous recombination and showing the specific recombination signals in the gene loci as a modification.

Another preferred embodiment of the above method relates to a method of producing a library of an antibody-producing eukaryotic cells, which is characterized by a) initially introducing specific recombination signals into one or two chromosomal gene loci of the cells;

(b) expanding at least one of the thus modified cells which shows said specific recombination signals in said gene loci as a modification;

(c) transfecting into the expanded cells a plurality of different DNA sequences, each containing different vH genes, vlambda or vkappa genes, each flanked by specific recombination signals; and (d) integrating the plurality of different DNA sequences into the gene loci of the expanded cells on account of the specific recombination signals and the recombinase specific thereto, a plurality of cells forming each expressing different antibodies each encoded by the different DNA sequences integrated into the gene loci, and the expressed antibodies being bound to the surface of the particular cells expressing them.

In order to carry out this method and the below described specific embodiments, a person skilled in the art can proceed according to generally known methods or according to the methods described below and in the examples.

Introduction of Recognition Sites for Recombinases by Homologous Recombination

Figure 8:
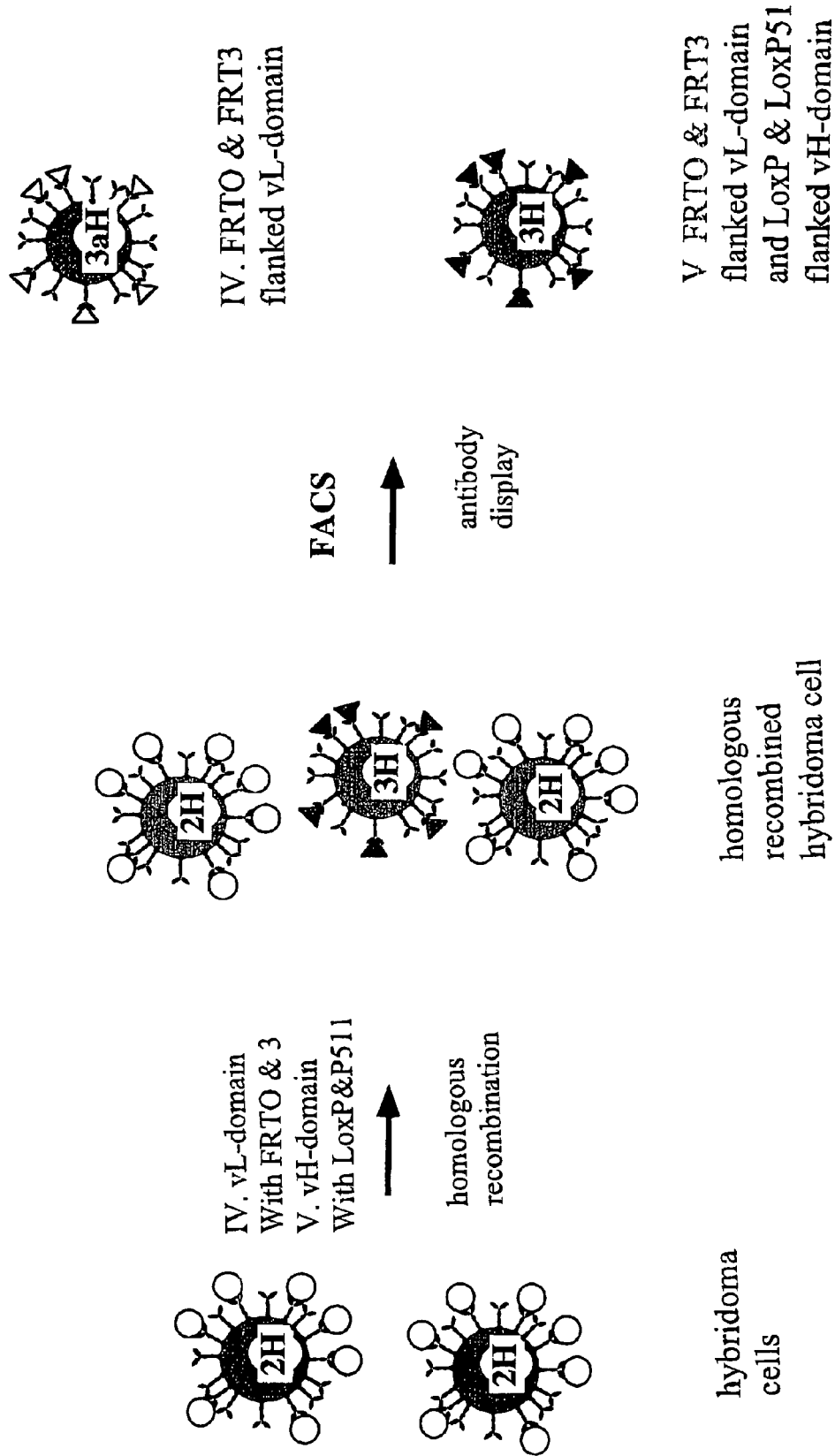
Figure 9:
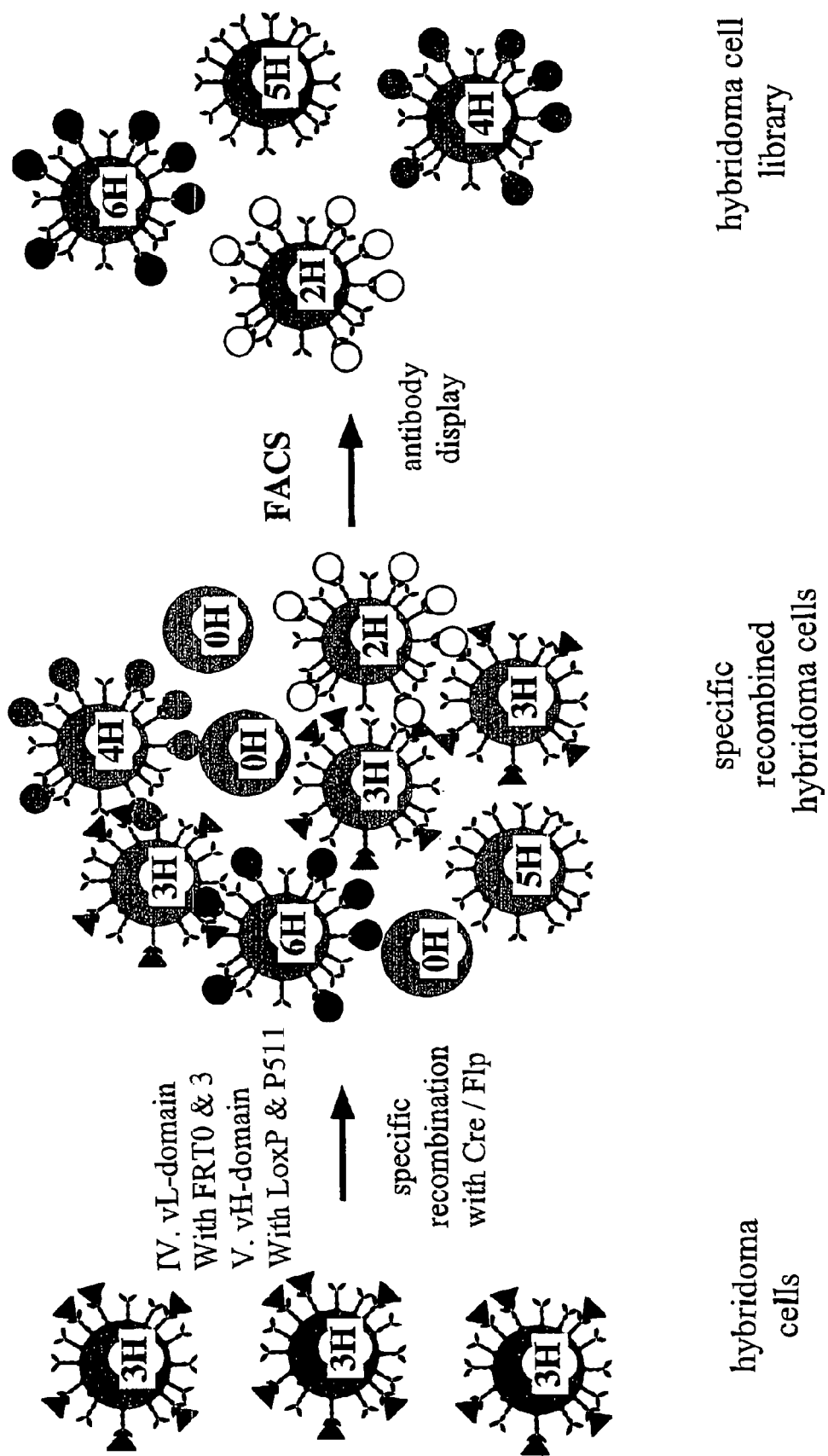

An essential element of the present invention is the insertion of modified DNA sequences, in particular of recognition sequences for recombinases, in the genome of cell lines by means of homologous recombination (FIGS. 3, 4, 8). Here, DNA sequences are exchanged in a defined gene locus. This is achieved by flanking the DNA sequences to be newly introduced from usually >700 bp long regions homologous to the defined gene locus and transfecting them into the cells in this form (usually as a linearized DNA; see Hasty et al., 1992, Mol. Cell. Biol. 12, 2464-2474). In some few cases (about 1 out of $10^7$ cells), the desired homologous recombination then takes place. These rare events or homologously recombined cells then have to be isolated e.g. by means of a resistance marker or by means of a FACS sorter (see below) or ELISA test. The methods required for this (inter alia cloning methods, PCR, sequencing, cell culture of hybridoma cells, homologous recombination, selection by means of G418, FACS) are known to the person skilled in the art and described in a plurality of laboratory manuals (inter alia Sambrook and Russell: Molecular Cloning, a laboratory manual, 3rd Edition, 2001, ISBN 0-87969-577-3). A combination of these or similar methods with the essential element of the homologous recombination of modified DNA sequences into the genome of a cell line is currently used above all for generating transgenic mice or by the modified ES cell lines required for this (Thomas and Capecchi, 1987, Cell 51, 503-512; Thompson et al., 1989, Cell 56, 313-321; Johnson et al., 1989, Science 245, 1234-1236; Doetschman et al., 1987, Nature 330, 576-578; "Transgene Tiere" [transgenic animals] by J. Schenkel, 1995, Spektrum-Verlag ISBN 3860252690; Vasquez et al., 2001, Manipulating the mammalian genome by homologous recombination. PNAS 98, 8403-8410; Torres and Kühn, Laboratory Protocols for Conditional Gene Targeting, 1997, Oxford University Press, ISBN 0-19-963677-X). Specific recognition sites for recombinases are here used inter alia to delete individual exons of defined genes in defined tissues by tissue-specifically induced recombinases. These techniques are adapted to suitable other cell lines, in particular hybridoma cell lines, for the present invention. Homologous recombinations have also already been carried out within hybridoma cell lines (Zou et al., 1994, Current Biology 4, 1099-1103; Shulman et al., 1990, Mol. and Cell. Biology 10, 4466-4472; Sun et al., 1994, J. of Immunology, 152, 695-704; Baker et al., 1994, J. Immunological Methods 168, 25-32; Wood et al., 1991, PNAS 88, 8006-8010; Fell et al., 1989, PNAS 86, 8507-8511).

Specific Recombination

The person skilled in the art also knows suitable recognition sites and the associated recombinases (inter alia Stricklett et al., 1999, The Cre/loxP system and gene targeting in the kidney. Am J Physiol. 276, F651-F657. Review.; Stricklett et al., 1998, Site-specific recombination using an epitope tagged bacteriophage P1 Cre recombinase. Gene. 215, 415-23; Van Duyne, 2001, A structural view of cre-loxp site-specific recombination. Annu Rev Biophys Biomol Struct. 30, 87-104. Review.; Theodosiou and Xu, 1998, Use of FLP/FRT system to study *Drosophila* development. Methods. 4, 355-65. Review.; Sadowski, 1995, The Flp recombinase of the 2-microns plasmid of *Saccharomyces cerevisiae*. Prog Nucleic Acid Res Mol Biol. 51, 53-91. Review.). Examples of suitable systems are:

the Cre-lox system (recombinase Cre, specific recognition sites loxP; see inter alia Creator™ kit from Clontech; U.S. Pat. No. 4,959,317; Griffiths et al., 1994, EMBO Journal 13, 3245-3260);

the Flp system (recombinase Flp, specific recognition sites FRT; O'Gorman et al., 1991, Science 251, 1351-1355; Flp-In™ pcDNA5/FRT Complete Kit from Invitrogen #K60101-01), and the Gateway system (lambda integrase Int and integration host factor IHF, specific recognition sites attBxattP and attLxattR, see inter alia Gateway™ from GibcoBRL/Invitrogen), the Cre-lox system and the Flp system being preferred.

The use of several systems within a cell should be preferred if specific recombination signals shall be introduced into more than one gene locus, i.e. if different acceptors shall be generated for DNA sequences. An example is the vH and vkappa gene loci of a hybridoma cell line which shall be flanked by specific recognition sites for recombinases each (FIG. 5). If they were all recognized by the same recombinase, interferences between the different gene loci or the exchange vectors would occur. This does not apply if 4 different recognition sites which do not recombine (or only recombine to a minor extent) are available, such as e.g. the loxP sites loxP, loxP511, loxG, lox66 and lox71. Then, kind of a recombinase for two gene loci can be used.

The loxP sites (FRT sites are very similar) consist of two 13 bp long inverted repeats which are separated by an 8 bp long spacer. This spacer gives the directionality of the recombined DNA flanked by loxP sites, i.e. the experimentalist can predetermine the accurate chromosomal gene locus and simultaneously the orientation of the recombined DNA by means of a (genomic) loxP or FRT site.

Recombination frequencies higher than in the homologous recombination are usually achieved by an exchange of gene cassettes. Here, the DNA sequences to be exchanged are flanked in both the genome and the exchange vectors by two slightly different loxP or FRT sites which on account of the sequence differences recombine with a corresponding partner but not recombine with one another (FIG. 5). This technique is described for the Flp system in U.S. Pat. No. 5,928,914 and in the publication by Feng et al. (J. Mol. Biol. 1999, 292, 779-785) for the Cre-lox system and in the publications by Seibler and Bode (Biochemistry 1997, 36, 1740-1747; Biochemistry 1994, 33, 12746-12751). A cassette exchange also takes place with genes between two inverted recognition sites having equal identity (e.g. loxP gene Pxol). In this case, the product of a specific recombination may have three forms: 1. The gene between the lox P sites can be inverted. In addition, the gene between the loxP sites can be exchanged with another recombined one, which is integrated 2. in the proper orientation, and 3. in a wrong orientation between the recognition sites. Even if prior to the exchange between the recognition sites no negatively selectable marker is present between the recognition sites, a specific recombination takes place in about 1% of all the cells which survived the transfection (Feng et al., 1999, J. Mol. Biol. 292, 779-785).

Methods and expression vectors by means of which said recombinases can be expressed transiently in eukaryotic cells are also known (Taniguchi et al., 1998, Efficient production of Cre-mediated site-directed recombinants through the utilization of the puromycin resistance gene, pac: a transient gene-integration marker for ES cells. Nucleic Acids Res 26, 679-680; Araki et al., 1997, Efficiency of recombination by Cre transient expression in embryonic stem cells: comparison of various promoters. J Biochem (Tokyo). 122, 977-82; Ludwig et al., 1996, FLP-mediated site-specific recombination in microinjected murine zygotes. Transgenic Res. 5, 385-395; Flp expression vector pOG44 from Invitrogen, #V6005-20), while integrated stably or episomally in cell lines (Seibler and Bode, 1997, Biochemistry 36, 1740-1747) in transgenic animals (Nelson et al., 1998, Expression of an AQP2 Cre recombinase transgene in kidney and male reproductive system of transgenic mice. Am J Physiol. 275, C216-226) or even tissue-specifically ("Transgene Tiere" [transgenic animals] by J. Schenkel, 1995, Spektrum-Verlag ISBN 3860252690). The recombinases as such are also available as purified proteins (e.g. Creator™ Kit from Clontech) and thus can optionally be transfected into the cell interior in this form.

DNA Sequences and Suitable Gene Loci

Also known are the DNA sequences of suitable genes, gene fragments (in particular vH, vlambda, vKkappa and the associated J segments) and gene loci of humans (http://genome.ucsc.edu/goldenPath/hgTracks.html; www.gdb.org; www.gdb.org/hugo; www.ncbi.nlm.nih.gov; www.ncbi.nlm.nih.gov/LocusLink) or the mouse (www.informatics.jax.org), in particular the active antibody gene loci and the diversity of the antibody genes (Immunoglobulin Facts Book, Lefranc and Lefranc, 2001, Academic Press, ISBN 0-12-441351-X; http://imgt.cines.fr; Kabat database: http://immuno.bme.nwe.edu) and the gene loci of the T cell receptor (T-Cell receptor Facts Book, Lefranc and Lefranc, 2001, Academic Press, ISBN 0-12-441352-8; http://imgt.cines.fr). The active antibody gene loci, in particular the mouse hybridoma cell line HEA125 which express genomically recombined antibody genes, are particularly preferred within the meaning of this invention.

However, it is also possible to use initially unknown gene loci, e.g. by selecting cells having the highest possible expression rate of an antibiotic resistance (FIG. 6). Vanin et al. (1997, Development of high-titer retroviral producer cell lines by using Cre-mediated recombination. J Virol 71, 7820-7826) describe a method suitable for this, which is very similar to the first step shown in FIG. 6 (integration instead of cassette exchange). Here, the resistance gene selected for high expression rate is flanked by specific recombination signals. A similar system is sold by Invitrogen (Flp-In™ pcDNA5/FRT Complete Kit #K6010-01; U.S. Pat. Nos. 4,654,182 and 5,677,177). This enables the comparatively simple exchange of the pre-selected resistance gene with a group of different antibody genes for example. It is preferred to introduce before that as an intermediate step additional other recombination signals which flank a variable, i.e. exchangeable, gene portion, in particular by recombining them into the pre-selected gene locus together with a constant gene portion (FIG. 6). In this case:

1. the integration of specific recombination signals into a first active gene locus is selected by the expression of a resistance gene (or the corresponding resistant cell line),
2. on account of the specific recombination signals a constant protein portion is recombined, in particular the differentially spliced CH2, CH3, M1 and M2 domains of a human IgG1 gene (optionally with CH1),
3. the genes for variable protein portions are recombined simultaneously, in particular a vH gene or an scFv gene of an antibody which is additionally flanked by 2 further specific recombination signals,
4. the desired recombination event is selected on account of the surface presentation of the expressed antibody,
5. analogous steps are then taken, where appropriate, for the genes of the light antibody chain, and
6. the diversity of different antibodies is recombined into said gene loci by specific recombination.

Production of Complex DNA Sequences

Another essential element of the present invention is the production of a large number of different DNA sequences, in particular of as many different antibody genes as possible. These DNA sequences which are flanked by the above mentioned recognition sites for recombinases serve as donors for many different DNA sequences which under the influence of recombinases are recombined with a comparatively great efficiency into said gene loci with the desired acceptors for DNA sequences. The techniques required for this, in particular PCR techniques (inter alia Sambrook and Russell: Molecular Cloning, a laboratory manual, $3^{rd}$ edition, 2001, ISBN 0-87969-577-3; in particular Chapter 8 for PCR techniques) and DNA sequences (see above) are also known to the person skilled in the art and described in a plurality of publications, above all for the production of libraries of recombinant antibodies (inter alia "Rekombinante Antikörper" [recombinant antibodies], Chapter 2.2 by Breitling and Dubel, 1997, Spektrum-Verlag, ISBN 3-8274-0029-5). In particular the book *Immunoglobulin Facts Book* (Lefranc and Lefranc, 2001, Academic Press, ISBN 0-12-441351-X) is an excellent source of the about 200 variable (and constant) human antibody sequences together with the accession numbers for the databases given therein. The multiplication of the plurality of genomically recombined human antibody genes can be made within the meaning of the present invention e.g. comparatively simply by a combination of only some (less than 50 in each case) vH, vkappa and vlambda specific PCR primers having (less than 6 in each case) $J_H$, $J_{kappa}$ and $J_{lambda}$ segment-specific counterprimers (FIG. 14), the primers preferably hybridizing to genomic regions which are hardly preserved evolutionarily. The same applies similarly to the murine antibody genes. The genomic DNA of a plurality of B lymphocytes particularly obtained from human blood serves as a template of the thus necessary less than 1,000 PCR reactions. The genomic DNA of these B lymphocytes contains very many differently genomically recombined antibody genes (vH, vkappa, vlambda) which as regards their plurality can be multiplied very easily by the described procedure. The plurality of genomically recombined T-cell receptors can also be transferred quite analogously into a group of suitable DNA sequences by a comparatively small number of PCR reactions.

In order to flank these numerous different DNA sequences having the above-mentioned recognition sites for recombinases, they can either be cloned into a given cloning vector which already contains these recognition sites or a downstream second PCR carries along these recognition sites with the PCR primers used. The group of different PCR products is then cloned preferably into a plasmid (e.g. pUC19 from Biolabs, pBluescript from Stratagene, pCR-TOPO, pCR-XL-TOPO, pCR-Vector, pZErO-1, pCR-Blunt, pSinRep5 from Invitrogen). Here, a replication origin under selection pressure can optionally result in a stable episomal replication (e.g. the hygromycin-selectable episomally replicating vectors pCEP4, pREP7, pREP10, pEBVHis or pREP4 from Invitrogen). As a result, the period within which a specific recombination with the above-mentioned gene loci may occur can be prolonged very easily. For this purpose, the presence of the corresponding recombinases or the corresponding expression vectors is, of course, necessary as well. In a particularly preferred embodiment, the expression cassettes for said recombinases are incorporated into the just mentioned cloning vector.

A group of different plasmids can also be generated in vitro, where appropriate, in an extremely high complexity ($>10^{12}$), it being avoided to multiply them in bacteria beforehand (complexities of about $10^9$ independent bacterial clones per µg DNA employed can currently be achieved as a matter of routine by electroporation; see e.g. Clontech #C2023-1 330, the *E. coli* strain KC8 $>10^9$ cfu/µg pUC). For this purpose, the described different PCR products which are flanked by the above-mentioned recognition sites for recombinases are preferably circularized initially by means of ligase (donors for DNA sequences) and mixed with a cloning vector which contains the same recognition sites (acceptors for DNA sequences). Under the influence of the purified recombinase proteins a highly complex mixture of cloning vectors having different recombined DNA sequences is here formed in vitro. This method is also known to the person skilled in the art and already commercially available (see inter alia Creator™ Kit from Clontech; Gateway™ from GibcoBRL/Invitrogen).

In addition, there are further methods with which the person skilled in the art is familiar. A plurality of different DNA sequences can be produced therewith (e.g. in vitro DNA shuffeling, Stemmer, 1994, Nature 370, 389-391 or the multiplication of the plurality of antibody cDNA or non-directed sheared genomic DNA). Here, in particular the production of very many different antibody genes by combinatory synthesis of DNA sequences, in particular different CDR-DNA sequences, should be mentioned (Breitling et al., 1990, "synthetic human antibody libraries", German patent No. P 40 02 897; see also Morphosys company, HuCal antibody library).

Cell Lines

The murine hybridoma cell line HEA125 preferred for the method according to the invention produces a murine IgG1 antibody together with a murine kappa chain. This monoclonal antibody recognizes the human tumor-associated antigen Ep-CAM with high-affinity and specificity (Moldenhauer et al., 1987, Br J Cancer 56, 714-722; Momburg et al., 1987, Cancer Research 47, 2883-2891). A subpopulation derived therefrom presents comparatively many membrane-bound antibodies on the surface. Other cell lines, in particular other hybridoma cells or lymphoid cell lines, such as the human lines:

U266 which produces a lambda chain and an IgE (Ikeyama et al., 1986, Purification and characterization of IgE produced by human myeloma cell line, U266. Mol Immunol 23, 159-167);

IM-9 (Lesniak and Roth, 1976, Regulation of receptor concentration by homologous hormone. Effect of human growth hormone on its receptor in IM-9 lymphocytes. J Biol Chem 251, 3720-3729); and the Jurkat T cell line (Gillis and Watson, 1980, Biochemical and biological characterization of lymphocyte regulatory molecules. V. Identification of an interleukin 2-producing human leukemia T cell line. J Exp Med 152, 1709-1719); or the chicken B cell line DT40 (Buerstedde and Takeda, 1991, Cell 67, 179-188)

are also suited for the method according to the invention. Human cell lines here have the additional advantage that as a result the somewhat different glycosylation of mouse cells is avoided (Borrebaeck, 1999, Nat Biotechnol 17, 621). T cell lines such as Jurkat should be preferred if a T cell receptor library shall be established or if the active T cell receptor gene locus shall be used. The chicken cell line DT40, however, has comparatively very high efficiencies of the homologous recombination of transfected DNA.

Transfection

The eukaryotic cells are also transfected by means of standard methods known to the person skilled in the art (Sambrook and Russell: Molecular Cloning, a laboratory manual, $3^{rd}$ edition, 2001, ISBN 0-87969-577-3; Chapter 16) such as electroporation (AGS company/Hybaid or BioRad, Handbuch der Elektroporatoren [manual of electroporators] BTX or BioRad GenePulser) or the transfection, e.g. with LipfectAMINE™ 2000 Reagent (Invitrogen #1668-027), with DMRIE-C Reagent (Invitrogen #10459-014), or LipofectAMINE™ Reagent (Invitrogen #18324-012), FuGENE 6 Transfection Reagent (Roche #1815091), DOTAP Liposomal Transfection Reagent (Roche #1811177), or DOSPER Liposomal Transfection Reagent (Roche #1811169). The portion of the successfully electroporated hybridomas is here usually from 20-30% of the employed cells. For transfections aiming at a homologous recombination of the transfected DNA sequences, said DNA sequences are preferably linearized. If a specific recombination of the transfected DNA sequences is desired, preferably circular DNA sequences are used, vectors replicating episomally in hybridoma cells are particularly suited for this (see above). The amount of a successful specific recombination by cassette exchange within a eukaryotic cells is about 1% of the successfully electroporated cells (Feng et al., 1999, Site-specific chromosomal integration in mammalian cells: highly efficient CRE recombinase-mediated cassette exchange. J Mol Biol. 292, 779-785), so that about $10^7$ different specific recombination events are obtained by the use of $3\times10^9$, cells.

Surface Expression/Enrichment Method

Another essential element of the present invention is the isolation or enrichment of the cells in which the desired recombination event has taken place (if possible after each processing step) (FIGS. 7, 8, 9). The invention enables this by proving modified proteins on the surface of the living cells producing them. This is also done according to conventional methods known to the person skilled in the art, such as the use of magnetobeads (Dynal company, Oslo, Norway; Technical Handbook: Cell Separation and Protein Purification from Dynal; Current Protocols in Immunology, John Wiley & Sons, New York, ISBN 9-471-52276-7 and company MiltenyiBiotec MACS—System (www.miltenyibiotec.com)) or a FACS sorter (Shapiro, H. M. Practical Flow Cytometry, $3^{rd}$ edition 1995, Wiley-Liss., N.Y., ISBN 0-471-30376-3; Darzynkiewics et al., Flow Cytometry, $2^{nd}$ edition 1994, Academic Press, ISBN 0-12-564142-7; Current Protocols in Immunology, John Wiley & Sons, New York, ISBN 0-471-52276-7) or by ELISA and repeated subcloning. The very rare (about 1 out of $10^7$ cells) homologous recombination events can be identified e.g. using a FACSVantage SE equipped to form a turbosorter or a FACSDiva (Becton-Dickinson) or a MoFlow (Cytomation), a pre-selection on account of a recombined resistance gene taking additionally place when specific recombination signals are introduced into defined gene loci (e.g. Geneticin (G418) from Sigma; Chauhan and Gottesman, 1992, Construction of a new universal vector for insertional mutagenesis by homologous recombination. Gene 120, 281). However, this type of pre-selection is not essential in the present invention and would be avoided in particular if the resistance gene integrated chromosomally for this purpose impeded the surface expression of the protein modified by homologous recombination. An example of such an impeded surface expression is the humanization described by Yarnold and Fell (1994, Cancer Research 54, 406-512) of hybridoma cells by homologous recombination. Here, the resistance gene integrates into the intron, essential for the differential splicing, between CH3 and M1.

The more frequent (about 1 out of $10^2$ to $10^3$ cells in a cassette exchange) specific recombination events can also be enriched by standard methods by proving modified proteins on the cell surface using a FACS sorter or magnetobeads (FIG. 9) as described in the below examples.

To this end, the modified proteins are stained preferably prior to sorting using a FACS by means of fluorescence-labeled monoclonal or polyclonal antibodies (or protein G or the like) which can be purchased from many companies (e.g. Jackson ImmunoResearch, West Grove, Pa., U.S.A., or Dianova, Germany or Southern Biotechnology Associates, Birmingham, Ala., U.S.A. or BIOZOL, Germany). Clear signals are here obtained in particular by double staining, two different fluorescences proving the proteins encoded by interchanged DNA sequences (or the lack thereof). The methods required for this are known to the person skilled in the art and described in a plurality of detailed publications (e.g. Scheffold and Kern, 2000, Recent developments in flow cytometry. J Clin Immunol. 20, 400-7. Review; Thiel A., Scheffold A., Radbruch, 1998, Immunomagnetic cell sortin-pushing the limits. Immunotechnology. 2, 89-96. Review; and the above indicated cytometry manuals). For example, the exchange of a kappa domain derived from a mouse with a human one (by homologous or specific recombination) can be proved by staining using FITC-labeled goat anti-human kappa antibodies and sorted, counterstaining simultaneously taking place by means of PE-labeled goat anti-mouse kappa antibodies. However, the lack of a signal can also be proved, if e.g. by homologous recombination the vH domain of an IgG antibody presented on the surface of a hybridoma was exchanged with a G418 resistance gene. Following pre-selection using G418, the staining with FITC-labeled goat anti-IgG antibody yields another enrichment of homologous recombination events by means of FACS: In this case, the cells having green fluorescence have not acquired their G418 resistance by homologous recombination and are thus depleted in FACS. The use of epitope-specific monoclonal antibodies, such as a Mycl-9E10 epitope-specific antibody (Evan et al., 1985, Mol. Cell. Biol. 5, 3610-3616) is also helpful. The latter serves for identifying modified vH domains, for example. The exchanged DNA sequences can also be identified directly in FACS, without further staining, if e.g. the gene for an EGFP is recombined and expressed (enhanced green fluorescent protein; Clontech).

Figure 2:
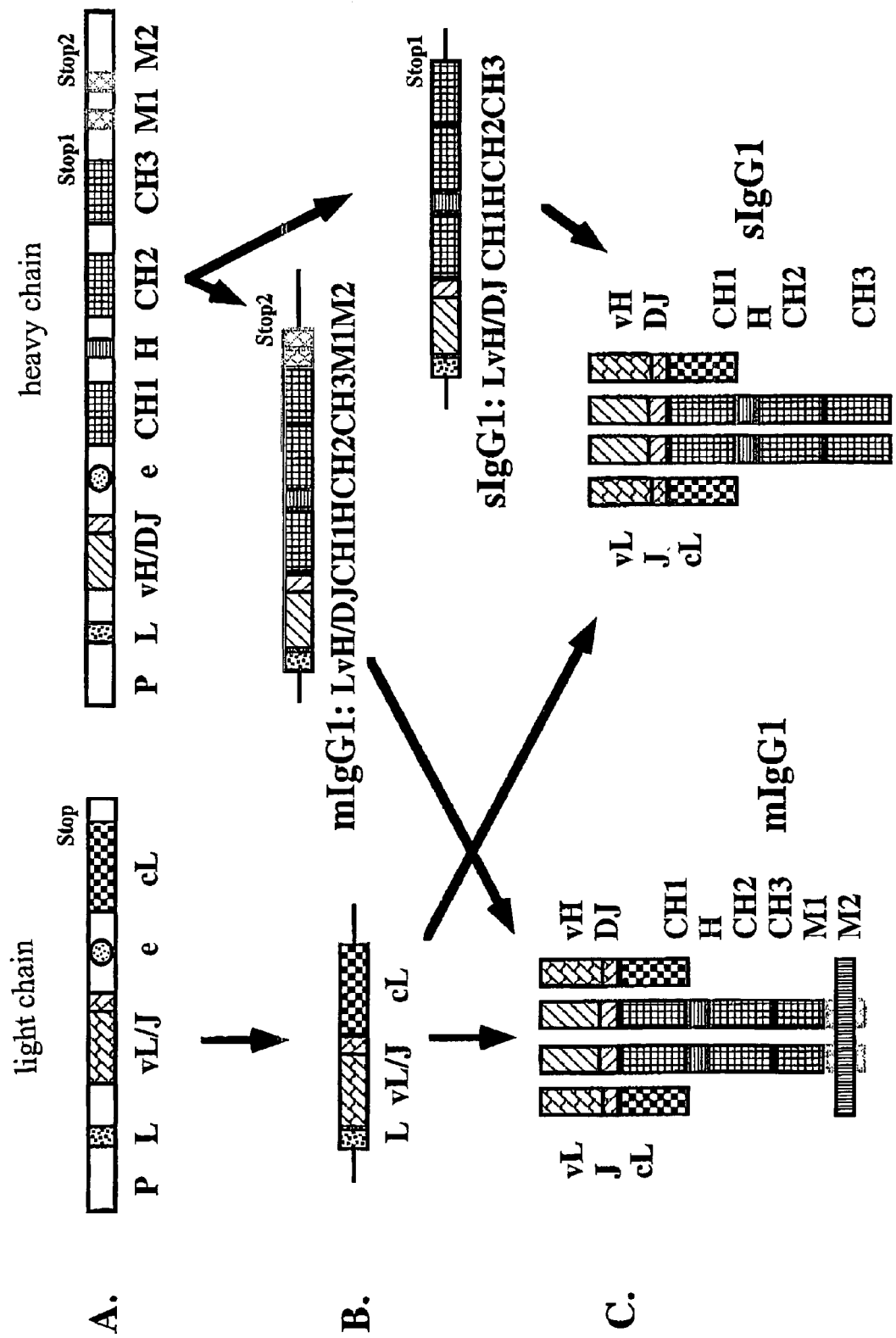

The surface presentation, in particular of antibodies, is achieved in the present invention preferably by the differential splicing of the mRNA for the heavy antibody chain (or corresponding chimeric mRNAs) (FIG. 2; *Immunologie* [immunology] by Janeway and Travers, Chapter 3-24, $4^{th}$ edition 1999, Spektrum-Verlag, ISBN 443062757). This offers the advantage that in addition to a variant bonded covalently to the membrane, major amounts of the form secreted into the culture medium are also available for a rapid and ready characterization of a cell clone or a cell library. The membrane-bound antibody portion and thus the expected signal strength can be increased by shortening the intron between the CH3 domain and M1 domain of an IgG or IgA (or between the CH4 domain and M1 domain of an IgM), in particular by 300 bp to 1,000 bp (Peterson and Perry, 1986, PNAS 83, 8883-8887; Tsurushita and Korn, 1987, Molec. Cell. Biol. 7, 2602-2605); Galli et al., 1987, Genes Dev 1, 471-481; Seipelt and Peterson, 1995, Molecular Immunology 32, 277-285; FIG. 3, III.). Alternatively, other membrane anchors, such as of the alpha T cell receptor (EMBL accession number X02883, the sequences of exon 3) or of an MHC molecule can be used for this purpose, so that even more proteins can be presented on the surface. A non-covalent coupling of antibodies on the cell surface by membrane-bound protein G is also possible (Breitling et al., 1999, PCT DE00/00079), this comprising the drawback of cross-talks: Here, not all of the antibodies have to be encoded by the cell presenting them.

The surface presentation is of great use in particular if many ($>10^2$) cells differing from one another because of the expressed proteins can be screened for a certain protein activity. The present invention achieves this quite analogously to the technology of recombinant antibodies where this is achieved in particular by presenting the antibodies on a phage (Breitling et al., 1991, Gene 104, 147-153) or on a bacterium (Fuchs et al., 1991, Bio/Technology 9, 1369-1372). As described therein, it is thus possible to screen much more complex protein libraries. The present invention has the additional advantage that it reaches a comparatively very high signal intensity by the large number of presented, always similar proteins, in particular antibodies. Today's FACS sorters reach sorting rates of about $10^8$ cells per hour (e.g. FACS-Vantage SE, see above), an even more complex protein library being additionally enrichable by magnetobeads beforehand. The technique of FACS sorting required for this invention is described by Kern et al. (1998, Nature Medicine 4, 975-978) and Maecker et al. (2001, J Immunol Methods 255, 27-40) who were able to identify epitope-specific T cells by this.

Hybridoma Antibody Library

In a preferred embodiment of the method according to the invention, each transfection step using a group of different DNA sequences and subsequent specific recombination (FIGS. 5, 6) is followed by an enrichment of cells producing surface-bound antibodies having the highest possible antibody diversity (FIG. 9). This can be done as described above, i.e. the group of hybridoma cells is stained with 2 different staining reagents as described above and then as many cells as possible are sorted in the FACS sorter. In this connection, the cells which show a staining pattern typical of the starting cell are depleted.

This is done e.g. by the detection of a myc epitope in the vH domain of the starting cell. Alternatively, it can be utilized, for example, that prior to the specific recombination the starting cell does not present antibodies on the surface but that a G418 resistance is incorporated in the gene locus of the monospecific cell line. However, the cells which present an, in particular human, IgG chain or kappa or lambda chain are enriched. These are the cells which have conducted a productive specific recombination.

The result of this procedure is a complex (>$10^6$ different hybridoma specificities) hybridoma library (FIGS. 5, 6, 9) whose individual members present large quantities of a human antibody on the surface (about $10^4$ to $10^6$ antibody molecules per cell). The number of the presented antibodies per cell is within a comparably narrow range, since all the cells are derived from the same parental hybridoma. The subject matter of the present invention is thus also an antibody library which can be obtained with the method according to the invention. It comprises preferably a group of at least 100 different cells, more preferably a group of at least 1000 cells.

The described procedure for the production of a hybridoma antibody library is also described in FIGS. 3, 5 and 9:

The above described group, as complex as possible, of vL gene plasmids is electroporated into as many cells as possible (about $3 \times 10^9$ cells) of a monospecific cell line. At the same time, an Flp expression vector, for example, is electroporated into the cells;

the portion of the successfully electroporated hybridomas is here usually 30 to 40% of the surviving cells. Thus, a group of hybridoma cells are formed which present different vL domains on the surface at a frequency of about 1 out of 300 so that a hybridoma library of a complexity of about $10^7$ different hybridomas (total amount $3 \times 10^9$ cells), i.e. different antibodies, is formed;

this group of hybridoma cells is optionally expanded and then stained with two different staining reagents as described;

thereafter as may cells as possible are sorted in the FACS sorter or with magnetobeads. The cells of the monospecific cell line and unproductively recombined cells are depleted and the cells which present a human kappa or lambda chain are enriched;

the above described group of vH gene plasmids which is as complex as possible, is electroporated into the greatest possible number of cells of the just described group of hybridoma cells. A Cre expression vector is simultaneously electroporated into the cells;

as a result, a group of hybridoma cells is formed which presents different vH domains on the surface at a frequency of about 1 out of 300;

this group of hybridoma cells is again stained with 2 different staining reagents as described; and thereafter, as many cells as possible are sorted in the FACS sorter or with magnetobeads. The cells of the cell line monospecific for the vH gene locus and unproductively recombined cells are depleted and the cells presenting a human IgG chain are enriched (FIG. 9).

A special embodiment of the method according to the invention is characterized in that the eukaryotic cells are mammalian cells, preferably neoplastic lymphocytes or precursors thereof, leukemia cells or malignant lymphoma cells or hybridoma cells.

In another preferred embodiment of the method according to the invention for the production of an antibody library, the vH genes, vlambda genes and/or vkappa genes are human genes. A method where the gene loci are antibody loci and contain the active vH gene, vlambda gene or vkappa gene is particularly preferred.

The method according to the invention also comprises a method of producing a library of T cell receptor-producing cells, the different DNA sequences containing different T-alpha receptor genes or T-beta receptor genes, as well as a method of producing a library of exon-expressing cells, the different DNA sequences containing different genomic exons coding for splice signals. Here, an embodiment where the gene loci are the T cell receptor loci and contain the active T-alpha receptor gene or the active T-beta receptor gene are particularly preferred.

In another preferred embodiment of the method according to the invention for the production of an antibody library, the antibodies are monoclonal human antibodies bonded covalently on the surface of the cell expressing them. Here, an embodiment where the monoclonal human antibodies expressed by the particular cell are bonded covalently by the differential splicing of the constant domains of an IgG, IgM, IgA, IgD or IgE on the surface of the cell expressing them is particularly preferred.

In the method according to the invention more than $10^2$ different cells, each expressing different proteins, are preferably obtained per expanded individual cell.

In another preferred embodiment of the method according to the invention for the production of a library of eukaryotic cells producing antibodies, the homologous regions of the transfected DNA extend to the particular gene loci of the cell which flank the specific recombination signals over at least 400 base pairs.

In an even more preferred embodiment of the method according to the invention for the production of a library of eukaryotic cells producing antibodies, the intron is shortened in the 5' end direction before the M1 exon of an IgG, IgM, IgA, IgD or IgE gene by more than 50 base pairs.

In another preferred embodiment of the method according to the invention, the cells which on the cell surface present the proteins bound on the surface of the cells expressing them are enriched after the transfection with a plurality of different DNA sequences from the resulting plurality of different cells so as to form a cell population having the greatest possible protein diversity.

An embodiment of the method according to the invention is particularly preferred in which in the transfection steps with the plurality of different DNA sequences in the gene loci each flanked by the recognition sites for a recombinase DNA, sequences having expressible DNA sequences coding for the corresponding recombinase are transfected and/or activated.

The above invention also relates to a library of protein-producing, preferably antibody-producing, eukaryotic cells which can be obtained according to the method of the invention.

Selection of Antibodies

The present invention also relates to a method of isolating a monoclonal antibody with a desired specificity (see FIG. 9), the method being characterized by incubating an antibody library produced according to the method of the invention with the corresponding antigen and subsequently isolating or enriching the cell line on the surface of which the antigen is bound.

The person skilled in the art knows methods as to the contacting of the antigen with an antibody library and as regards the selection of the desired antibody (Liddell and Weeks, 1996, "Monoclonal Antibodies: Principles and Practice." Spektrum-Verlag ISBN 3827400481; Goding, J. W., 1996, "Production and Application of Monoclonal Antibodies in Cell Biology, Biochemistry and Immunology. Third Edition. Published by Academic Press Limited, 24-28 Oval Road, London NW1 7DX; ISBN 0-12-287023-9). These methods have also been described in detail for the selection of surface-presented recombinant antibodies from phage libraries (inter alia de Kruif et al., 1995, PNAS 92, 3938-3942) and from bacterial libraries (Fuchs et al., 1996, J. of Immunotechnology. 2, 97-102). In the present invention, these methods are adapted in particular to the screening of eukaryotic cell populations by means of magnetobeads or a FACS sorter. These methods are also known to the person skilled in the art: They are identical with staining living cells for a FACS (Fluorescence Activated Cell Sorter) and described in detail in a plurality of special laboratory manuals (see above).

Preferably the cells, produced according to the method of the invention, of the antibody library are stained with biotinylated and thereafter with streptavidine-FITC-labeled antigen (or directly FITC-labeled antigen) and the most intensive staining results are selected. If desired, the antibody library can also be stained with a mixture of optionally differently labeled antigens and the most intensive staining results are selected again. Thereafter, the individual cells are expanded in a cell culture, each producing the desired, in particular human, monoclonal antibody only a single selection run is usually required for the antigen-specific selection, since the very large number of presented antibodies yields very clear signals. In particular, there is the possibility of using the antibodies, secreted on account of a splice variant into the culture supernatant, of a hybridoma antibody library, of a sub-library obtained therefrom or of individual clones for the characterization of an activity searched for. In the antibody library according to the invention, antibody specificities against human antigens should also be represented on account of the new combination of the vH and vL domains.

Selection of More Affine Antibodies

In a particularly preferred embodiment, the method according to the invention is further characterized by producing highly affine antibodies. Here, the person skilled in the art can proceed according to the below methods.

Figure 10:
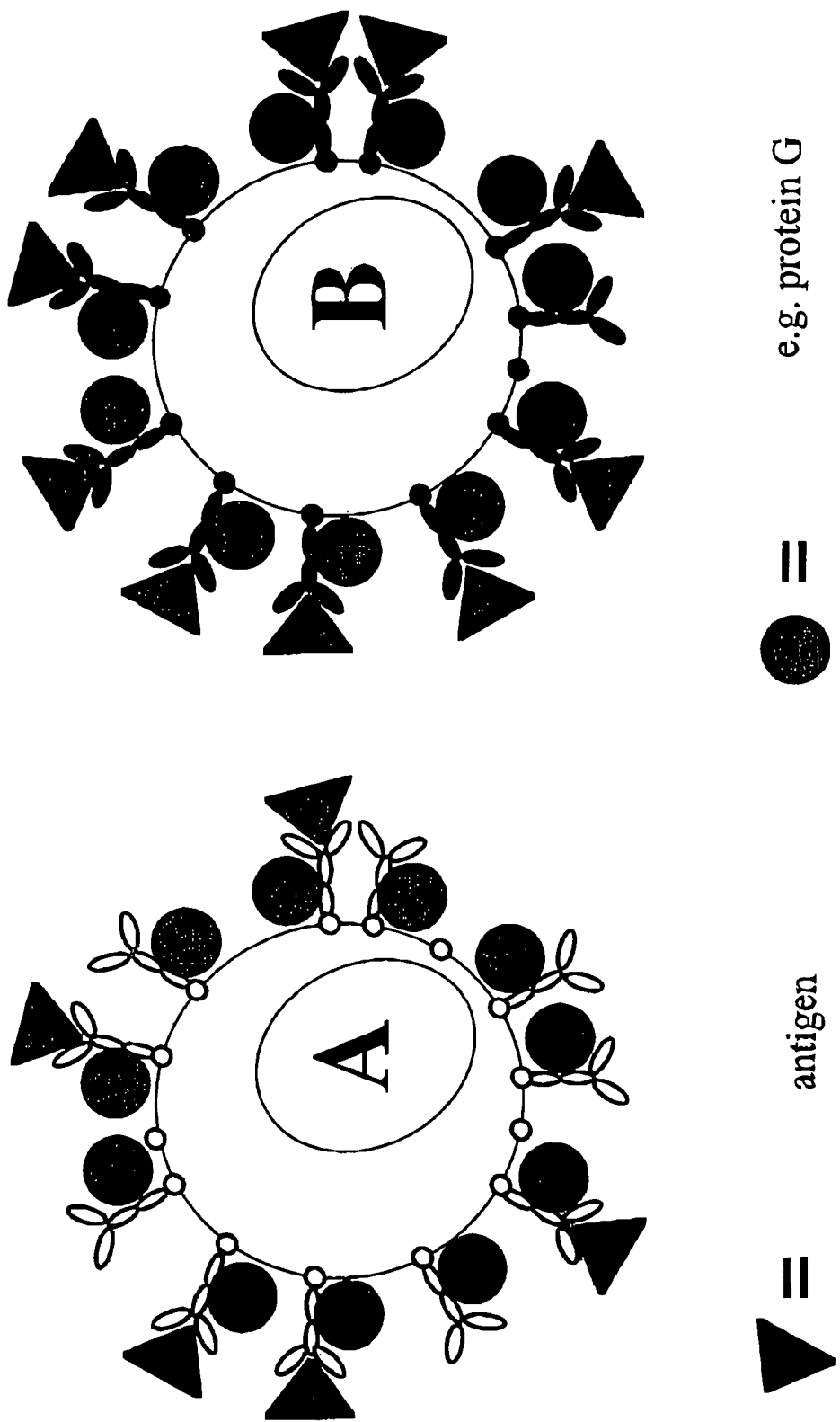

For example, more affine monoclonal antibodies can be selected by FACS. For this purpose, the antibody library or a group of different antigen-specific hybridoma cells derived therefrom are stained with PE-labeled antigen as described above. These cells are counterstained using FITC-labeled protein G. Thereafter, the staining results having the greatest quotient PE staining: FITC staining are selected in the FACS sorter. The individual cells are expanded in a cell culture, each producing a human monoclonal antibody having a comparatively high affinity for the antigen used for the selection. This is a very simple method to discover highly affine monoclonal antibodies. Here, an easily conductible normalization of the number of presented antibodies enables an "on line" affinity comparison of the discovered antibody specificities, since the ratio of antibody-bound antigens to antibody-non-bound antigens is a direct measure of the antibody affinity to its antigen (FIG. 10).

Figure 11:
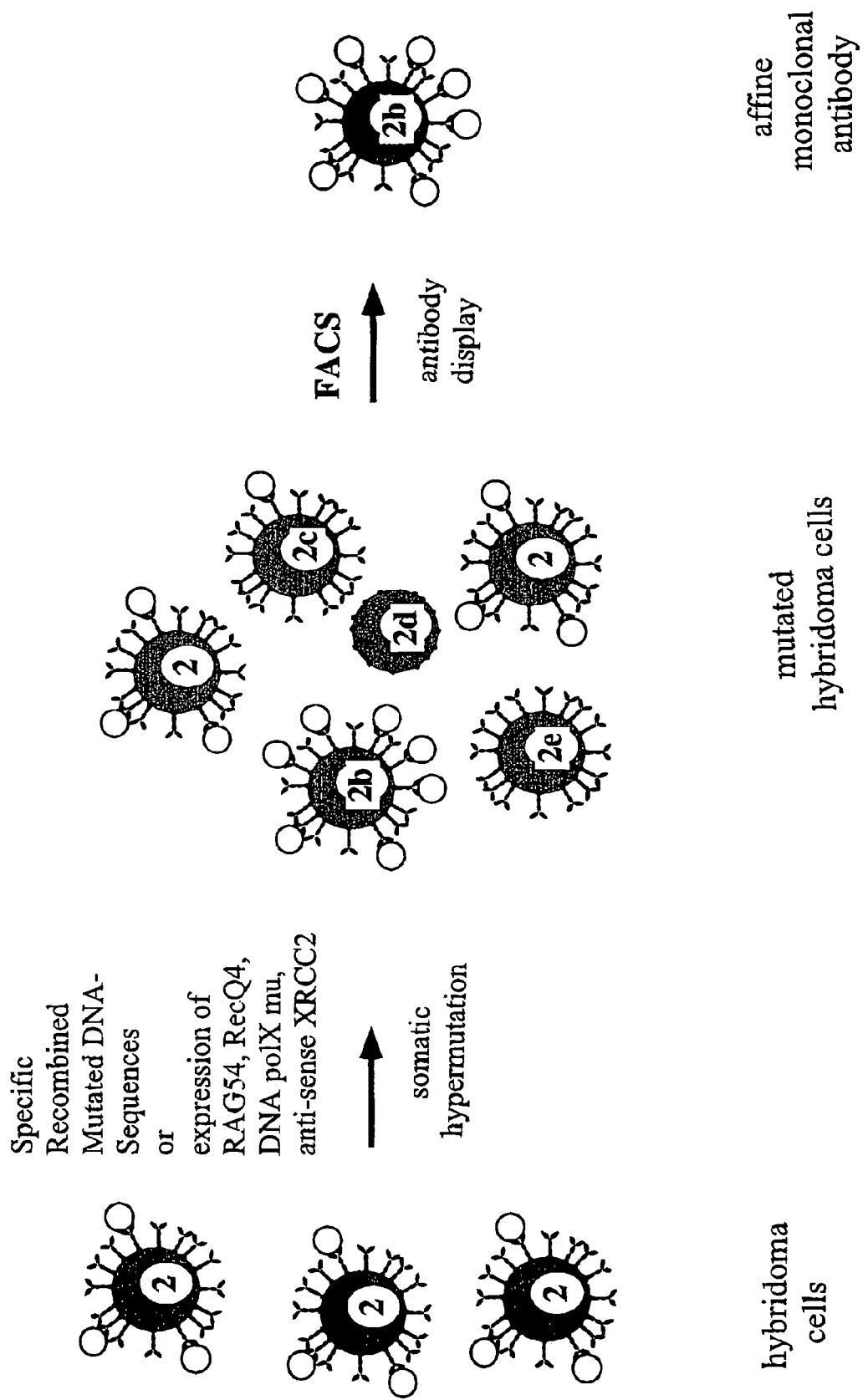

In a preferred embodiment, the above method is characterized in that the introduction of mutations within the variable antibody genes precedes the isolation of highly affine antibodies. This can be done e.g. by carrying out a somatic hypermutation or a gene conversion of the antibody genes, which as described is followed by the selection of modified, in particular more affine, antibodies presented on the cell surface (FIG. 11).

For Example, "chain shuffling" and subsequent selection of highly affine monoclonal antibodies can be carried out. Here, e.g. a FITC-labeled antigen is used to initially select, as described, from the established antibody library a group of antigen-specific hybridoma cells, derived therefrom. This group of selected hybridoma cells is expanded in a cell culture. Thereafter, one of the variable domains is exchanged in a specific recombination event with a group of different DNA sequences, in particular other variable domains, as described above (gene conversion). The resulting group of hybridoma cells is expanded in a cell culture. Thereafter, comparatively (FIG. 10) highly affine, monoclonal human antibodies are selected therefrom by means of a FACS sorter, as described above. This is a very simple method to produce a group of hybridomas from which highly affine monoclonal antibodies can be isolated.

Alternatively, a plurality of non-directed mutations can be inserted in a template DNA, in particular in pre-selected variable domains, by an error-prone PCR (Stemmer, 1994, Nature 370, 389-391). Thereafter, the greatest possible number of these mutated variable antibody genes are recombined into the antibody locus by means of specific recombination signals, as described, and then the cells which present an antibody having relatively high affinity on the surface, are selected in FACS, for example. Here, the non-directed mutations can also be combined according to the method developed by Stemmer (gene conversion/somatic hypermutation).

Another inventive method of producing non-directed mutations is by means of eukaryotic expression vectors expressing the genes RAD54, RecQ4 and/or the gene DNA PolX mu in lymphoid cells, in particular in combination with anti-sense RNA against XRCC2, XRCC3 or RAD51B (Kitao et al., 1998, Cloning of two new human helicase genes of the RecQ family: biological significance of multiple species in higher eukaryotes. Genomics 54, 443-452; Aoufouchi et al., 2000, Two novel human and mouse DNA polymerases of the polX family, Nucleic Acids Res 28, 3684-3693; Sale et al., 2001 Ablation of XRCC2/3 transforms immunoglobulin v gene conversion into somatic hypermutation, 2001, Nature 412, 921-96; expression vectors e.g. pCEP4, pREP7, pREP10, pEBVHis or pREP4 from Invitrogen). The gene products RAD54, RecQ4 and DNA PolX mu are part of the mutator complex responsible for the introduction of somatic hypermutations into the active antibody genes while the suppression of the expression of XRCC2, XRCC3 or RAD51B obviously initiates the somatic hypermutations by increased single-strand breakage. Here, in particular in the process of forming memory cells of the organism about 1.5 kb DNA sequences are mutated downstream of the active vH, vkappa or vlambda promoter in non-directed fashion, irrespective of the DNA sequences available there. In order to produce a somatic hypermutation, for example, the following steps can be taken: From the antibody library according to the invention a group of antigen-specific hybridoma cells derived therefrom are selected with FITC-labeled antigen as described above. This group of selected hybridoma cells is expanded in a cell culture and then a mixture of the above described expression vectors is electroporated into these cells. The resulting group of hybridoma cells is expanded in a cell culture. Thereafter, highly affine monoclonal human antibodies are selected therefrom by means of a FACS sorter, as described above.

Particularly preferred is an embodiment of the above method where the cell is transfected with a plurality of DNA sequences each being flanked by specific recombination signals, the plurality of DNA sequences having been obtained by means or error-prone PCR.

Humanization of Already Existing Hybridomas

The present invention also relates to methods of humanizing already existing mouse hybridomas by means of homologous recombination (FIGS. 3, 7). Here, any chosable murine IgG1 hybridoma cell can be converted into a human IgG1 hybridoma cell e.g. by means of a given, always equal DNA vector (FIGS. 3, 7) or with other DNA vectors into human IgG2, IgG3, IgG4, IgA1, IgA2, IgE or IgM. Again other DNA vectors enable the reconstruction of a murine IgM hybridoma, etc. This particularly easy and advantageous method makes do without the use of an interfering resistance marker (see also Baker et al., 1994, J. Immunological Methods 168, 25-32), since the modification resulting from the surface presentation of the modified gene product is used for selecting the modified cell (FIG. 7). This method is now enabled by providing very fast FACS sorters (e.g. FACSVantage SE, Becton-Dickinson) which can meanwhile sort about $10^8$ cells per hour, so that the very rare homologous recombination events can also be found. Otherwise, standard techniques known to the person skilled in the art are used for this purpose.

Thus, the present invention also relates to a method of humanizing a hybridoma cell, which is characterized by
(a) transfecting a DNA sequence coding for one or more human constant IgG, IgM, IgA, IgD or IgE domains into the hybridoma cell line;
(b) flanking the DNA sequence of the human constant IgG, IgM, IgA, IgD or IgE domains by DNA sequences homologous to the chromosomal gene regions flanking the constant domains of the active gene locus, coding for the heavy chain of the antibody, of said hybridoma cell;
(c) expanding one or only some cells which on account of a homologous recombination express an IgG-, IgM-, IgA-, IgD- or IgE-heavy chain with a humanized constant portion,
(d) transfecting a DNA sequence coding for a human constant kappa or lambda domain into the hybridoma cell line, this DNA sequence being flanked by DNA sequences homologous to the chromosomal gene regions flanking the constant kappa or lambda domain of the active kappa or lambda gene locus of the hybridoma cell;
(e) subsequently expanding one or few cells which on account of a homologous recombination express a kappa or lambda chain with a humanized constant portion,
on account of the covalent coupling of the membrane-bound splicing variant of the heavy antibody chain the expressed antibodies being bound to the surface of the cells expressing them, which permits the detection and selection of the cells presenting the humanized constant antibody domains.

In a preferred embodiment of this method, first the constant domains of the light antibody chain and then the constant domains of the heavy antibody chain are humanized, the procedure according to which only the constant domains of the heavy antibody chain or only the constant domains of the light antibody chain are humanized being preferred.

In another preferred embodiment of the above method, the intron is shortened in the 5' end direction before the M1 exon of the active IgG, IgM, IgA, IgD or IgE gene by more than 50 base pairs.

In another preferred embodiment of the above method additional protein-coding DNA sequences are fused to the humanized constant domains, preferably the additional protein-coding DNA sequences code for a linker sequence and a single chain antibody which is fused in C-terminal fashion to the constant domain of the light antibody chain.

In another preferred embodiment of the above method, the homologous regions of the transfected DNA sequences extend to the particular antibody gene loci of the hybridoma cell over at least 400 base pairs.

In another preferred embodiment of the above method, the homologous recombinations do not introduce any resistance markers into the cells which are used for selecting homologous recombination events.

The present invention also relates to a vector which contains one or more of the above described DNA sequences and host cells containing this vector. As to preferred vectors and host cells reference is made to the above explanations (see chapters "production of complex DNA sequences" and "cell lines").

The invention is explained by the below examples.

Example 1

Humanization of a Hybridoma Antibody

The hybridoma cell line HEA125 serves as an example of a monoclonal antibody to be humanized. This murine hybridoma cell line produces a murine IgG1 antibody together with a murine kappa chain. This monoclonal antibody recognizes the human tumor-associated antigen Ep-CAM with a comparatively high affinity and specificity (Moldenhauer et al., 1987, Br J Cancer 56, 714-722).

a. Culture Conditions

The cell line HEA125 was cultured and expanded. RPMI 1640 (Gibco BRL #31870-025) with an addition of 10% FCS, 1 mM pyruvate and 2 mM glutamine was used as the culture medium. The other culture conditions (plastic vessels from Falcon 25 cm$^3$; 37° C. hot cabinet; 5-7.5% $CO_2$ gassing, maximum of $10^6$ cells per ml, etc.) are known to the person skilled in the art.

b. Selection of a Subpopulation of HEA125

The expanded cells were initially washed twice with ice-cold Dulbecco's PBS (DPBS) and about $10^7$ cells per 400 µl were stained with FITC-labeled goat anti-mouse IgG antibody (Dianova). Propidium iodide (1 µg/ml) was used as a counterstain to identify dead cells. Another wash step with ice-cold DPBS was followed by sorting by means of a FACS sorter (FACSVantage SE, Becton-Dickinson) the 5% of cell population which had the strongest green fluorescence. A sub-population of HEA125 cells, which had comparatively many membrane-bound antibodies, was discovered and expanded under the above indicated culture conditions.

c. Chimeric Murine-Human DNA Sequences

Several individual gene fragments were combined in the cloning vector PBSIISK+ (Stratagene) into chimeric murine-human DNA sequences. Here, the individual gene fragments were produced by means of PCR (Roche Diagnostics; Expand Long Template PCR System; see also for the PCR conditions). Genomic DNA of the murine hybridoma cell line HEA125 served as a template for the genomic murine gene sequences and genomic DNA of human blood cells served as a template for the genomic human gene sequences. The isolation of genomic DNA and the required cloning techniques are described in various laboratory manuals (see e.g. Sambrook and Russell: Molecular Cloning, a laboratory manual, 3$^{rd}$ edition, 2001, ISBN 0-87969-577-3). FIG. 12 shows the resulting chimeric DNA sequences. The employed primers for the cloning in pBSIISK+ are described in FIG. 12. FIG. 12A illustrates the chimeric DNA sequences of the pBS MhKappaM vector which was used for humanizing the constant kappa chain of HEA125. FIG. 12B shows the chimeric DNA sequence of the pBS MhIgG1M vector which is used for humanizing the constant IgG1 CH1, CH2 and CH3 domains of HEA125.

d. Optimum Electroporation Conditions for HEA125

The optimum electroporation conditions for the transfection of HEA125 with DNA were tested as follows:

The cells were cultured in RPMI medium+10% FCS+1 mM pyruvate+2 mM glutamine;
then washed twice in ice-cold DPBS;
taken up in about $10^7$ cells per 400 µl DPBS buffer with 0.5 mM $Mg^{2+}$+0.1 mM $Ca^{2+}$;
added to 400 µl cells per 10 µg supercoiled plasmid DNA PEGFP N3 MCS (Clontech);
mixed in an electroporation cuvette having a width of 4 mm;
the cuvette was incubated with the cells on ice for 10 minutes;
followed by 1 current pulse of 2 ms duration each at 500 V-450 V using the BTX electroporator (AGS);
$10^7$ cells each were cultured in 10 ml RPMI+10% FCS+ 20% conditioned medium in 50 $cm^3$ bottles;
after 2 days washed twice in ice-cold DPBS with 2% FCS; and
the green fluorescence caused by EGFP was measured in a FACS.

As a result, 30-40% of the transfected hybridoma cells investigated in the FACS had a comparatively marked green fluorescence (control: electroporation using irrelevant vector DNA).

e. Humanization of the C-Kappa Domain of HEA125

The chimeric murine kappa constant domain humanization vector pBS MhKappaM described in Example 1c and FIG. 12A is linearized using the restriction enzyme BglI and in each case 10 µg linearized plasmid DNA is mixed with the expanded HEA125 cell subpopulation described in Example 1b. These cells are transfected under the optimized electroporation conditions described in Example 1d. After 2-4 days in a culture (described in Example 1a), the cells are washed twice with ice-cold DPBS and about $10^8$ cells per 4 ml are stained with FITC-labeled goat anti-mouse kappa antibody and simultaneously with PE-conjugated goat anti-human kappa antibody (Southern Biotechnology Associates). Propidium iodide is used as a counterstain to identify dead cells. Another wash step using ice-cold DBPS is followed by sorting the cells by means of a FACS sorter, about $10^8$ cells being sorted in 2 hours.

As a result, 2-5 individual cells per $10^8$ HEA125 cells may be sorted which may have a marked phycoerythrin(PE)-specific red fluorescence. The individual cells are expanded under the culture conditions described in Example 1a for 2-3 weeks. The resulting clones are then stained, as described, using FITC-labeled goat anti-mouse kappa antibody and simultaneously using PE-conjugated goat anti-human kappa antibody and analyzed in a FACS. Two clones having a marked red fluorescence signal are further propagated. The genomic constant kappa domain of these clones is multiplied by means of PCR and the primers HK3 and HK4 (primers see FIG. 12A) and sequenced. As a result, the clone HEA125-hkappa having a genomically coded constant human kappa domain is further propagated. The sequence of the transition from genomic murine kappa DNA to genomic human kappa DNA of this clone is shown in FIG. 12A.

Alternatively, cells in 96-well plates are sorted into pools of up to $1\times10^4$ cells, allowed to grow up to $2\times10^5$ cells and screened in ELISA for positive pools containing humanized AK-expressing cells. The PDX-coupled goat anti-human kappa AK serves as an evidence. Positive pools are subcloned and the method is repeated until the individual clones HEA125-hkappa are identified.

f. Humanization of the Constant IgG1 CH1, CH2 and CH3 Domains

The chimeric murine IgG1 humanization vector pBS MhIgG1M described in Example 1c and FIG. 12B is linearized using the restriction enzyme SspI and 10 µg linearized plasmid DNA each are mixed with cells of the partially humanized subclone HEA125-hkappa described in Example 1e. Cell culture, FACS and staining of the cells are identical as described in Example 1e, the difference being that in place of the PE-conjugated goat anti-human kappa antibody a PE-conjugated goat anti-human IgG antibody is used. As a result, initially 1-3 individual cells per $10^8$ HEA125-hkappa cells may be sorted which may have a markedly increased phycoerythrin(PE)-specific red fluorescence. After the control sequencing of the homologously recombined regions by means of the PCR primers HG3 and HG4 (see FIG. 12B) the cell line HEA125-hIgG1hKappa is further propagated which in addition to a constant human kappa domain genomically encodes the constant IgG1 CH1, CH2 and CH3. The sequence of the transition from genomic murine IgG1-DNA to genomic human IgG1-DNA of this clone is shown in FIG. 12B.

Thus, the constant domains with respect to human IgG1 of an IgG1-producing murine hybridoma cell, which can in principle be chosen as desired, are humanized. Murine hybridoma cells which produce IgG2a, IgG2b, IgG3, IgA, IgE or IgM can be humanized with other chimeric DNA sequences quite analogously. Depending on the humanization vector used, the individual antibody classes can also be converted or modified so as to convert e.g. a murine IgM into human IgG1, IgG2, IgG3, IgG4, IgA1, IgA2 or IgE. The same applies to the conversion of a constant murine kappa domain into a constant human lambda domain.

Example 2

Obtaining an Enhanced Antibody Surface Expression

In place of the chimeric murine IgG1 humanization vector pBS MhIgG1M described in Example 1f, the vector pBS MhIgG1Mdelta350 is used which has the deletion described in FIG. 12B of about 350 bp in the intron between the CH3 and M1 domains and, as for the rest, is identical with the vector pBS MhIgG1M described in Example 1f and FIG. 12B. The procedure is the same as described in Example 1f. Here, too, about 1-2 out of about $10^8$ cells may be found to have a homologous recombination in the region of the antibody gene locus of the heavy chain.

As a result of this example the cell line HEA125-mhIgG1hKappa is propagated which in comparison with the cell line HEA125-hIgG1hKappa described in Example 1f has markedly more membrane-bound humanized antibodies on account of the shortened intron between the CH3 domain and the M1 domain (see also FIG. 7, hybridoma cell 2H).

Example 3

Introduction of Specific Recombination Signals into the vH Gene Locus of HEA125 a. Chimeric DNA Sequences

Several individual gene fragments are combined in the cloning vector PBSIISK+ into chimeric DNA sequences. Here, the individual gene fragments are produced by means of PCR (Roche Diagnostics; Expand Long Template PCR System; see also for the PCR conditions). The PCR primers for this are shown in FIG. 13B. Genomic DNA of the murine hybridoma cell line HEA125 serves as a template for the genomic murine gene sequences. The vector ploxPfrtPGK-neofrtloxP serves as a template for the resistance gene PGK-neo (Erich Greiner, dkfz, Department: Molecular Cell Biology I). FIG. 13B shows the resulting vector pBS MvHG418M whose sequence is subsequently checked.

b. G418 Pre-Selection

The HEA125-hIgG1hKappa cell line obtained as described in Example 2 is transfected with the linearized pBS MvHG418M vector described in FIG. 13B, the electroporation conditions described in Example 1b being employed. Two days after the electroporation the DNA-transfected cells are initially subjected to a pre-selection using G418 (depending on the charge 200-800 μg G418 per ml for 14 days; as for the rest cell culture conditions as in Example 1). The expanded G418-resistant cells are then stained with FITC-labeled goat anti-human IgG antibody as described in Example 1b and sorted in a FACS. Here, about 2,000 individual cells may be sorted, as described above, which had have no antibody-specific staining (i.e. the least possible green fluorescence). These individual cells are expanded under the culture conditions described in Example 1a for 2-3 weeks.

c. Selection of Clones Having loxP Sites in the vH Gene Locus

The genomic DNA is isolated from the clones obtained as described in Example 3b, which serves as a template for a PCR (Roche Diagnostics; Expand Long Template PCR System; see also for the PCR conditions). The PCR primers vHG418-3 and vHG418-4 for this are described in FIG. 13B. The particular PCR bands are separated in an 0.8% TAE agarose gel according to their size and compared with the expected result. 8 of the 2,000 investigated clones may have a PCR band of the expected size of about 1.85 kb. After the control sequencing of the genomic DNA (or the described PCR band), the clone HEA125-mhIgG1hKappa-loxPG418 with genomically coded specific recombination signals (loxP and loxP511) is further propagated in the region of the active vH gene locus.

d. Specific Recombination

Cells of the about 2,000 clones described in Example 3b are pooled and, alternatively, the expanded clone HEA125-mhIgG1hKappa-loxPG418 described in Example 3c is used. The pBS loxPvHmyc vector shown in FIG. 15B is eletroporated into these cells. This vector encodes the genomically recombined vH gene of HEA125, which is flanked by loxP and loxP511 sites. In addition to the vH gene of HEA125 myc-tag is inserted in the CDR3 region of the vH domain. At the same time, the Cre expression vector pMC-Cre is electroporated into the cells (condition for this see Example 1d). After 2-4 days in a culture (described in Example 1a), the cells are washed twice with ice-cold DPBS and about $10^8$ cells per ml are stained with FITC-conjugated goat anti-human IgG antibody (Dianova). Alternatively, staining is carried out with FITC-labeled 1-9E10 anti-myc antibody. Propidium iodide is used as a counterstain to identify dead cells. Following another wash step with ice-cold DPBS, individual cells having a strong FITC fluorescence are sorted by means of a FACS sorter.

Alternatively, $2 \times 10^4$ cells/well are sorted in 96-well plates after 2-4 days in a culture, and the reoccurrence of antibodies released by the cells into the medium is detected with a PDX-coupled GAM Ig61Fc AK by means of ELISA after 5 more days in a culture. Cultures showing positive signals are subcloned down to individual cell clones.

The following results can be obtained:

The initial clone HEA125-mhIgG1hKappa-loxPG418 described in Example 3c may yield about 1% cells having a comparatively strong FITC fluorescence;

the cell pool described in Example 3b may yield about 15 cells having a comparatively strong FITC fluorescence per $10^8$ sorted cells.

A total of 20 sorted individual cells are expanded under the culture conditions described in Example 1a for 2-3 weeks. Thereafter, the individual clones are tested for G418 resistance as described in Example 3b. As a result 17 of the 20 tested clones may be sensitive to G418. Following PCR and sequencing of the vH gene locus by means of the PCR primers vHG418-3 and vHG418-4 (see FIG. 13B), the G418-sensitive cell line HEA125-mhloxPmyc is further expanded. Cells of this clone are washed twice with ice-cold DPBS and about $10^8$ cells per ml are stained with FITC-labeled anti-myc antibody (Mycl-9E10 epitope; Evan et al., 1985, Mol. Cell. Biol. 5, 3610-3616). Propidium iodide is used as a counterstain to identify dead cells. A strong green fluorescence of the cell line HEA125-mhloxPmyc may show in FACS.

The resulting G418-sensitive cell line HEA125-mhloxP-myc produces a monoclonal hybridoma IgG1 antibody of a defined specificity (in the example the vH domain of HEA125 with an additional c-myt-tag in the CDR3 of the vH domain) with humanized constant domains. In addition, the vH exon within the vH gene locus is flanked by 2 different loxP sites. A major part of the produced antibodies (at the order of $10^4$ to $10^6$ antibody molecules) is bound covalently at a membrane anchor on the surface of the hybridoma cells.

Example 4

Introduction of Specific Recombination Signals into the vkappa Gene Locus of HEA125 a. Chimeric DNA Sequences

As described in Example 3, several individual gene fragments are combined in the cloning vector pBS into chimeric DNA sequences. FIG. 13A shows the resulting DNA vector pBS MKappaG418M whose sequence is subsequently checked.

b. G418 Preselection

The HEA125-mhloxPmyc cell line obtained as described in Example 3d is electroporated with the linearized pBS MKappaG418M vector described in Example 4a, as described in Example 3b, and a G418 selection is subsequently carried out as described and cells are sorted in a FACS without expressed kappa chain. However, in contrast to Example 3b, FITC-labeled goat anti-human kappa antibody is used for staining. About 2,000 individual cells are sorted, as described in Example 3b, which have no kappa-specific staining (i.e. the least possible green fluorescence). These individual cells are expanded under the culture conditions described in Example 1a for 2-3 weeks.

c. Introduction of FRT Sites in the vkappa Gene Locus

From the clones described in Example 4b, the genomic DNA is isolated as described, PCR is carried out and the expected size of the PCR band is checked. The PCR primers KG418-3 and KG418-4 for this are described in FIG. 13A. 14 of the 2,000 investigated clones may have a PCR band of the expected size of about 1.9 kb. After the control sequencing of the genomic DNA (or the described PCR band), the clone HEA125-mhloxPmycFRTG418 with genomically encoded specific recombination signals (FRT0 and FRT3) is further propagated in the region of the active vkappa gene locus. The resulting cell line HEA125-mhloxPmycFRTG418 produces a monoclonal hybridoma IgG1 antibody of a defined specificity (in the example the vH domain of HEA125 with an additional c-myc-tag in the CDR3 of the vH domain) with humanized constant domains. In addition, the vH exon within the vH gene locus is flanked by 2 different loxP sites. In place of the vkappa domain, a G418 resistance gene which is flanked by 2 different FRT sites is found.

d. Specific Recombination

Cells of the about 2,000 clones described in Example 4b are pooled and, alternatively, the expanded clone HEA125-mhloxPmycFRTG418 described in Example 4c is used. The vector pBS FRTvkappa shown in FIG. 15A is electroporated into these cells. This vector codes for the genomically recombined vkappa gene of HEA125 (without leader exon) which is flanked by FRT0 and FRT3 sites. At the same time, the Flp expression vector pOG44 is electroporated into the cells (conditions for this see Example 1d). After 2-4 days in a culture (described in Example 1a), the cells are washed twice with ice-cold DPBS and about $10^8$ cells per ml are stained with PE-conjugated goat anti-human kappa antibody (Dianova). Propidium iodide is used as a counterstain to identify dead cells. After another wash step using ice-cold DPBS, individual cells having a strong PE fluorescence are sorted by means of a FACS sorter.

The following result can be obtained:

The initial clone HEA125-mhloxPmycFRTG418 described in Example 4c may yield about 1% cells having a comparatively strong PE fluorescence;

the cell pool described in Example 4b may yield about 20 cells having a comparatively strong PE fluorescence per $10^8$ sorted cells.

A total of about 20 sorted individual cells are expanded under the culture conditions described in Example 1a for 2-3 weeks. Thereafter, the individual clones are tested for G418 resistance as described in Example 4b. As a result, 18 of the 20 tested clones may be sensitive to G418, among them all of the subclones derived from the HEA125-mhloxPmycFRTG418 clone. Following PCR and sequencing of the vkappa gene locus by means of the PCR primers KG418-3 and KG418-4 (see FIG. 13A), the G418-sensitive cell line HEA125-mhRek is further expanded.

The resulting cell line HEA125-mhRek produces a monoclonal hybridoma IgG1 antibody of a defined specificity with humanized constant domains. In the example, the vH domain of HEA125 codes for an additional c-myc-tag in the CDR3 of the vH domain which can be proved by the monoclonal antibody 1-9E10 in a FACS. In addition, the active vH exon is flanked by 2 different loxP sites within the vH gene locus. The active vkappa exon is flanked by 2 different FRT sites within the vkappa gene locus. A major part of the produced antibodies is bonded covalently to a membrane anchor on the surface of the hybridoma cells.

Example 5

Preparation of a vlambda Gene Library a. Computer Analysis of Human vlambda Genes The genomic sequences of the human vlambda gene locus are known (One-megabase sequence analysis of the human immunoglobulin lambda gene locus"; Genome Res. 7:250-261(1997); Accession Numbers: D87000; D87007; D87009); D87010; D87014; D87015; D87016; D87017; D87018; D87021; D87022; D87023; D87024; X51755; X51754; see also Immunoglobulin Facts Book, Lefranc and Lefranc, which describes 33 functional vlambda genes). The computer analysis of 24 known human vlambda genes yielded no BstBI, BssHII, ClaI, DraI, HpaI, MluI, NotI, NruI, SacII, SalI, SnaBI, XhoI, EagI and no SwaI restriction sites within a region of about 300 bp upstream (in the 5' direction) of the start codon of the leader exon of the investigated gene up to the particular genomic recombination signal at the end of CDR3. In addition, the region of the J segments was studied, each from the 5' end of the 4 active $J_{lambda}$ gene segments up to about 200 bp downstream (in the 3' direction of the 3' end of the J segments in each case (see D87018 and D87023). As a result, in particular the restriction sites BssHII, MluI, NotI, SalI, XhoI and EagI are suited for cloning the diversity of human vlambda genes.

b. vlambda Gene-Specific PCR Primers vlambda gene-specific PCR primers are produced, each hybridizing to the intron between the leader exon and the particular vlambda exon (FIG. 14A). The comparable region of the active vkappa gene locus of HEA125 is approximately at the SwaI cleavage site in the intron between leader exon and vkappa exon. The primers hybridize to regions, each located about 130-170 bp upstream of the 5' end of the particular vlambda exon. The hybridization temperature of the primers is calculated to be about 65° C. each. The formula Hybridization temperature=(2° C.×number of $AT$ bp+4° C.×number of $GC$ bp)−5° C.

serves for calculating the hybridization temperature.

c. $J_{lambda}$ Gene Segment-Specific PCR Primers

The total of 4 active human $J_{lambda}$ gene segments are separated in each case by an intron from the adjacent constant clambda exons. About 89 bp (in the region of the BsaI cleavage site at HEA125) downstream of the 3' ends of the $J_{lambda}$ segments, a total of 4 $J_{lambda}$ gene segment-specific PCR primers are produced with a calculated hybridization temperature of about 65° C. each (FIG. 14A).

d. Multiplication of Human vlambda Genes by Means of PCR

The genomic DNA of human B lymphocytes is used as a template DNA. The isolation of genomic DNA is described in various laboratory manuals (see e.g. Sambrook and Russell: Molecular Cloning, a laboratory manual, $3^{rd}$ edition, Chapter 6, 2001, ISBN 0-87969-577-3). The PCR primers are described in Examples 5b and 5c. The diversity of the genomically recombined human vlambda genes is obtained by combining the 4 different $J_{lambda}$ gene segment primers with the 24 different vlambda gene-specific primers, i.e. 96 different PCR reactions are carried out. The PCR conditions for this are described in the Expand Long Template PCR System (Roche Diagnostics).

Thereafter, PCR bands having a length of about 560 bp are selected separately according to size and purified (Qiagen Gel Purification Kit). These overall 96 PCR bands each serve as a template for another PCR under the described conditions, here in place of the primers described in Example 5b, PCR primers being used whose sequences are extended at their 5' ends by the following bases:

5' attata<u>ACGCGT</u> . . . (the sequences of the vlambda gene-specific PCR primers described in Example 5b follow (a MluI restriction site required for cloning is thus inserted in the PCR product);

5' ttcGAAGTTCCTATTCTCTAGAAAGTAT-AGGAACTTC . . . (the sequences of the vlambda gene-specific PCR primers described in Example 5b follow (an FRT0 site required for an alternative cloning strategy is thus inserted in the PCR product);

5' attata <u>GCGGCCGC</u> . . . (the sequences of the $J_{lambda}$ gene segment-specific PCR primers described in Example 5c follow (a NotI restriction site required for cloning is thus inserted in the PCR product); and 5' ttcGAAGTTCCTATACTATTTGAAGAAT-AGGAACTTC . . . (the sequences of the $J_{lambda}$ gene segment-specific PCR primers described in Example 5c follow (an FRT3 site required for an alternative cloning strategy is thus inserted in the PCR product).

As described, the PCR bands are selected according to size and purified so that as a result 96 PCR band are available, each flanked by FRT0 and FRT3 sequences. Further 96 PCR bands are obtained, each flanked by MluI and NotI restriction sites.

e. Cloning of Human vlambda Genes

In the cloning vector pBS FRTvKappa 2 different FRT sites flank the vkappa exon active in HEA125 (FIG. 15A). In the presence of the FRT-specific recombinase Flp this enables the exchange of the DNA sequence flanked by the described FRT sites in vitro. First, the also AatII-cleaved DNA sequence attata<u>GACGTCACGCGTAATGTCGAC</u>TAT
<u>GCGGCCGCGACGTC</u>aatata is cloned into the FRTvkappa cloning vector cleaved using AatII. Following transfection of the resulting recombinant DNA in *E. coli*, individual clones are isolated and their sequence is checked. Here, the pBS FRTclone cloning vector (FIG. 15C) is obtained whose FRT sites flank the above or in FIG. 15C described restriction sites MluI, SalI and NotI in place of the vkappa exon shown in FIG. 15A.

Having digested the isolated vector DNA (Qiagen Plasmid Purification Kit) with the restriction enzymes MluI and NotI, the correspondingly digested 96 different PCR bands described in Example 5d are ligated in, the resulting ligation products are transfected in *E. coli* and then a highly complex mixture (>$10^6$ different transformants) is isolated from vector DNA (pBS FRTclone-vlambda) (Qiagen Plasmid Purification Kit).

Alternatively, the FRT site-flanked 96 different PCR bands described in Example 5d and circularized by means of T4-DNA ligase are incubated together with Flp recombinase and with the vector pBS FRTclone, the resulting recombination products are cleaved with the restriction enzyme SalI and transfected in *E. coli* as described above, and subsequently a highly complex mixture of vector DNA is isolated (pBS FRTclone-vlambda).

f. Specific Recombination of Human vlambda Genes in HEA125

The highly complex mixtures of human vlambda vector DNA described in Example 5e (pBS FRTclone-vlambda) are electroporated into the cells of the expanded clone HEA125-mhloxPmycFRTG418 together with the Flp expression vector pOG44 (see Example 4c), the cells are stained with FITC-labeled goat anti-human kappa antibody after 3 days, and cells are isolated by means of a FACS sorter as described. As a result, about 0.7% of the sorted cells (or about $10^6$ cells) which have a marked green fluorescence in FACS can be obtained and combined. This vlambda cell library is expanded in a cell culture.

The result of this procedure is a complex (>$10^6$ different hybridoma specificities) hybridoma library (FIG. 9) whose individual members present large quantities of respectively different human vlambda chains fused to a constant human kappa domain on the surface in each case.

A preferred embodiment by which a highly complex mixture like the described pBS FRTclone-vlambda can be obtained is not shown. Here, in place of the PBSIISK+ cloning vector a vector replicating episomally in eukaryotic cells is used (based e.g. on pCEP4, pREP7, pREP10, pEBVHis or pREP4 from Invitrogen). The Flp recombinase is encoded by a controllable expression cassette which is integrated stably and chromosomally. Systems of this kind are offered inter alia by Invitrogen company (GeneSwitch™ System K1060-01; T-Rex™ System K1020-01).

Example 6

Production of a vkappa Gene Library a. Computer Analysis of Human vkappa Genes

The genomic sequences of the human vkappa gene locus are known (Immunoglobulin Facts Book, Lefranc and Lefranc, 2001, Academic Press, ISBN 0-12-441351-X). The computer analysis of 34 known functional human vkappa genes yielded no BglI, BssHII, BstBI, ClaI, EagI, HindIII, MluI, NotI, NruI, PvuI, SacII, SfiT, SnaBI, SpeI and no StuI restriction sites within a region of about 200-300 bp upstream of the leader exon of the investigated genes up to the particular genomic recombination signal at the end of CDR3. In addition, the region of the J segment was investigated from the 5' end of the active $J1_{kappa}$ gene segment to about 200 bp downstream of the 3' end of the active $J5_{kappa}$ gene segment (see accession number J00242). As a result, in particular the restriction sites BssHII, EagI, HindIII, MluI, NotI, SfiI and SpeI are suited for cloning the diversity of human vkappa genes. The restriction enzyme SalI only cleaves once outside the gene IGKV1D-43.

b. vkappa Gene-Specific PCR Primers vkappa gene-specific PCR primers are produced, each hybridizing to the intron between the leader exon and the particular vkappa exon (FIG. 14B). The comparable region of the active vkappa gene locus of HEA125 is located approximately at the SwaI cleavage site in the intron between leader exon and vkappa exon. The primers hybridize to regions, each about 130-170 bp upstream of the beginning of the particular vkappa exon. The hybridization temperature of the primers is calculated to be about 65° C. each.

c. $J_{kappa}$ Gene Segment-Specific PCR Primers

The total of 5 active human $J_{kappa}$ gene segments are clustered other than the $J_{lambda}$ gene segments, so that always the same constant ckappa exon is used which is separated from the clustered $J_{kappa}$ segments by an intron. About 89 bp (the comparable region of HEA125 is at the BsaI cleavage site) downstream of the 3' ends of the different $J_{kappa}$ segments, a total of 5 $J_{kappa}$ gene segment-specific PCR primers are produced with a calculated hybridization temperature of about 65° C. each (FIG. 14B).

d. Multiplication of Human vkappa Genes by Means of PCR

As described in Example 5d for vlambda, the diversity of the genomically recombined human vkappa genes is obtained by combining the 5 different $J_{kappa}$ gene segment primers with 34 different functional vkappa gene-specific primers, i.e.

170 different PCR reactions are carried out. These altogether 170 PCR bands each serve as a template for further PCR reactions, here as described in Example 5d the employed primers being extended at their 5' end by a restriction site or by FRT0 or FRT3. As described, the PCR bands are selected according to their size and purified so that as a result 170 PCR bands are available (about 600 bp; each flanked by FRT0 and FRT3 sequences). Another 170 PCR bands are obtained (about 550 bp), each flanked by MluI and NotI restriction sites.

e. Cloning of Human vkappa Genes

Having digested the isolated vector DNA of pBS FRTclone described in Example 5e (FIG. 15C) by means of the restriction enzymes MluI and NotI, the correspondingly digested 170 different PCR bands which are described in Example 6d and flanked by MluI and NotI sites are ligated in, the resulting ligation products are transfected in *E. coli* and then as described in Example 5e a highly complex mixture (>10$^6$ different transformants) of vector DNA (pBS FRTclone-vkappa) is isolated.

Alternatively, the 170 different PCR bands, all of which are circularized, flanked by FRT sites and described in Example 6d are incubated together with Flp recombinase with the vector pBS FRTvkappa, the resulting recombination products are cleaved using the SalI restriction enzyme and transfected in *E. coli* as described in Example 5e and subsequently a highly complex mixture of vector DNA (pBS FRTklone-vkappa) is isolated.

f. Specific Recombination of Human vkappa Genes in HEA125

As described for vlambda in Example 5f, the highly complex mixtures of human vkappa vector DNA (pBS FRTclone-vkappa) described in Example 6e are electroporated together with the Flp expression vector pOG44 into the cells of the expanded cell line HEA125-mhloxPmycFRTG418, stained using FITC-labeled goat anti-human kappa antibody and cells are isolated by means a FACS sorter as described. As a result, about 0.8% of the sorted cells (or about 10$^6$ cells) which in the FACS may have a marked green fluorescence can be obtained and combined. This vkappa cell library is expanded in a cell culture.

The result of this procedure is a complex (>10$^6$ different hybridoma specificities) hybridoma library (FIG. 9) whose individual members present on the surface major quantities of respectively different human vkappa chains each fused to a constant human kappa domain.

Example 7

Production of an Antibody Library a. Computer Analysis of Human vH Genes

The genomic sequences of the human vH gene locus are known (EMBL database accession numbers X97051; S64822; AB019437; AB019438; AB019439; AB019440; AB019441; see also the Immunoglobulin Facts Book, Lefranc and Lefranc, 2001, Academic Press, ISBN 0-12-441351-X). The computer analysis of the 44 functional human vH genes listed in accession numbers X97051; S64822; AB019437; AB019438; AB019439; AB019440 and AB019441 yielded no BssHII, ClaI, MluI, NheI, NotI, NruI, PvuI, SalI, SfiI, SwaI and no XhoI restriction sites within a region of 300 bp upstream of the 5' end of the leader exon of the investigated genes up to the respectively vH gene-flanking genomic recombination signal. In addition, the region of the J$_H$ segments was studied from the 5' end of the active J1$_H$ gene segment to about 200 bp downstream of the 3' end of the active J6H gene segment (see accession numbers X97051; S64822). As a result, in particular the restriction sites BssHII, MluI, NheI, NotI, SalI, SfiI and XhoI are suited for cloning the diversity of human vH genes. The restriction sites BssHII, MluI, NotI and SalI (with the exception of the gene IGKV1D-43) do not occur in the investigated vlambda and vkappa gene regions either.

b. vH Gene-Specific PCR Primers vH gene-specific PCR primers, each hybridizing about 182 bp upstream of the 5' end of the particular vH leader exon to the particular vH genes are produced (FIG. 14C). The hybridization temperature of the primers is calculated to be about 65° C. in each case.

c. J$_H$ Gene Segment-Specific PCR Primers

The total of 6 active human J$_{kappa}$ gene segments are clustered like the J$_{kappa}$ gene segments, so that always the same constant CH exons are used (but as a function of a possibly conducted class switch). The CH1 exon is here separated from the clustered J$_H$ gene segments by an intron. In each case, about 83 bp (the comparable region of HEA125 is at the BSu36I cleavage site) downstream of the 3' end of the particular J$_H$ gene segments a total of 6 J$_H$ gene segment-specific PCR primers are produced with a calculated hybridization temperature of about 65° C. in each case (FIG. 14C).

d. Multiplication of Human vH Genes by Means of PCR

As described in Example 5b for lambda, the diversity of the genomically recombined human vH genes is obtained by combining the 6 different J$_H$ gene segment primers with the 44 different vH gene-specific primers, i.e. 6×44=264 different PCR reactions are carried out. Here, 5 of the 6 J$_H$ gene segment-specific PCR primers showed may show additional, relatively high-molecular PCR bands which are separated in a TAE agarose gel from the band having a length of about 790 Bp in each case. This is due to the fact that e.g. the J2$_H$ PCR primer multiplies both genomically recombinant vHJ2$_H$ fusions and vHJ1$_H$ fusions.

As described in Example 5d, this total of 264 PCR bands having a size of about 790 bp each serve as a template for another PCR having the described conditions, in this case the primers described in Example 7b being exchanged with PCR primers whose sequences are extended at their 5' ends by the following bases:

5' attata <u>ACGCGT</u> . . . (the sequences of the vH gene-specific PCR primers described in Example 7b follow (an MluI restriction site required for cloning is thus inserted in the PCR product);

5' ttc<u>ATAACTTCGTATAATGTATGC TATACGAAGTTAT</u> . . . (the sequences of the vH gene-specific PCR primers described in Example 7b follow (a loxP site required for an alternative cloning strategy is thus inserted in the PCR product);

5' attata <u>GCGGCCGC</u> . . . (the sequences of the J$_H$ gene segment-specific PCR primers described in Example 7c follow (a NotI restriction site required for cloning is thus inserted in the PCR product); and 5' cct<u>ATAACTTCGTATAATGTATAC TATACGAAGTTAT</u> . . . (the sequences of the JH gene segment-specific PCR primers described in Example 7c follow (a loxP511 site required for an alternative cloning strategy is thus inserted in the PCR product).

As described, the PCR bands are selected as to their size and purified so that as a result 264 PCR bands having a size of about 860 bp are available, each flanked by loxP and loxP511 sequences. Further 264 PCR bands are obtained, each flanked by MluI and NotI restriction sites.

e. Cloning of Human vH Genes

Having digested the isolated vector DNA pBS loxPclone described in FIG. 15D (Qiagen Plasmid Purification Kit) using restriction enzymes MluI and NotI, the correspondingly digested 264 different PCR bands described in Example 7d are ligated in, the resulting ligation products are transfected in *E. coli* and then a highly complex mixture (>$10^6$ different transformants) is isolated from vector DNA as described in Example 5e (pBS loxpclone-vH).

Alternatively, the 264 different PCR bands flanked by loxP sites and described in Example 7d are incubated together with Cre recombinase with the vector pBS loxpclone, the resulting recombination products are cleaved using the SalI restriction enzyme and transfected in *E. coli* as described above, and thereafter a highly complex mixture of vector DNA (pBS loxPclone-vH) is isolated.

f. Specific Recombination of Human vH Genes in HEA125

As described in Example 5f for vlambda, the highly complex mixtures, described in Example 7e, of human vH vector DNA (pBS loxPclone-vH) are electroporated into the cells together with the Cre expression vector pMC-Cre. The vlambda or vkappa cell libraries described in Examples 5f and 6f are used for this purpose. The cells are stained with PE-conjugated goat anti-human IgG antibody and simultaneously with FITC-labeled monoclonal anti myc1-9E10 antibody. As described, cells are isolated by means of a FACS sorter. As a result, about 0.8% of the sorted cells (or about $10_7$ cells) which in the FACS may show a strong red fluorescence and simultaneously the least possible green fluorescence can be obtained and combined. This antibody cell library is expanded in a cell culture and aliquots thereof are frozen in liquid nitrogen.

The result of this procedure is a complex (>$10^7$ different hybridoma specificities) antibody library (FIG. 9) whose individual members present on the surface major quantities of respectively different human IgG1 antibodies each fused to constant human domains. At the same time, the hybridoma cells secrete the major part of the produced antibodies into the surrounding medium. The individual processing steps here largely orient themselves by the prior art as known.

The vlambda domains of this antibody library are fused to the constant kappa domain in the example. In a further preferred embodiment (not shown), Example 1e is modified for this reason in so far as a vector which after the homologous recombination codes for a constant human lambda domain is used in place of the pBS MhKappaM vector shown in FIG. 12A.

Example 8

Selection of Monoclonal Antibodies by Means of FACS/Magnetobeads

The antibody library described in Example 7f is cultured as described in Example 1a. The expanded cells are washed twice with ice-cold DPBS and about $10^7$ cells per 400 µl are stained with FITC-conjugated BSA. Propidium iodide (1 µg/ml) is used as a counterstain to identify dead cells. Following another wash step using ice-cold DPBS, the cells are sorted by means of a FACS sorter. As a result, about 15 cells which may have a comparatively strong green fluorescence can be found per $10^7$ hybridoma cells. The sorted individual cells are expanded as described in Example 1a (under certain circumstances together with feeder cells) and the supernatant including the contained secreted antibodies is studied in a Western blot for antigen specificity. As a result, the supernatant of 2 clones may react with BSA (molecular weight about 68 kD) and 5 further clones may have an FITC-BSA-specific staining (molecular weight about 72 kD).

At the same time, about $10^8$ cells of the antibody library described in Example 7f are washed twice with ice-cold DPBS and then incubated in 5 ml DPBS buffer for 5 minutes using BSA or using ovalbumin-coated magnetobeads. Unbound cells are washed away by means of a magnet and the other magnetobead-bound cells are cultured as described in Example 1a. As a result, the supernatant of the cells enriched with BSA magnetobeads may react with BSA (molecular weight about 68 kD) but not with ovalbumin in a Western blot, while the supernatant of the cells enriched with ovalbumin magnetobeads may show no staining with BSA.

Example 9

Selection of More Affine Monoclonal Antibodies by Means of FACS

Each of the anti-FITC antibodies secreted by the 5 FITC-BAS-specific clones described in Example 8 is purified by means of protein G sepharose and part thereof is conjugated with horseradish peroxidase (anti-FITC-PDX antibodies). The concentration of the different purified antibodies is adjusted to 1 mg/ml in PBS each.

An ELISA plate is coated with FITC-BSA (each 0.1 µg in 100 µl PBS), blocked (with 1% milk powder in 200 µl PBS) and the 5 different peroxidase-conjugated antibodies (each diluted 1:2000 in 100 µl PBS-Tween 20) are competed with increasing amounts of the non-peroxidase-conjugated antibodies. The non-peroxidase-conjugated antibodies are preincubated with the coated FITC antigen for 10 minutes each. After intermediate wash steps, residual bound peroxidase is detected with the substrate OPD/$H_2O_2$.

In these competition experiments, the anti-FITC2 antibody produced by the clone anti FITC2 may prove to be the comparatively most affine antibody. If in each case peroxidase-conjugated anti-FITC1, 2, 3, 4 or 5 antibody diluted 1:2000 is given, a semi-maximum inhibition of the ELISA signal may follow from the:

anti-FITC1-POX antibody with anti-FITC2 antibody diluted 1:1000;
anti-FITC2-POX antibody with anti-FITC2 antibody diluted 1:500;
anti-FITC3-POX antibody with anti-FITC2 antibody diluted 1:2000;,
anti-FITC4-POX antibody with anti-FITC2 antibody diluted 1:2000;
anti-FITC5-POX antibody with anti-FITC2 antibody diluted 1:5000.

Then, $10^6$ cells of the anti-FITC2 clone are mixed with about $10^7$ cells of the anti-FITC5 clone, washed twice with ice-cold DPBS, stained with FITC-BSA (10 µg/ml) and simultaneously with PE-conjugated protein G (10 µg/ml). Propidium iodide is used as described to identify dead cells. After another wash step using DPBS, the cells are analyzed in a FACS (FIG. 10). Here, about 10% of the living cells may have a ratio of green to red fluorescence of about 0.8 (+/−0.2) while about 90% of the living cells may have a ratio of green to red fluorescence of about 0.08 (+/−0.03).

As described above, about $10^6$ cells of these cell populations are sorted separately in each case, the genomic DNA is isolated therefrom and used as a template for a PCR with primers vHG418-3 and -4 (FIG. 13B). The same is done with cells of the clones anti FITC2 and anti FITC5. The PCR bands are separated in a 1% TAE agarose gel according to size, the distinguishably slightly greater PCR band of the sorted cell population corresponds to the clone anti-FITC5 at an expected ratio of green to red fluorescence of about 0.8 (about 1.95 kb), while the also corresponding, slightly smaller PCR band of the sorted cell population corresponds to the anti-FITC5 clone at an expected ratio of green to red fluorescence of about 0.08.

This example shows a very simple method to discover highly affine monoclonal antibodies. Here, an easily conductible normalization of the number of presented antibodies enables an "on line" affinity comparison of the discovered antibody specificities (FIG. 10).

Example 10

"Chain-Shuffling" and Selection of Highly Affine Monoclonal Antibodies

The diversity, described in Example 7e, of the vH genes is recombined into the expanded cell line described in Example 9 by means of a Cre expression vector as described in Example 7f. The resulting anti-FITC antibody library is stained with FITC-BSA and simultaneously with PE-conjugated protein G as described in Example 9.

As a result, about 70% of the living cells may have a ratio of green to red fluorescence of about 0.08 to (+/−0.03) while about 0.02% of the living cells may have a ratio of green to red fluorescence of 0.2 to 0.7 (+/−0.1).

This example shows a very simple method to produce a group of hybridomas from which comparatively highly affine monoclonal antibodies can be isolated.

Example 11

Conduction of a Somatic Hypermutation to Obtain Highly Affine Antibodies

The cDNA sequences of the genes RAD54, RecQ4, polX mu, RAD51B, XRCC2 and XRCC3 are known. First, the cDNA sequences of the genes RAD54, RecQ4 and/or polX mu are each cloned under the control of an RSV promoter into the eukaryotic expression vector pREP4 (Invitrogen) and the correct sequence is checked. Here, the expression vectors pREP4-RAD54, pREP4-RecQ4 and pREP4-polXmu and the anti-sense RNA expression vectors pREP4-RAD51B, pREP4-XRCC2 and pREP4-XRCC3 are obtained.

Circular DNA of the vectors pREP4-XRCC2, pREP4-RAD54, pREP4-RecQ4 and pREP4-polXmu are mixed at a ratio of 1:1:1:1 and electroporated into the expanded anti-FITC5 cell line described in Example 9 under the optimized electroporation conditions described in Example 1d. Thereafter, the cells are cultured for 2-3 days as described in Example 1a. Optionally, cells which have taken up the episomally replicating pREP4 vectors can then be selected using hygromycin. Thereafter, the cells are stained with FITC-BSA and simultaneously with PE-conjugated protein G as described in Example 9. As a result, about 90% of the living cells may have a ratio of green to red fluorescence of about 0.08 (+/−0.03) while about 0.002% of the living cells may have a ratio of green to red fluorescence of 0.2 to 0.7 (+/−0.2).

This example shows another very easy method to produce a group of hybridomas from which comparatively highly affine monoclonal antibodies can be isolated.

Example 12

Production of a Bispecific Antibody a. Chimeric DNA Sequences

Figure 17A:
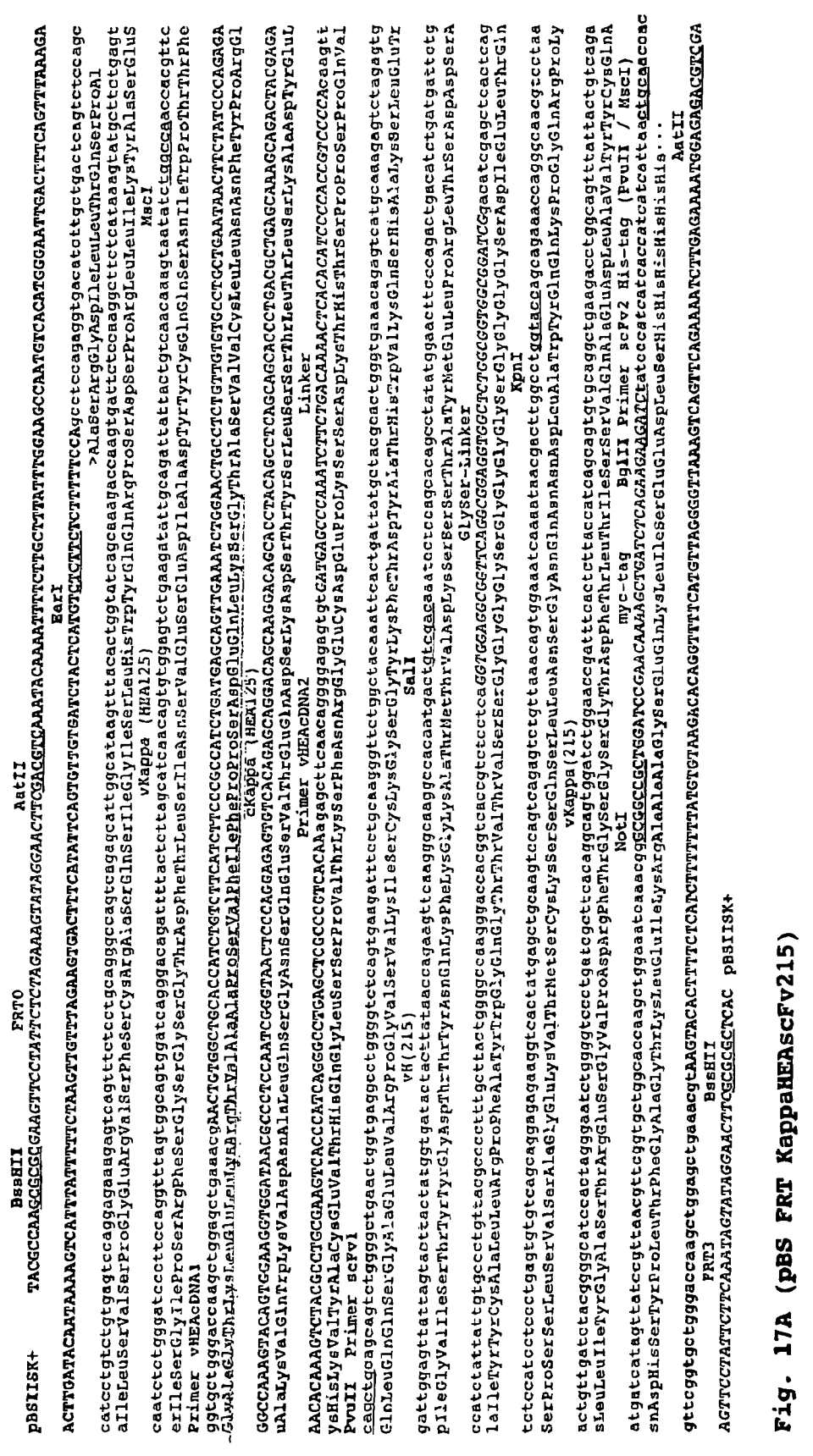

Several individual gene fragments are combined in the cloning vector pBSIISK+ into chimeric DNA sequences. The individual gene fragments are here produced by means of PCR (Roche Diagnostics; Expand Long Template PCR System; see also for the PCR conditions). cDNA of the murine hybridoma cell line HEA125 serves as a template for the gene sequences and an expression vector for the scFv antibody 215 serves as a template for the gene sequences (Kontermann et al., 1995, Characterization of the epitope recognized by a monoclonal antibody directed against the largest subunit of *Drosophila* RNA polymerase II. Biol. Chem. Hoppe-Seyler 376, 473-481). The region of the linker sequence between ckappa(HEA) and the scFv(215) antibodies is produced by a synthetic overhanging PCR oligonucleotide. As a result, the vector pBS FRT KappaHEAscFv215 is obtained. FIG. 17A shows the resulting chimeric DNA sequence whose sequence is subsequently checked.

b. Specific Recombination in the vKappa Gene Locus

The described vector pBS FRT KappaHEAscFV215 is electroporated into the cell line HEA125-mhloxPmyc-FRTG418. At the same time, the Flp expression vector pOG44 is electroporated into the cells (conditions for this see Example 1d). After 2-4 days in a culture (conditions for this see Example 1a), the cells are washed twice with ice-cold DPBS and about $10^8$ cells per ml are stained using PE-conjugated goat anti-mouse kappa antibody (Southern Biotechnology Associates). Propidium iodide is used as a counterstain to identify dead cells. After another wash step using ice-cold DPBS, individual cells having a strong PE fluorescence are sorted by means of a FACS sorter. Here, the initial clone HEA125-mhloxPmycFRTG418 described in Example 12a may yield about 0.1% cells having a comparatively strong PE fluorescence. Thereafter, 5 sorted individual cells are expanded under the culture conditions described in Example 1a for 2-3 weeks. The resulting clones are then stained with PE-labeled goat anti-mouse kappa antibody again as described and analyzed in a FACS. Two clones having a marked red fluorescence signal are further propagated. The genomic DNA of these clones is multiplied by means of PCR and the primers KG418-3 and KG418-4 (primers see FIG. 13A, see also FIG. 17A) and is sequenced.

The cell line HEA125-mhloxPmycFRTscFv215 obtained as a result produces a bispecific monoclonal hybridoma IgG1 antibody of a defined specificity (in the example the vH domain of HEA125 with an additional c-my-tag in the CDR3 of the vH domain) with humanized constant IgG1 domains. In addition, the vH exon is flanked by 2 different loxP sites within the vH gene locus. In the region of the active murine vkappa gene locus flanked by FRT sites, the vkappa domain of HEA125 is encoded, which is fused to the murine ckappa domain, a linker sequence and the scFv215 antibody.

Example 13

Production of a Bifunctional Antibody

Figure 17B:
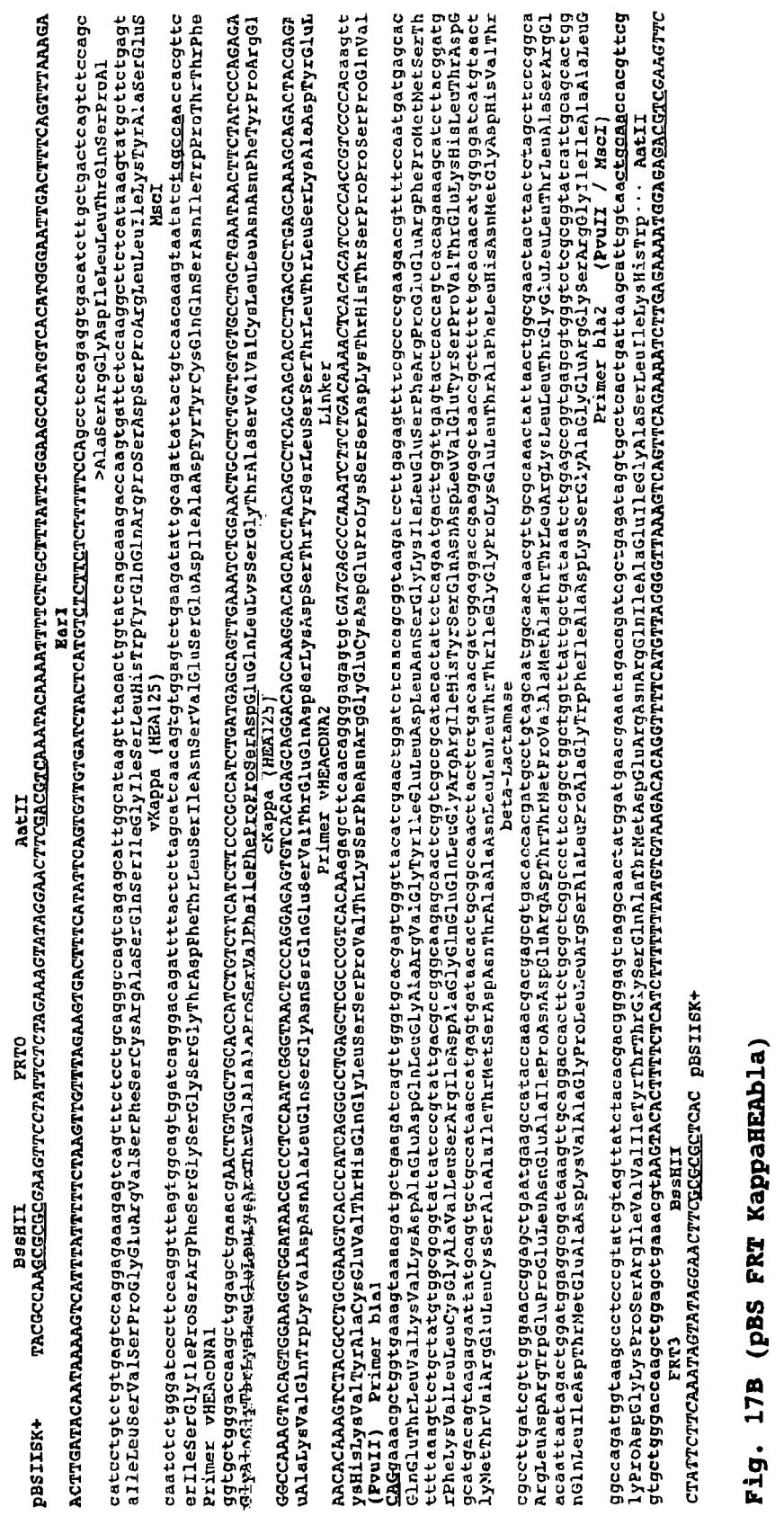

As described in Example 12, the cell line HEA125-mhloxPmycFRTG418 is electroporated with a chimeric DNA, stained using PE-conjugated goat anti-mouse kappa antibody, individual cells having a comparatively strong PE fluorescence are sorted, individual clones are expanded and the genomic sequence is checked. In contrast to Example 12, here the vector pBS FRT KappaHEAbla is used instead of the described vectors pBS FRT KappaHEAscFv215 (FIG. 17B). The described initial clone HEA125-mhloxPmycFRTG418 may yield about 0.1% cells having a comparatively strong PE fluorescence.

The resulting cell line HEA125-mhloxPmycFRTbla produces a monoclonal hybridoma IgG1 antibody of a defined specificity (in the example the vH domain of HEA125 with an additional c-myc-tag in the CDR3 of the vH domain) with humanized constant IgG1 domains. In addition, the vH exon is flanked by 2 different loxP sites within the vH gene locus. In the region of the active murine vkappa gene locus flanked by FRT sites, the vkappa domain of HEA125 is encoded, which is fused to the murine ckappa domain, a linker sequence and the gene for the beta lactamase.

Example 14

Modification of the Antibody Specificity by Means of Specific Recombination

Figures 18A, 18B:
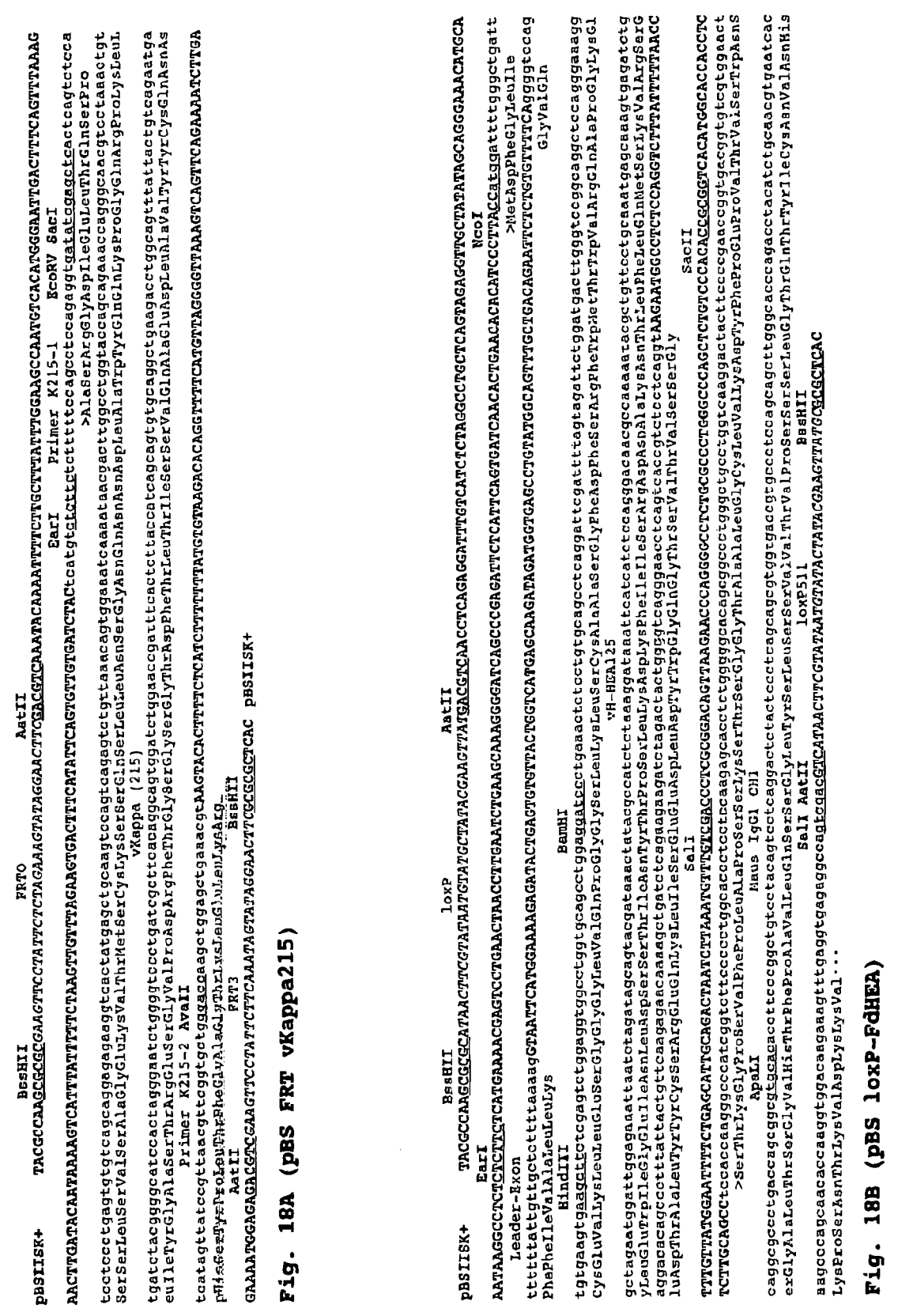

As described in Example 12, the cell line HEA125-mhloxPmycFRTG418 is electroporated with a chimeric DNA and stained using PE-conjugated goat anti-human kappa antibody, individual cells with comparatively strong PE fluorescence are sorted, individual clones are expanded and the genomic sequence is checked. In contrast to Example 12, here the vector pBS FRT Kappa215 is used instead of the described pBS FRT KappaHEAscFv215 (FIG. 18A). The described initial clone HEA125-mhloxPmycFRTG418 may yield about 0.1% cells having a comparatively strong PE fluorescence.

The resulting cell line HEA125-mhloxPmycFRT215 produces a monoclonal hybridoma IgG1 antibody of a defined specificity (in the example the vH domain of HEA125 with an additional c-myc-tag in the CDR3 of the vH domain) with humanized constant domains. In addition, the vH exon is flanked by 2 different loxP sites within the vH gene locus. In the region of the active murine vkappa gene locus flanked by FRT sites, the vkappa domain of the antibody 215 is encoded. An analogous procedure yields a different vH domain.

Example 15

Production of a Fab Antibody by Means of Specific Recombination a. Chimeric DNA Sequences Several individual gene fragments are combined in the cloning vector PBSIISK+ into chimeric DNA sequences. The individual gene fragments are here produced by means of PCR (Roche Diagnostics; Expand Long Template PCR System; see also for the PCR conditions). cDNA of the murine hybridoma cell line HEA125 serves as a template for the gene sequences. As a result, the vector pBS loxP-FdHEA is obtained. This vector encodes the vH domain of HEA 125 fused with the murine IgG1-CH1 domain. FIG. 18B shows the resulting chimeric DNA sequence whose sequence is subsequently checked.

b. Specific Recombination in the vH Gene Locus

The vector pBS loxP-FdHEA described in Example 15a is electroporated into the HEA125-mhRek cell line described in Example 4d together with the Cre expression vector pMC-Cre as described in Example 1d and subsequently about 2,000 clones are propagated separately by limited dilution of the employed about $10^7$ cells. An ELISA plate is coated with 100 µl each of the particular cell culture supernatant of the described 2,000 clones, blocked (using 1% milk powder in 200 µl PBS) and then stained using peroxidase-conjugated 1-9E10 anti-myc antibody or peroxidase-coupled goat anti-mouse IgG antibody (Dianova) (each diluted 1:2000 in 100 µl PBS). After intermediate wash steps, residually bound peroxidase is proved with the OPD substrate. As a result, 3 of the investigated clones may show an increased signal in the staining with peroxidase-coupled goat anti-mouse IgG antibody, while at the same time no detectable signal may be proved in the staining with peroxides-conjugated 1-9E10-anti-myc antibody. The genomic sequence of the clones is checked and as a result the clone HEA125 Fab is propagated.

The resulting cell line HEA125 Fab secretes a monoclonal Fab antibody fragment of a defined specificity (in the example the vH and vkappa domains of HEA125) with humanized constant kappa domain. In addition, the vH-CH1 exon is flanked by 2 different loxP sites within the vH gene locus. The vkappa exon is flanked by 2 different FRT sites.

Example 16

T Cell Receptor Library

The gene loci of the human alpha and beta or gamma and delta T cell receptors are known (see: T-Cell Receptor Facts Book, Lefranc and Lefranc, 2001, Academic Press, ISBN 0-12-441352-8). Based on the cell line HEA125-mhRek (Example 4) the constant kappa domain is initially exchanged with a constant domain of the alpha T cell receptor quite analogously to the procedure described in Example 1e. Here, only the coding DNA sequences of the N-terminal 121 amino acids of the constant domain (and the linker to the membrane domain) of the alpha T cell receptor are used, followed by a stop codon, i.e. without membrane anchor and/or without the C terminal 20 amino acids. Thereafter, the constant CH1 domain of the IgG1 is exchanged with the N-terminal 150 amino acids of the constant domain of the beta1 T cell receptor analogously to Example 1f (fused to the hinge exon of an IgG1). The splice donor of this chimeric exon is derived from the hinge region of an IgG1. The cloning and then following specific recombination of the diversity of the variable domains of the T alpha and T beta T cell receptors is effected analogously to Examples 6 and 7 with gene segment-specific primers or by means of Cre and Flp. A T cell receptor library is formed, the particular beta chain being fused to the hinge, CH2 and CH3 domains of an IgG1. A considerable part of these fusion proteins is presented on the cell surface on account of the membrane-bound splice variant of the IgG1 portion.

Specific binders are selected analogously to Example 8 or 9. Alternatively, the cells of the T cell receptor library are stained with PE-labeled protein G while the cells of the lymphoma cell line Jurkat are stained using FITC-labeled anti-CD5 antibody. $10^7$ of the thus stained cells each are washed twice with DPBS, mixed with one another and incubated on ice in 1 ml RPMI medium for 30 min. Thereafter, doublettes which have a green-red double fluorescence are sorted in the FACS sorter. More affine (or less affine) binders are selected analogously to Examples 10 and 11.

Example 17

T Cell Receptor Gene Loci

The gene loci of the active human alpha and beta T cell receptors are known (T-Cell Receptor Facts Book, Lefranc and Lefranc, 2001, Academic Press, ISBN 0-12-441352-8).

Based on the human T cell line Jurkat, the active variable domains of the T alpha and T beta cell receptors are initially flanked with FRT or with loxP sites analogously to Examples 3 and 4. Thereafter, the cloning and then specific recombination of the diversity of the variable domains of the T alpha and T beta cell receptors are carried out analogously to Examples 6 and 7. Gene segment-specific primers or the specific recombinases Cre and Flp are used for this purpose. Here, a T cell receptor library having membrane-bound T cell receptors is formed. Both chains of the T cell receptor are anchored in the cell membrane on account of their natural membrane anchor. The specific binders are selected analogously to Example 8 or 9. More affine (or less affine) binders are selected analogously to Examples 10 and 11.

Example 18

Specific Recombination into Suitable Gene Loci a. Cell Line with Specific Recombination Signals in an Active Gene Locus The linearized vector pBS MvHG418MdeltaPGK is electroporated into the Jurkat cell line (FIG. 13B) and G418-resistant cells are selected as described in Example 3b. The cell clone Jurkat G418 is thus obtained by limited dilution.

b. Chimeric DNA

The vector pBS loxP-IgG1 described in FIG. 16 is electroporated into the cell line Jurkat G418 together with the Flp expression vector pOG44, as described in Example 1d, and then about 500 clones are propagated separately by limited dilution of the employed about $10^7$ cells. Of these 500 clones 4 clones may be G418-sensitive. The sequencing of genomic DNA by means of FRT-specific PCR primers yields the Jurkat loxP-IgG1 cell line.

c. Specific Recombination

The vector pBS loxPvH (FIG. 15B) is then electroporated together with the Cre expression vector pMC-Cre into the cells of the expanded Jurkat loxP-IgG1 cell line described in Example 18b, the cells are stained using FITC-labeled goat anti-human IgG1 antibody after 3 days and cells are isolated by means of FACS sorter as described. As a result, 425 of about $10^6$ cells may be sorted and 10 clones thereof, which may show a marked green fluorescence in FACS are propagated separately. After the sequencing of PCR-amplified genomic DNA, the result of this procedure is the Jurkat lox-PvHEAIgG1 cell line. This cell line codes for the vH domain of HEA125 while fused to the constant human CH1, CH2 and CH3 domains. Part of this heavy antibody chain is presented on the surface of the cell line Jurkat loxPvHEAIgG1 cells.

A variation of this procedure is shown in FIG. 6 by way of diagram. Here, a loxP-flanked scFv antibody gene, fused to hinge, CH2, CH3, M1 and M2 domains, is recombined as a gene cassette into the pre-selected cell line Jurkat G418. This recombination event can be selected directly on account of the surface expression of the recombined scFv antibody. The same applies to the optionally following specific recombination of a diversity of different scFv antibody gene cassettes.

Alternatively, already present cell lines can be used as a starting material, which are obtained analogously to the procedure described in Example 18a. Examples are the cell lines Flp-In™-293 (R750-07), Flp-In™-CV-1 (R752-07) and Flp-In™-CHO (R758-07) sold by Invitrogen.

In another preferred experimental procedure, a simple selection of the desired recombination events is enabled for both the integration of the resistance gene into the recombinase cassette (see Example 18a, G418 selection) and the excision of the resistance gene by Flp or Cre (see Example 18b). An example of this is the fusion of the neophosphoryl transferase II gene to the gene of herpex simplex thymidine kinase. Gancyclovir is used for the selection of cells which have lost the integrated chimeric gene (Syntex #115561). It is converted into a cytotoxin in the presence of thymidine kinase (TK) (Masour et al., 1988, Nature 336, 348-352). Before that it is possible to produce quite easily cell lines whose endogenous TK no longer functions with gancyclovir by means of selection.

Example 19

"Exon Trap" and Surface Presentation a. "Exon Trap" Cell Line

The vector pBS loxP-IgGdeltaCH1 (FIG. 16) is electroporated into the cells of the expanded Jurkat G418 cell line described in Example 18a together with the Flp expression vector pOG44, as described in Example 1d, and then 500 clones are propagated separately by limited dilution of the employed about $10_7$ cells. Of these 500 clones 5 clones may be G418-sensitive. The sequencing of genomic DNA by means of the FRT-specific PCR primers yields the Jurkat loxP-IgG1deltaCH1 cell line. This cell line encodes the constant hinge, CH2, CH3, M1 and M2 domains of an IgG1 antibody under the control of an endogenous Jurkat promoter. In the region of the variable domains, a loxP exchange cassette is found. The splice acceptor at the 5' end of the hinge exon is shown in FIG. 16 together with the open reading frame.

b. Genomic DNA

Human lymphocytes are somewhat purified on a Ficoll gradient according to standard methods and the genomic DNA is obtained therefrom (see e.g. Sambrook and Russell: Molecular Cloning, a laboratory manual, $3^{rd}$ edition, 2001, ISBN 0-87969-577-3). This DNA is excised using AatII, NotI, MluI or SalI and selected in a 0.8% TAE agarose gel according to their size each (1-5 kb). The size-selected DNA is then cloned into the pBS loxPclone vector described in FIG. 15D and then a highly complex mixture (>$10^6$ different transformants) is isolated from the vector DNA (Qiagen Plasmid Purification Kit).

c. Specific Recombination

The highly complex mixture, described in Example 19b, of vector DNA is electroporated into the cells of the expanded clone Jurkat loxP-IgG1deltaCH1 together with the Cre expression vector pMC-Cre, the cells are stained using FITC-labeled goat anti-human IgG antibody after 3 days and cells are isolated by means of a FACS sorter as described. As a result, 125 of about $10^8$ cells which may have a marked green fluorescence in FACS, may be sorted and combined. This exon trap library is expanded in a cell culture.

The result of this procedure is an exon-trap library whose individual members each present on the surface of the cells different human exon-coded domains each fused to constant CH2 and CH3 domains.

Example 20

Search for Differences in 2 Complex Mixtures/Search for Tumor-Associated Antigens About $10^8$ normal unlabeled human T lymphocytes purified somewhat on a Ficoll gradient are mixed with about $10^7$ cells of the antibody library described in Example 7 in 5 ml DPBS buffer and preincubated on ice for 10 min. The cells of the antibody library described in Example 7 are previously stained using PE-labeled protein G as described above. Then, about $10^6$ cells of the lymphoma cell line Jurkat are stained with FITC-labeled anti-CD5 antibody and added. The Jurkat cells were are irradiated directly beforehand additionally with 400 rad. After another 20 min on ice, doublettes are sorted in the FACS sorter, which had have a green-red double fluorescence. As a result, 5 individual cells may be sorted and expanded. The cell culture supernatant of one of these 5 cell lines may yield in the FACS a specific signal as to Jurkat cells as compared with the staining of lymphocytes obtained from the blood. The antibodies secreted into the medium are detected by FITC-labeled goat anti-human IgG antibody (Dianova).

The procedures described in the above examples can be varied or combined in many ways by the person skilled in the art, e.g.:

- a constant murine kappa domain can also be exchanged with a constant human lambda domain (Example 1e);
- in each case one of a total of 9 different exon trap vectors having shifted splice donor or splice acceptor sites yields a gene product in the proper reading frame, a leader exon being given or not (in the latter case only 3 different exon trap vectors are required; Example 19);
- in principle, every active gene locus is suited to produce based on a cell line a diversity of different cells or thus associated gene products by specific recombination (Examples 3, 4, 17, 18, 19);
- even equal specific recombination signals can flank the variable sequences (Examples 3, 4, 12, 13, 14, 15, 16, 17, 18, 19);
- or equal inverted recombination signals can flank the variable sequences:
- or several (many) successive variable sequences which are flanked by recombination signals are recombined (FIG. 6);
- the recombinase protein per se can be used in place of a recombinase expression vector;
- said recombinase protein can be fused to a Tet repressor domain to thus increase the recombination efficiency of DNA sequences with Tet operator sites;
- a cell line can be produced, in particular inducibly, which produces the required specific recombinases, (Examples 3d, 4d), e.g. the Cre activity being verifiable very easily by means of the pSVlacZT vector;
- the diversity of the antibody genes (Examples 5, 6, 7, 18) can also be effected by the chemical synthesis of many different CDRs within one or only some given antibody gene frameworks;
- or by the multiplication of cDNA or of svFv antibody libraries (Example 18) using PCR;
- the diversity of the recombinant variable antibody genes can be preselected by negative selection using gancyclovir (Example 18);
- other selectable gene segments can be inserted instead of a G418 resistance or a myc epitope (Examples 3, 4, 18) (e.g. EGFP);
- the application of both a positive (e.g. G418) and negative (e.g. gancyclovir) selectable recombination cassette is possible (Example 18);
- libraries (Examples 7, 16, 17, 18, 19) can be combined with any type of arrays to enable massive parallel screening;
- diverse forms of bispecific, bifunctional or generally modified antibodies can be produced very easily (Examples 12, 13, 14, 15, 18);
- the antibody splice variant, secreted into the culture medium, of an antibody (generally: a corresponding fusion protein; Examples 12, 13, 16, 18, 19) can be used for a rapid and simple characterization of a selected cell line (Example 9) or also a sub-library (Example 8) or also serve as a characterization of an established library;
- the secreted splice variant, in particular a human antibody, can under certain circumstances be used directly as a pharmacologically active substance;
- T cell libraries (Examples 16, 17) can be combined with cell libraries of MHC-bound antigens to search for T cell-specific epitopes.

The invention claimed is:

1. A method of producing a library of antibody-producing eukaryotic cells, the method comprising the steps of:
   (a) introducing specific FRT recombination signals into at least one chromosomal gene locus of a eukaryotic cell;
   (b) expanding the eukaryotic cell comprising the specific FRT recombination signals in the at least one gene locus;
   (c) introducing into the expanded eukaryotic cells of step (b) a plurality of nucleic acids comprising homologous sequences and encoding a plurality of antibodies;
   (d) introducing into the expanded eukaryotic cells of step (b) a nucleic acid encoding a Flp recombinase recognizing the specific FRT recombination signals; and
   (e) selecting eukaryotic cells expressing said plurality of antibodies,
   wherein the plurality of nucleic acids replace the at least one gene locus of the expanded eukaryotic cells,
   wherein a library of more than $10^2$ different antibody-producing eukaryotic cells is produced, and
   wherein members of the library of antibody-producing eukaryotic cells express an antibody encoded by the plurality of nucleic acids and bound to the surface of the members of the library of antibody-producing eukaryotic cells, wherein said antibody-producing eukaryotic cells are mammalian cells or hybridoma cells.

2. The method according to claim 1, wherein step (a) comprises homologous recombination of transfected DNA with the at least one gene locus, and wherein the transfected DNA comprises the specific recombination signals and a region homologous to DNA sequences flanking at least one gene locus of the eukaryotic cell.

3. The method according to claim 1, wherein the plurality of nucleic acids comprises vH genes, vlambda genes or vkappa genes.

4. The method according to claim 1, wherein the mammalian cells are neoplastic lymphocytes or precursors thereof, leukemia cells or malignant lymphoma cells.

5. The method according to claim 3, wherein the vH genes, vlambda genes or vkappa genes are human genes.

6. The method according to claim 3, wherein the at least one gene locus is an antibody locus selected from the group consisting of a vH gene, a vlambda gene and a vkappa gene.

7. The method according to claim 6, wherein the antibody is a monoclonal human antibody.

8. The method according to claim 7, wherein the monoclonal human antibody is bound to the surface of the member of the protein-producing eukaryotic cells by differentially splicing the constant domains of IgG, IgM, IgA, IgD or IgE.

9. The method according to claim 1, wherein more than $10^3$ different eukaryotic cells are obtained, each expressing a different protein.

10. The method according to claim 2, wherein the region homologous to DNA sequences flanking the at least one gene locus comprises at least 400 base pairs.

11. The method according to claim 2, wherein the region homologous to DNA sequences flanking the at least one gene locus comprises an IgG, IgM, IgA, IgD or IgE gene and an intron between the IgG, IgM, IgA, IgD or IgE gene and an M1 exon, and
   wherein the intron is shortened by more than 50 base pairs in the 5' end direction before the M1-exon of an IgG, IgM, IgA, IgD or IgE gene when compared to a naturally occurring intron between an IgG, IgM, IgA, IgD or IgE gene and the M1 exon.

12. The method according to claim 1, wherein the library of antibody-producing eukaryotic cells comprises more than $10^6$ cells.

13. The method according to claim 2, wherein the at least one gene locus is an antibody locus comprising an active vH gene, an active vlambda gene or an active vkappa gene.

14. The method according to claim 8, wherein the monoclonal human antibody is expressed by differentially splicing the constant domains of IgG.

15. The method according to claim 1, wherein the plurality of nucleic acids is obtained by error-prone PCR.

16. The method according to claim 3, wherein the plurality of nucleic acids is obtained by error-prone PCR.

17. The method according to claim 2, wherein the transfected DNA comprises a selectable marker.

18. The method according to claim 1, further comprising selecting the expanded eukaryotic cells by FACS.

19. The method according to claim 1, wherein the antibody is bound to the surface of the member of the library of antibody-producing eukaryotic cells by the immunoglobulin M1 domain.

20. The method according to claim 1, wherein the members of the library of antibody-producing eukaryotic cells do not express a resistance marker.

* * * * *